US 7,053,212 B2

(12) United States Patent  
Cameron et al.

(10) Patent No.: US 7,053,212 B2  
(45) Date of Patent: May 30, 2006

(54) ACYCLIC AMIDE AND SULFONAMIDE LIGANDS FOR THE ESTROGEN RECEPTOR

(75) Inventors: Kimberly O. Cameron, East Lyme, CT (US); Richard Chesworth, Mystic, CT (US)

(73) Assignee: Pfizer Inc., New York, NY (US)

( * ) Notice: Subject to any disclaimer, the term of this patent is extended or adjusted under 35 U.S.C. 154(b) by 177 days.

(21) Appl. No.: 10/666,811

(22) Filed: Sep. 17, 2003

(65) Prior Publication Data

US 2004/0110767 A1    Jun. 10, 2004

Related U.S. Application Data

(60) Provisional application No. 60/412,338, filed on Sep. 20, 2002.

(51) Int. Cl.
| | |
|---|---|
| C07D 279/12 | (2006.01) |
| C07D 295/12 | (2006.01) |
| C07D 413/12 | (2006.01) |
| C07D 211/18 | (2006.01) |
| C07D 207/04 | (2006.01) |

(52) U.S. Cl. .................. 544/58.1; 544/59; 544/149; 544/159; 546/153; 546/232; 548/565; 514/422; 514/428

(58) Field of Classification Search ............ 548/565; 546/153, 232; 544/149, 159, 58.1, 59; 514/422, 514/428

See application file for complete search history.

(56) References Cited

U.S. PATENT DOCUMENTS

| 4,243,804 A | 1/1981 | Krapcho ............... 544/162 |
|---|---|---|
| 4,271,188 A | 6/1981 | Hindley ............... 424/309 |
| 5,296,454 A * | 3/1994 | Goto et al. ............ 504/289 |
| 5,892,114 A | 4/1999 | Goldmann et al. ...... 564/161 |
| 5,958,934 A | 9/1999 | Berger et al. .......... 514/272 |
| 6,225,316 B1 | 5/2001 | Bos et al. ............. 514/252.18 |
| 6,511,980 B1 * | 1/2003 | Johnson et al. ........ 514/239.2 |
| 2002/0156281 A1 | 10/2002 | Booth et al. .......... 546/159 |

FOREIGN PATENT DOCUMENTS

| DE | 1122076 A * | 1/1962 |
|---|---|---|
| EP | 0585500 A1 * | 3/1994 |
| EP | 0873992 | 10/1998 |
| EP | 0947500 | 10/1999 |
| GB | 811130 | 4/1959 |
| GB | 2124615 A * | 2/1984 |
| GB | 2347422 | 9/2000 |
| JP | 04145067 A2 * | 5/1992 |
| WO | WO 9420467 | 9/1994 |
| WO | WO 9420467 A1 * | 9/1994 |
| WO | WO 0050398 | 8/2000 |
| WO | WO 0051983 | 8/2000 |

OTHER PUBLICATIONS

Cummings, Jeffrey, "Drug Therapy: Alzheimer's Disease," N. Engl. J. Med., vol. 351, pp. 56-67 (2004), especially at p. 61, 1st col., lines 31-47.*
Bowman, W. Russell, et al., "Synthesis of Oxindoles by Radical Cyclisation," Tetrahedron Letters, vol. 29(50), pp. 6657-6660 (1988) at p. 6659, lines 1-3.*
Linfield, Warner, et al., "Antibacterially Active Substituted Anilides of Carboxylic and Sulfonic Acids," J. Med. Chem., vol. 26(12), pp. 1741-1746 (Dec. 1983) at p. 1743, Table IV, compound 105.*

(Continued)

*Primary Examiner*—Kamal S. Saeed  
*Assistant Examiner*—Anthony J. Paviglianiti  
(74) *Attorney, Agent, or Firm*—Gregg C. Benson; John A. Wichtowski

(57) ABSTRACT

The present invention provides estrogen receptor (ER) ligands of structural formula (I)

the pharmaceutically acceptable salts, stereoisomers, and prodrugs thereof, and the pharmaceutically acceptable salts of the prodrugs, wherein $R^1$, $R^2$, $R^3$, $R^4$, $R^5$, X, and Q are as defined herein. The invention further provides pharmaceutical compositions comprising the compounds of formula (I), and methods for treating or preventing diseases, disorders, conditions, or symptoms mediated by an ER which comprise administering to a mammalian subject in need of treatment therewith, an effective amount of a compound of formula (I), or a pharmaceutically acceptable salt, stereoisomer, or prodrug thereof, or a pharmaceutically acceptable salt of the prodrug, or a pharmaceutical composition comprising a compound of formula (I), or a pharmaceutically acceptable salt, stereoisomer, or prodrug thereof, or a pharmaceutically acceptable salt of the prodrug. The invention further provides pharmaceutical compositions comprising combinations of the compounds of formula (I) and one or more of sodium fluoride, estrogen, a bone anabolic agent, a growth hormone or growth hormone secretagogue, a prostaglandin agonist/antagonist, and a parathyroid hormone, and methods of treating or preventing diseases, disorders, conditions, or symptoms mediated by an ER comprising the administration of an effective amount of such combination to a mammalian subject in need of treatment therewith.

7 Claims, No Drawings

OTHER PUBLICATIONS

Munusamy, R., et al., "Cathodic reduction of N-(2-iodophenyl)-N-alkylcinnamides," J. Chem. Soc. (Perkin Trans. 2), vol. 7, pp. 1154-1166 (Jun. 11, 2001) at p. 1154, compounds 1b, 1f, 1h, 1i, 1k.*

Petigara, R.B., et al., "Synthesis and Central Nervous System Depressant Activity of New Piperazine and Related Derivatives," J. Med. Chem., vol. 12, pp. 865-870, at p. 868, Table II.*

Patent Abstract of Japan Publication No. 2000072734 of Jul. 3, 2000.

Labrie, et al., "EM-652 (SCH 57068), a third generation SERM acting as pure antiestrogen in the mammary gland and endometrium", *Journal of Steroid Biochemistry and Molecular Biology* 69, pp. 51-84 (1999), XP-000852985.

Database Crossfire Beilstein Registry No. 2824215, abstract & J.Gen.Chem. 32, p. 712 (1962), XP-002260924.

Database Crossfire Beilstein Registry No. 405454, abstract & Yakugaku Sasshi, 86, pp. 107-109 (1966), XP002260925.

* cited by examiner

ACYCLIC AMIDE AND SULFONAMIDE LIGANDS FOR THE ESTROGEN RECEPTOR

CROSS REFERENCE TO RELATED APPLICATION

This application claims priority of U.S. provisional application No. 60/412,338, filed Sep. 20, 2002.

BACKGROUND OF THE INVENTION

As a mediator of the actions of estrogenic hormones, the estrogen receptor (ER) plays a central role in regulating an array of normal physiological processes involved in the development and function of the reproductive system, as well as many other aspects of health, such as bone density, cardiovascular health, and the like.

It is known that compounds that bind to the ER are potentially useful in the treatment of a wide range of disease states. These include estrogen agonists for the treatment of diseases linked to estrogen deficiency, such as osteoporosis, cardiovascular and neurodegenerative diseases in post-menopausal women, and estrogen antagonists for treatment of breast and uterine cancer. Furthermore, it is known that certain ligands, such as tamoxifen, display mixed agonist/antagonist action, i.e., they are estrogen agonists, estrogen antagonists, or partial estrogen antagonists when binding to the ERs of different tissues.

Estrogen and bisphosphonates are the current agents of choice in preventing osteoporosis or post-menopausal bone loss in women. However, estrogen stimulates the uterus and is associated with an increased risk of endometrial cancer. Although the risk of endometrial cancer is thought to be reduced by concurrent use of a progesterone, there remains concern about possible increased risk of breast cancer with the use of estrogen.

Until recently, it had been assumed that estrogen binds to a single ER in cells, causing conformational changes that result in release from heat-shock proteins and binding of the receptor as a dimer to the so-called "estrogen response element" in the promoter region of a variety of genes. Further, pharmacologists have generally believed that non-steroidal, small molecule ligands compete for binding of estrogen to ER, thus acting as either antagonists or agonists in each tissue where the ER is expressed. Thus, such ligands have traditionally been classified as either pure agonists or antagonists. This interpretation, however, is no longer believed to be correct.

Progress over the last few years has shown that ER associates with co-activators (e.g., SRC-1, CBP, and SRA) and co-repressors (e.g., SMRT and N-CoR) that modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for the regulation of these genes.

Given the complexity of ER signaling, as well as the various types of tissue that expresses ER and its co-factors, it is currently believed that ER ligands can no longer be classified simply as either pure agonists or antagonists. Therefore, the acronym SERM (selective estrogen receptor modulator) has been coined. SERMs bind to the ER, but may act as an agonist or antagonist of estrogen in different tissues and different genes. For example, two of the most well-known drugs that behave as SERMs are tamoxifen (AstraZeneca) and raloxifene (Eli Lilly & Co.). Studies with these two compounds, as well as other SERMs currently in development, have demonstrated that the affinity of a SERM for its receptor, in many cases, does not correlate with the pharmacological effect it elicits. Therefore, ligand binding assays traditionally employed in screening for novel ER modulators have not distinguished between tissue selectivity and agonist/antagonist behavior.

More recently, a second ER, designated ERβ, has been identified and cloned. See Katzenellenbogen, et al., Endocrinology, 138, 861–862 (1997). ERβ and the classical ER, re-named ERα, have significantly different amino acid sequences in the ligand binding domain and carboxy-terminal transactivation domains (~56% amino acid identity) and only 20% homology in their amino-terminal domain. This suggests that some ligands may have higher affinity for one ER over the other. Further, ligand-dependent conformational changes of the two receptors, and interaction with co-factors, will result in quite different biological actions of a single ligand. In other words, a ligand that acts as an agonist on ERα may very well serve as an antagonist on ERβ. An example of such behavior has been disclosed by Paech, et al., Science, 277, 1508–1510 (1997). ERα and ERβ were shown to signal in opposite ways when complexed with the natural hormone estradiol from AP1 site: with ERα, 17β-estradiol activated transcription, whereas with ERβ, 17β-estradiol inhibited transcription.

ERα and ERβ, have both overlapping and disparate tissue distributions. Tissues that express high levels of ERβ include the prostate, testes, ovaries, and certain regions of the brain.

With the identification of ERβ, and the recognition that ERα and ERβ serve different biological roles, ER-selective modulators would possess significant clinical utility in the treatment or prevention of diseases, disorders, conditions, or symptoms mediated by an ER. In addition, ER-selective modulators that have the capacity to selectively bind to, or activate, the ERα and ERβ subtypes would be useful in elucidating the biology of the two receptors and would assist in the development of estrogen pharmaceuticals with improved tissue selectivity.

SUMMARY OF THE INVENTION

The present invention provides estrogen receptor (ER) ligands of structural formula (I)

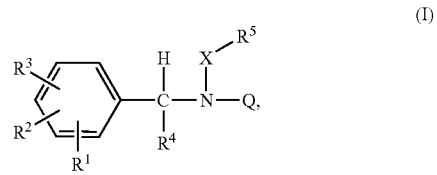

the pharmaceutically acceptable salts, stereoisomers, and prodrugs thereof, and the pharmaceutically acceptable salts of the prodrugs, wherein $R^1$, $R^2$, $R^3$, $R^4$, $R^5$, X, and Q are as defined hereinbelow.

The invention further provides pharmaceutical compositions comprising the compounds of formula (I), and methods for treating or preventing diseases, disorders, conditions, or symptoms mediated by an ER which comprise administering to a mammalian subject in need of treatment therewith, an effective amount of a compound of formula (I), or a pharmaceutically acceptable salt, stereoisomer, or prodrug thereof, or a pharmaceutically acceptable salt of the prodrug, or a pharmaceutical composition comprising a compound of formula (I), or a pharmaceutically acceptable salt, stereoisomer, or prodrug thereof, or a pharmaceutically acceptable salt of the prodrug.

The invention further provides pharmaceutical compositions comprising combinations of the compounds of formula (I) and one or more of sodium fluoride, estrogen, a bone anabolic agent, a growth hormone or growth hormone secretagogue, a prostaglandin agonist/antagonist, and a parathyroid hormone, and methods of treating or preventing diseases, disorders, conditions, or symptoms mediated by an ER comprising the administration of an effective amount of such combination to a mammalian subject in need of treatment therewith.

DETAILED DESCRIPTION OF THE INVENTION

The present invention provides estrogen receptor (ER) ligands of structural formula (I)

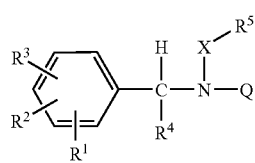

(I)

the pharmaceutically acceptable salts, stereoisomers, and prodrugs thereof, and the pharmaceutically acceptable salts of the steroisomers and prodrugs, wherein:

Q is

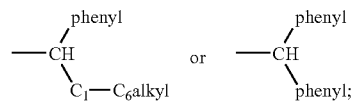

or a six-membered heteroaryl ring containing one or two nitrogen atoms, wherein said heteroaryl ring is optionally substituted with $R^9$ and/or Z;

$R^1$, $R^2$, $R^3$, and $R^9$ are, independently, hydrogen; hydroxy; halogen; cyano; —$(C_1-C_6)$alkyl, optionally substituted with 1–3 fluorine atoms; and —$O(C_1-C_6)$alkyl, optionally substituted with 1–3 fluorine atoms;

$R^4$ is hydrogen or —$(C_1-C_6)$alkyl;

$R^5$ is —$(C_1-C_7)$alkyl, optionally substituted with from 1–6 halogen atoms; —$(C_2-C_6)$alkenyl; —$(C_2-C_6)$alkenyl-M; or —$(CH_2)_n$-M, wherein n is 0–5; and wherein M is:

(i) a fully saturated 3–8 membered ring, or a partially saturated, or fully saturated 5–8 membered ring, optionally having from 1–4 heteroatoms independently selected from the group consisting of oxygen, nitrogen, and sulfur; or (ii) a bicyclic ring comprising two fused partially saturated, fully saturated, or fully unsaturated 5- or 6-membered rings, optionally having from 1–4 heteroatoms independently selected from the group consisting of oxygen, nitrogen and sulfur; wherein M is optionally substituted with from 1–3 substituents independently selected from the group consisting of hydroxy; halogen; cyano; nitro; formyl; amino; carbamoyl; thiol; —$(C_1-C_6)$alkyl or —$O(C_1-C_6)$alkyl, optionally substituted with from 1–5 halogen atoms; —$(C_3-C_8)$cycloalkyl or phenyl, optionally substituted with from 1–3 halogen atoms; —$SO(C_1-C_6)$alkyl or —$SO_2(C_1-C_6)$alkyl, optionally substituted with from 1–5 halogen atoms; —$S(C_1-C_6)$alkyl, optionally substituted with from 1–5 halogen atoms; —$(C_1-C_4)$alkoxycarbonyl; —$(C_1-C_6)$alkyl-$(C_3-C_8)$cycloalkyl; —$(C_0-C_4)$sulfonamido; mono-N- or di-N,N-$(C_1-C_4)$alkylcarbamoyl; mono-N or di-N,N-$(C_1-C_4)$alkylamino-$SO_2$; mono-N or di-N,N-$(C_1-C_4)$alkylamino; —$(C_1-C_8)$alkanoyl; —$(C_1-C_4)$alkanoylamino; or —$(C_1-C_4)$alkoxycarbonylamino;

X is CO or $SO_2$;

Z is —$O(CH_2)_n$—$NR^aR^b$; —$(CH_2)_n$—$NR^aR^b$; —$CH$=$CH$—$C(O)$—$NR^aR^b$; —$(CH_2)_n$—$COOH$; —$CH$=$CH$—$COOH$; —$O(C_1-C_6)$alkyl; —$CH$=$CH$—$C(O)O(C_1-C_6)$alkyl; and —$(CH_2)_n$—$OH$; wherein each n is 0–5 inclusive, provided that when Z is —O—$(CH_2)_n$—$NR^aR^b$, n is 2–5;

$R^a$ and $R^b$ are, independently, hydrogen; —$(C_1-C_6)$alkyl; —$(CH_2)_n$—$(C_3-C_8)$cycloalkyl; —$(CH_2)_{2-5}$—$OH$; —$(CH_2)_n$-phenyl; —$(CH_2)_n$-heteroaryl; —$(CH_2)_n$-heterocycloalkyl; and

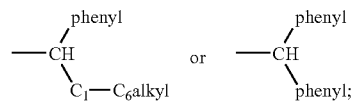

wherein each n is 0–5 inclusive, and wherein said cycloalkyl, phenyl, heteroaryl, and heterocycloalkyl is optionally substituted with from 1–3 substituents independently selected from the group consisting of hydroxy; halogen; cyano; nitro; amino; carbamoyl; —$(C_1-C_6)$alkyl or —$O(C_1-C_6)$alkyl, optionally substituted with from 1–5 halogen atoms; —$(C_1-C_3)$alkyl-$O(C_1-C_3)$alkyl; —$(C_1-C_4)$OH; carboxylate; —$(C_1-C_3)$phenyl; —$(C_3-C_8)$cycloalkyl; phenyl, optionally substituted with from 1–3 halogen atoms; —$SO(C_1-C_6)$alkyl or —$SO_2(C_1-C_6)$alkyl, optionally substituted with from 1–5 halogen atoms; —$S(C_1-C_6)$alkyl, optionally substituted with from 1–5 halogen atoms; —$(C_1-C_4)$alkoxycarbonyl; —$(C_1-C_6)$alkyl-$(C_3-C_8)$cycloalkyl; sulfonamido; —$(C_1-C_4)$alkylsulfonamido; mono-N- or di-N,N-$(C_1-C_4)$alkylcarbamoyl; mono-N or di-N,N-$(C_1-C_4)$alkylamino-$SO_2$; mono-N or di-N,N-$(C_1-C_4)$alkylamino; —$(C_1-C_8)$alkanoyl; —$(C_1-C_4)$alkanoylamino; or —$(C_1-C_4)$alkoxycarbonylamino; or $R^a$ and $R^b$, taken together with the nitrogen atom to which they are attached, form a 3–7 membered heterocycloalkyl ring having from 1–2 heteroatoms independently selected from the group consisting of nitrogen, oxygen, and sulfur; or a 5–7 membered ring fused to a phenyl ring, wherein said 3–7 membered heterocycloalkyl ring, or said 5–7 membered ring fused to a phenyl ring, is optionally substituted with from 1–3 substituents independently selected from the group consisting of hydroxy; halogen; cyano; nitro; amino; carbamoyl; —$(C_1-C_6)$alkyl or —$O(C_1-C_6)$alkyl, optionally substituted with from 1–5 halogen atoms; —$(C_1-C_3)$alkyl-$O(C_1-C_3)$alkyl; —$(C_1-C_4)$OH; carboxylate; —$(C_1-C_3)$phenyl; —$(C_3-C_8)$cycloalkyl; phenyl, optionally substituted with from 1–3 halogen atoms; —$SO(C_1-C_6)$alkyl or —$SO_2(C_1-C_6)$alkyl, optionally substituted with from 1–5 halogen atoms; —$S(C_1-C_6)$alkyl, optionally substituted with from 1–5 halogen atoms; —$(C_1-C_4)$alkoxycarbonyl; —$(C_1-C_6)$alkyl-$(C_3-C_8)$cycloalkyl; —$(C_0-C_4)$sulfonamido; —($C_1$–$C_4$)cycloalkylsulfonamido; mono-N- or di-N,N-($C_1$–$C_4$)alkylcarbamoyl; mono-N or di-N,N-($C_1$–$C_4$)alkylamino-$SO_2$; mono-N or di-N,N-($C_1$–$C_4$)alkylamino; —($C_1$–$C_8$)alkanoyl; —($C_1$–$C_4$)alkanoylamino; or —($C_1$–$C_4$)alkoxycarbonylamino.

A generally preferred subgroup of the compounds of formula (I) comprises those compounds wherein:

Q is phenyl; pyridyl; pyrimidyl; or pyrazinyl, each optionally substituted with $R^9$ and/or Z;

$R^5$ is —($C_1$–$C_6$)alkyl, optionally substituted with from 1–6 halogen atoms; —($C_2$–$C_6$)alkenyl; —($C_2$–$C_6$)alkenyl-M; or —$(CH_2)_n$-M, wherein n is 1 to 3; and M is selected from the group consisting of cyclopropyl; cyclobutyl; cyclopentyl; cyclohexyl; phenyl; quinolinyl; isoquinolinyl; naphthalenyl; isoxazolyl; oxazolyl; thiazolyl; furanyl; isothiazolyl; thienyl; imidazolyl; pyrazolyl; pyridyl; pyrimidyl; and pyrazinyl, each optionally substituted with from 1–3 substituents independently selected from the group consisting of hydroxy; halogen; cyano; nitro; formyl; amino; carbamoyl; thiol; —($C_1$–$C_6$)alkyl or —O($C_1$–$C_6$)alkyl, optionally substituted with from 1–5 halogen atoms; —($C_3$–$C_8$)cycloalkyl or phenyl, optionally substituted with from 1–3 halogen atoms; —SO($C_1$–$C_6$)alkyl or —$SO_2$($C_1$–$C_6$)alkyl, optionally substituted with from 1–5 halogen atoms; —S($C_1$–$C_6$)alkyl, optionally substituted with from 1–5 halogen atoms; —($C_1$–$C_4$)alkoxycarbonyl; —($C_1$–$C_6$)alkyl-($C_3$–$C_8$)cycloalkyl; —($C_0$–$C_4$)sulfonamido; mono-N- or di-N,N-($C_1$–$C_4$)alkylcarbamoyl; mono-N or di-N,N-($C_1$–$C_4$)alkylamino-$SO_2$; mono-N or di-N,N-($C_1$–$C_4$)alkylamino; —($C_1$–$C_8$)alkanoyl; —($C_1$–$C_4$)alkanoylamino; or —($C_1$–$C_4$)alkoxycarbonylamino;

$R^a$ and $R^b$ are, independently, hydrogen; —($C_1$–$C_6$)alkyl; —$(CH_2)_n$—($C_3$–$C_8$)cycloalkyl; —$(CH_2)_n$—OH; —$(CH_2)_n$-phenyl; —$(CH_2)_n$-heteroaryl; and —$(CH_2)_n$-heterocycloalkyl; wherein each n is 1 to 5 inclusive, and said heteroaryl is selected from the group consisting of isoxazolyl; oxazolyl; thiazolyl; isothiazolyl; thienyl; furanyl; imidazolyl; pyrazolyl; pyridyl; pyrimidyl; pyrazinyl; triazolyl; thiadiazolyl; oxadiazolyl; pyridazinyl; and triazinyl, each optionally substituted with from 1–3 substituents independently selected from the group consisting of hydroxy; halogen; cyano; nitro; amino; carbamoyl; —($C_1$–$C_6$)alkyl or —O($C_1$–$C_6$)alkyl, optionally substituted with from 1–5 halogen atoms; —($C_1$–$C_3$)alkyl-O($C_1$–$C_3$)alkyl; —($C_1$–$C_4$)OH; carboxylate; —($C_1$–$C_3$)phenyl; —($C_3$–$C_8$)cycloalkyl; phenyl, optionally substituted with from 1–3 halogen atoms; and —($C_1$–$C_4$)alkoxycarbonyl; —($C_1$–$C_6$)alkyl-($C_3$–$C_8$)cycloalkyl; or $R^a$ and $R^b$, taken together with the nitrogen atom to which they are attached, form a heterocycloalkyl ring selected from the group consisting of piperidine; pyrrolidine; morpholine; piperazine; tetrahydro-2H-1,4-thiazine; azacycloheptane; tetrahydroisoquinoline; tetrahydroquinoline; azetidine; benzazepine; 1,3-dihydroisoindole; and indoline; each optionally substituted with from 1–3 substituents independently selected from the group consisting of hydroxy; halogen; cyano; nitro; amino; carbamoyl; —($C_1$–$C_6$)alkyl or —O($C_1$–$C_6$)alkyl, optionally substituted with from 1–5 halogen atoms; —($C_1$–$C_3$)alkyl-O($C_1$–$C_3$)alkyl; —($C_1$–$C_4$)OH; carboxylate; —($C_1$–$C_3$)phenyl; —($C_3$–$C_8$)cycloalkyl; phenyl, optionally substituted with from 1–3 halogen atoms; —($C_1$–$C_4$)alkoxycarbonyl; and —($C_1$–$C_6$)alkyl-($C_3$-C8)cycloalkyl.

Another generally preferred subgroup of the compounds of formula (I) comprises those compounds wherein:

Q is phenyl;

$R^1$, $R^2$, $R^3$, and $R^9$ are, independently, hydrogen; hydroxy; halogen; —($C_1$–$C_4$)alkyl, optionally substituted with 1–3 fluorine atoms; and —O($C_1$–$C_2$)alkyl, optionally substituted with 1–3 fluorine atoms;

$R^4$ is hydrogen;

$R^5$ is -(ethenyl)-M or -M, wherein M is cyclopentyl, cyclohexyl, phenyl, or isoxazolyl, optionally substituted with from 1–5 halogen atoms; —($C_1$–$C_4$)alkyl, optionally substituted with from 1–3 halogen atoms; or —O($C_1$–$C_4$)alkyl, optionally substituted with from 1–3 halogen atoms;

Z is —$O(CH_2)_n$—$NR^aR^b$; —$(CH_2)_n$—$NR^aR^b$; —CH=CH—C(O)—$NR^aR^b$; —O($C_1$–$C_8$)alkyl; and —$(CH_2)_n$—OH; wherein each n is 1–5 inclusive, provided that when Z is —O—$(CH_2)_n$—$NR^aR^b$, n is 2–4; and $R^a$ and $R^b$ are, independently, hydrogen; —($C_1$–$C_4$)alkyl; —$(CH_2)_n$—($C_5$–C7)cycloalkyl; —$(CH_2)_n$—OH; —$(CH_2)_n$-phenyl; —$(CH_2)_n$-heteroaryl; and —$(CH_2)_n$-heterocycloalkyl; wherein each n is 1–3 inclusive, and said heteroaryl is pyridyl or imidazolyl, wherein each of said pyridyl or imidazolyl is optionally substituted with from 1–3 substituents independently selected from the group consisting of hydroxy; halogen; —($C_1$–$C_4$)alkyl, optionally substituted with from 1–5 halogen atoms; —($C_1$–$C_3$)alkyl-O($C_1$–$C_3$)alkyl; —($C_1$–$C_3$)OH; carboxylate; —($C_1$–$C_3$)phenyl; —($C_5$–$C_7$)cycloalkyl; and phenyl, optionally substituted with from 1–3 halogen atoms; or $R^a$ and $R^b$, taken together with the nitrogen atom to which they are attached, form a heterocycloalkyl ring selected from the group consisting of piperidine; pyrrolidine; morpholine; piperazine; tetrahydroisoquinoline; tetrahydroquinoline; and tetrahydro-2H-1,4-thiazine, each optionally substituted with from 1–3 substituents independently selected from the group consisting of hydroxy; halogen; —($C_1$–$C_4$)alkyl, optionally substituted with from 1–5 halogen atoms; —($C_1$–$C_3$)alkyl-O($C_1$–$C_3$)alkyl; —($C_1$–$C_3$)OH; carboxylate; —($C_1$–$C_3$)phenyl; —($C_5$–$C_7$)cycloalkyl; and phenyl, optionally substituted with from 1–3 halogen atoms.

Yet another generally preferred subgroup of compounds of formula (I) comprises those compounds wherein:

Q is phenyl;

$R^1$, $R^2$, $R^3$, and $R^9$ are, independently, hydrogen; hydroxy; halogen; —($C_1$–$C_3$)alkyl, or —$CF_3$;

$R^5$ is ethenylphenyl; cyclohexyl; or phenyl, each optionally substituted with from 1–3 substituents independently selected from the group consisting of halogen, hydroxy, —($C_1$–$C_3$)alkyl, —$CF_3$; and —$OCH_3$;

X is CO or $SO_2$;

Z is —$O(CH_2)_2$—$NR^aR^b$; or —$(CH_2)_3$—$NR^aR^b$; and $R^a$ and $R^b$ are, independently, hydrogen or —($C_5$–$C_7$)cycloalkyl, optionally substituted with from 1–3 substituents independently selected from the group consisting of hydroxy; halogen; —($C_1$–$C_3$)alkyl, optionally substituted with from 1–3 halogen atoms; —($C_1$–$C_2$)alkyl-O($C_1$–$C_2$)alkyl; —($C_1$–$C_2$)OH; carboxylate; and —$CH_2$-phenyl; or $R^a$ and $R^b$, taken together with the nitrogen atom to which they are attached, form a heterocycloalkyl ring selected from the group consisting of piperidine; pyrrolidine; morpholine; and tetrahydro-2H-1,4-thiazine, each optionally substituted with from 1–3 substituents independently selected from the group consisting of hydroxy; halogen; —($C_1$–$C_3$)alkyl, optionally substituted with from 1–3 halogen atoms; —($C_1$–$C_2$)alkyl-($C_1$–$C_2$)alkoxy; —($C_1$–$C_2$)OH; carboxylate; and —$CH_2$-phenyl.

An especially preferred subgroup of the compounds of formula (I) comprises those compounds selected from the group consisting of:

cyclohexanecarboxylic acid (4-hydroxy-benzyl)-[4-(2-pyrrolidin-1-yl-ethoxy)-phenyl]-amide;

cyclohex-3-enecarboxylic acid (4-hydroxy-benzyl)-[4-(2-pyrrolidin-1-yl-ethoxy)-phenyl]-amide;

2-phenyl-ethenesulfonic acid (4-hydroxy-benzyl)-[4-(2-pyrrolidin-1-yl-ethoxy)-phenyl]-amide;

N-(3-hydroxy-benzyl)-4-methoxy-N-[4-(2-pyrrolidin-1-yl-ethoxy)-phenyl]-benzenesulfonamide;

2-phenyl-ethenesulfonic acid (3-hydroxy-benzyl)-[4-(2-pyrrolidin-1-yl-ethoxy)-phenyl]-amide;

N-{4-[3-(4-benzyl-piperidin-1-yl)-propyl]-phenyl}-N-(4-hydroxy-benzyl)-benzenesulfonamide;

2-chloro-N-(4-hydroxy-benzyl)-N-[4-(2-pyrrolidin-1-yl-ethoxy)-phenyl]-benzenesulfonamide;

N-(4-hydroxy-benzyl)-2,4,6-trimethyl-N-[4-(2-pyrrolidin-1-yl-ethoxy)-phenyl]-benzenesulfonamide;

N-(3-hydroxy-benzyl)-2,4,6-trimethyl-N-[4-(2-pyrrolidin-1-yl-ethoxy)-phenyl]-benzenesulfonamide;

4-[1-(4-methoxy-benzenesulfonyl)-6-(2-pyrrolidin-1-yl-ethoxy)-1,2,3,4-tetrahydro-quinolin-2-yl]-phenol;

N-(3-hydroxy-benzyl)-2,4,6-triisopropyl-N-[4-(2-pyrrolidin-1-yl-ethoxy)phenyl]-benzenesulfonamide;

2,4-dichloro-N-(3-hydroxy-benzyl)-6-methyl-N-[4-(2-pyrrolidin-1-yl-ethoxy)-phenyl]-benzenesulfonamide;

N-(3-hydroxy-benzyl)-N-[4-(2-pyrrolidin-1-yl-ethoxy)-phenyl]-4-trifluoromethyl-benzamide;

5-chloro-N-(4-hydroxy-benzyl)-2-methyl-N-[4-(2-pyrrolidin-1-yl-ethoxy)-phenyl]-benzenesulfonamide;

4-bromo-N-(2-chloro-4-hydroxy-benzyl)-2-methyl-N-[4-(2-pyrrolidin-1-yl-ethoxy)-phenyl]-benzenesulfonamide;

2-chloro-N-(2-chloro-4-hydroxy-benzyl)-4-fluoro-N-[4-(2-pyrrolidin-1-yl-ethoxy)-phenyl]-benzenesulfonamide;

2,4-dichloro-N-(2-chloro-4-hydroxy-benzyl)-N-[4-(2-pyrrolidin-1-yl-ethoxy)-phenyl]-benzenesulfonamide;

4-bromo-2-ethyl-N-(4-hydroxy-benzyl)-N-[4-(2-pyrrolidin-1-yl-ethoxy)-phenyl]-benzenesulfonamide;

4-bromo-N-(4-hydroxy-benzyl)-2-methyl-N-[4-(2-pyrrolidin-1-yl-ethoxy)-phenyl]-benzenesulfonamide;

2,4-dichloro-N-(4-hydroxy-benzyl)-6-methyl-N-[4-(2-pyrrolidin-1-yl-ethoxy)-phenyl]-benzenesulfonamide;

2,4-dichloro-N-(4-hydroxy-benzyl)-N-[4-(2-pyrrolidin-1-yl-ethoxy)-phenyl]-benzenesulfonamide;

N-(3-hydroxy-benzyl)-2,4,6-trimethyl-N-[4-(3-pyrrolidin-1-yl-propyl)-phenyl]-benzenesulfonamide;

N-(3-hydroxy-benzyl)-N-{4-[3-(2-hydroxymethyl-pyrrolidin-1-yl)-propyl]-phenyl}-2,4,6-trimethyl-benzenesulfonamide;

N-[4-(3-cyclopentylamino-propyl)-phenyl]-N-(3-hydroxy-benzyl)-2,4,6-trimethyl-benzenesulfonamide;

N-(3-hydroxy-benzyl)-2,4,6-trimethyl-N-[4-(2-piperidin-1-yl-ethoxy)-phenyl]-benzenesulfonamide;

N-(3-hydroxy-benzyl)-2,4,6-trimethyl-N-[4-(3-thiomorpholin-4-yl-propyl)-phenyl]-benzenesulfonamide;

N-{4-[3-(2,6-dimethyl-morpholin-4-yl)-propyl]-phenyl}-N-(3-hydroxy-benzyl)-2,4,6-trimethyl-benzenesulfonamide;

N-(3-hydroxy-benzyl)-2,4,6-trimethyl-N-{4-[3-(4-methyl-piperidin-1-yl)-propyl]-phenyl}-benzenesulfonamide;

N-(3-hydroxy-benzyl)-2,4,6-trimethyl-N-{4-[3-(2-propyl-piperidin-1-yl)-propyl]-phenyl}-benzenesulfonamide;

N-(3-hydroxy-benzyl)-2,4,6-trimethyl-N-{4-[3-(2-methyl-piperidin-1-yl)-propyl]-phenyl}-benzenesulfonamide;

N-(3-hydroxy-benzyl)-2,4,6-trimethyl-N-{4-[3-(2-methyl-pyrrolidin-1-yl)-propyl]-phenyl}-benzenesulfonamide;

N-(3-hydroxy-benzyl)-2,4,6-trimethyl-N-[4-(3-piperidin-1-yl-propyl)-phenyl]-benzenesulfonamide;

N-(2-chloro-4-hydroxy-benzyl)-N-{4-[3-(2-methoxymethyl-pyrrolidin-1-yl)-propyl]-phenyl}-2,4,6-trimethyl-benzenesulfonamide;

1-(3-{4-[(2-chloro-4-hydroxy-benzyl)-(2,4,6-trimethyl-benzenesulfonyl)-amino]-phenyl}-propyl)-pyrrolidine-2-carboxylic acid;

N-{4-[3-(2,6-dimethyl-piperidin-1-yl)-propyl)-phenyl}-N-(3-hydroxy-benzyl)-2,4,6-trimethyl-benzenesulfonamide;

N-(3-hydroxy-benzyl)-N-[4-(3-hydroxy-propyl)-phenyl]-2,4,6-trimethylbenzenesulfonamide;

N-(2-chloro-4-hydroxy-benzyl)-4-methoxy-N-[4-(2-pyrrolidin-1-yl-ethoxy)-phenyl]-benzenesulfonamide;

4-chloro-N-(4-hydroxy-benzyl)-N-[4-(2-pyrrolidin-1-yl-ethoxy)-phenyl]-benzenesulfonamide; and the pharmaceutically acceptable salts, stereoisomers, and prodrugs thereof, and the pharmaceutically acceptable salts of the steroisomers and prodrugs.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix $(C_a-C_b)$alkyl indicates an alkyl moiety of the integer "a" to "b" carbon atoms, inclusive. Thus, for example, $(C_1-C_6)$alkyl refers to an alkyl group of one to six carbon atoms inclusive, for example, methyl, ethyl, propyl, isopropyl, butyl, isobutyl, pentyl, isopentyl, hexyl, and the like, including all regioisomeric forms thereof, and straight and branched chain forms thereof.

The term "alkyl" refers to straight or branched, monovalent, saturated aliphatic chains of carbon atoms and includes, for example, methyl, ethyl, propyl, isopropyl, butyl, isobutyl, pentyl, isopentyl, hexyl, and the like.

The term "alkenyl" denotes a straight or branched-chain hydrocarbon having one or more carbon-carbon double bonds.

The term "aryl" denotes a cyclic, aromatic hydrocarbon. Examples of aryl groups include phenyl, naphthyl, and biphenyl.

The term "cycloalkyl" denotes a cyclic hydrocarbon. Examples of cycloalkyl groups include cyclopropyl, cyclobutyl, cyclopentyl, cyclohexyl, and cycloheptyl.

The term "cycloalkenyl" denotes a cycloalkyl group having one or more double or triple bonds, or a combination of double bonds and triple bonds. Examples of cycloalkyenyl groups include cyclopentenyl, cyclohexenyl, cyclohexadienyl, cyclobutadienyl, and the like.

The phrase "estrogen agonist" is intended to indicate a compound capable of binding to the ER site(s) in mammalian tissues, thus mimicking the actions of estrogen in one or more of the tissues.

The phrase "estrogen antagonist" is intended to indicate a compound capable of binding to the ER site(s) in mammalian tissues, thus blocking the actions of estrogen in one or more of the tissues.

The term "halogen" represents chloro, fluoro, bromo, and iodo.

The term "heteroaryl" denotes a monocyclic or bicyclic, aromatic hydrocarbon wherein one or more carbon atoms have been replaced with heteroatoms selected from the group consisting of nitrogen, oxygen, and sulfur. If the heteroaryl group contains more than one heteroatom, the heteroatoms may be the same or different. Preferred heteroaryl groups are five- and six-membered rings and contain from one to three heteroatoms independently selected from oxygen, nitrogen, and sulfur. Examples of preferred five- and six-membered heteroaryl groups include benzo[b]thienyl, chromenyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyridyl, pyrimidyl, pyrrolyl, quinolizinyl, quinolyl, quinoxalinyl, thiazolyl, thienyl, triazinyl, triazolyl, and xanthenyl.

The term "heterocycloalkyl", as employed in the situation wherein $R^a$ and $R^b$ hereinabove, taken together, form a 3–7 membered heterocycloalkyl ring, denotes a cycloalkyl group in which one of the carbon atoms has been replaced with a heteroatom selected from the group consisting of nitrogen, oxygen, and sulfur. Examples of such heterocycloalkyl groups include azabicycloheptanyl, azetidinyl, benzazepinyl, 1,3-dihydroisoindolyl, indolinyl, tetrahydrofuryl, tetrahydroquinolinyl, tetrahydroisoquinolinyl, morpholinyl, piperazinyl, piperidyl, pyrrolidinyl, and, tetrahydro-2H-1,4-thiazinyl. It is also possible for the heterocycloalkyl group to have one or more double or triple bonds, or a combination of double bonds and triple bonds, yet is not aromatic.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "mammal" means animals including, for example, dogs, cats, cows, sheep, horses, and humans. Preferred mammals include humans.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e.g., an organic radical is a group of atoms that imparts characteristic properties to a compound containing it, or which remains unchanged during a series of reactions, or transformations.

The term "salts" refers to organic and inorganic salts of a compound of formula (I), or a stereoisomer, or prodrug thereof. These salts can be prepared in situ during the final isolation and purification of a compound, or by separately reacting a compound of formula (I), or a stereoisomer or prodrug thereof, with a suitable organic or inorganic acid or base and isolating the salt thus formed. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, as the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1–19 (1977).

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond, both the cis- and trans-forms, as well as mixtures thereof, are embraced within the scope of the invention.

Diasteriomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of formula (I) may be atropisomers (e.g., substituted biaryls) and are also considered as part of the invention.

The compounds of formula (I) may exist in unsolvated as well as solvated forms with pharmaceutically acceptable solvents, such as water, ethanol, and the like, and it is intended that the invention embrace both solvated and unsolvated forms.

It is also possible that the compounds of formula (I) may exist in different tautomeric forms, and all such forms are embraced within the scope of the invention.

The present invention also embraces isotopically-labelled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The compounds of formula (I), the stereoisomers and prodrugs thereof, and the pharmaceutically acceptable salts of the compounds, stereoisomers, or prodrugs, that contain the aforementioned isotopes and/or other isotopes of the other atoms are intended to be within the scope of the instant invention.

Certain isotopically-labelled compounds of formula (I), for example those compounds into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their relative ease of preparation and facile detection. Furthermore, substitution with heavier isotopes such as deuterium, i.e., $^2H$, may afford certain therapeutic advantages resulting from greater metabolic stability, for example, increased in vivo half-life, or reduced dosage requirements and, hence, may be preferred in some circumstances. The isotopically-labelled compounds of formula (I) can generally be prepared by carrying out procedures analogous to those disclosed in the Schemes and/or Examples set forth hereinbelow, by substituting an isotopically-labelled reagent for a non-isotopically-labelled reagent.

In another aspect, the invention provides methods for treating or preventing a disease, disorder, condition, or symptom mediated by an estrogen receptor, or caused by lowered estrogen level in a mammal, which methods comprise administering to said mammal a therapeutically effective amount of a compound of formula (I), or a pharmaceutically acceptable salt, stereoisomer, or prodrug thereof, or a pharmaceutically acceptable salt of the stereoisomer or prodrug; or a pharmaceutical composition comprising such compounds, pharmaceutically acceptable salts, stereoisomers, or prodrugs; or combinations of the compounds, pharmaceutically acceptable salts, stereoisomers, or prodrugs with one or more of sodium fluoride, estrogen, a bone anabolic agent, a growth hormone (GH) or growth hormone secretagogue (GHS), a prostaglandin agonist/antagonist, a parathyroid hormone, or prodrugs thereof, or pharmaceutically acceptable salts thereof.

Therapeutically effective amounts of the compounds of formula (I), the pharmaceutically acceptable salts, stereoisomers, and prodrugs thereof, and the pharmaceutically acceptable salts of the stereoisomers and prodrugs, generally embrace any amount sufficient to detectibly modulate ER activity as determined in the assays disclosed hereinbelow, by other activity assays known to one of ordinary skill in the art, or by detecting prevention or alleviation of symptoms in a subject afflicted with an ER-mediated disease, disorder, condition, or symptom.

The diseases, disorders, conditions, or symptoms mediated by ERs, or caused by lowered estrogen levels in mammals, include female sexual dysfunction, perimenopausal or postmenopausal syndrome (particularly hot flashes), osteoporosis, atrophy of skin or vagina, elevated serum cholesterol levels, cardiovascular disease, Alzheimer's disease, reduction or preventing a reduction in cognitive function, an estrogen-dependent cancer, breast or uterine cancer, prostatic disease, benign prostatic hyperplasia (BPH), prostate cancer, obesity, endometriosis, bone loss, uterine fibrosis, aortal smooth muscle cell proliferation, lack of birth control, acne, hirsutism, dysfunctional uterine bleeding, dysmenorrhea, male infertility, impotence, psychological and behavioral symptoms during menstruation, ulcerative mucositis, uterine fibroid disease, restenosis, atherosclerosis, musculoaponeurotic fibromatosis, alopecia, autoimmune disease, cartilage degeneration, delayed puberty, de-myelinating disease, dysmyelinating disease, hypoglycemia, lupus erythematosus, myocardial infarction, ischemia, thromboembolic disorder, obsessive compulsive disorder (OCD), ovarian dysgenesis, post-menopausal CNS disorder, pulmonary hypertension, reperfusion damage, resistant neoplasm, rheumatoid arthritis (RA), seborrhea, sexual precocity, thyroiditis, Turner's syndrome, and hyperlipidemia.

The present methods are also useful for blocking calcium channels, inhibiting environmental estrogens, minimizing the uterotropic effect of tamoxifen, and the analogs thereof, removing fibrin by inhibiting plasminogen activators, inhibiting estrogen-positive primary tumors of the brain and CNS, increasing sphincter competence, increasing libido, inhibiting fertility, oxidizing low-density lipoprotein (LOL), increasing macrophage function, expressing thrombomodulin, and increasing levels of endogenous growth hormone.

The methods of the present invention further comprise administering a compound of formula (I), or a pharmaceutically acceptable salt, stereoisomer, or prodrug thereof, or a pharmaceutically acceptable salt of the stereoisomer or prodrug, in combination with one or more of sodium fluoride, estrogen, a bone anabolic agent, a growth hormone (GH) or growth hormone secretagogue (GHS), a prostaglandin agonist/antagonist, a parathyroid hormone, or prodrugs thereof, or pharmaceutically acceptable salts thereof.

When used in connection with the combination aspect of the present invention, the term "sodium fluoride" refers to the salt sodium fluoride in all of its forms (e.g, slow-release sodium fluoride, sustained-release sodium fluoride, and the like). Sustained-release sodium fluoride, for example, is disclosed in U.S. Pat. No. 4,902,478, the disclosure of which is incorporated herein by reference. The activity of sodium fluoride is readily determined by those skilled in the relevant art according to known protocols. See, for example, E. F. Ericksen, at al., "Bone Histomorphometry", pp. 1–74, Raven Press, New York (1994); S. J. Grier, et al., "The Use of Dual-Energy X-Ray Absorptiometry in Animals", Inv. Radiol., 31(1), pp. 50–62 (1996); and H. W. Wahner, et al., "The Evaluation of Osteoporosis: Dual-Energy X-Ray Absorptiometry in Clinical Practice", pp. 1–296, Martin Dunitz Ltd., London (1994).

Any estrogen may be used in combination with the compounds of formula (I) of the present invention. The term "estrogen", when used in connection with the combination aspect of the present invention, preferably refers to estrogens such as estrone, equilin, estradiene, eqilenin, ethinyl estradiol, 17β-estradiol, 17α-dihydroequilenin, 17β-dihydroequilenin (U.S. Pat. No. 2,834,712), 17α-dihydroequilin, 17β-dihydroequilin, menstranol, conjugated estrogenic hormones, such as those in Premarin® products (Wyeth-Ayerst Laboratories), and the like. Phytoestrogens, such as equol or enterolactone, and esterified estrogens, such as those sold under the tradename Estratab® (Solvay Pharmaceuticals), may also be utilized in the instant combinations. Also useful in the present combinations are estrogen salts. Examples of such estrogen salts include sodium estrone sulfate, sodium equilin sulfate, sodium 17α-dihydroequilin sulfate, sodium 17α-estradiol sulfate, sodium δ8,9-dehydroestrone sulfate, sodium equilin sulfate, sodium 17β-dihydroequilin sulfate, sodium 17β-estradiol sulfate, estrone 3-sodium sulfate, equilin-3-sodium sulfate, 17α-dihydroequilin-3-sodium sulfate, 3β-hydroxy-estra-5(10), 7-dien-17-one-3-sodium sulfate, 5α-pregnan-3β-20R-diol-20-sodium sulfate, 5α-pregnan-3β, 16α-diol-20-one-3-sodium sulfate, δ(8,9)-dehydroestrone-3-sodium sulfate, estra-3β, 17α-diol-3-sodium sulfate, 3β-hydroxy-estr-5(10)-en-17-one-3-sodium sulfate, and 5α-pregnan-3β, 16α,20R-triol-3-sodium sulfate, and the like. Additional estrogens will be known to one of ordinary skill in the relevant art.

Any bone anabolic agent (bone mass augmenting agent) may be used in combination with the compounds of formula (I) of the instant invention. A bone mass augmenting agent is a compound that augments bone mass to a level that is above the bone fracture threshold (as detailed in the World Health Organization Study entitled, "Assessment of Fracture Risk and its Application to Screening for Postmenopausal Osteoporosis (1994). Report of a WHO Study Group. World Health Organization Technical Series 843").

Any growth hormone (GH), or growth hormone secretagogue (GHS) may be employed in combination with the compounds of formula (I) of the instant invention. The term "growth hormone secretagogue" refers to a compound that stimulates the release of growth hormone, or mimics the action of growth hormone (e.g., increases bone formation leading to increased bone mass). Such actions are readily determined by those skilled in the art according to standard assays. A variety of these compounds are disclosed in U.S. Pat. Nos. 5,492,916, 5,492,920, 5,494,919, 5,536,716, 5,622,973 5,652,235, 5,777,112, and 6,107,306, the disclosures of which are incorporated herein by reference; and in PCT International Application Publication Nos. WO 94/19367 and WO95/14666. However, additional GH or GHS's will be known to those skilled in the relevant art. A particularly preferred GHS is the compound MK-677, i.e., N[1-(R)-[1,2-dihydro-1-methanesulfonylspiro[3H-indole-3, 4'piperidin]-1'-yl)carbonyl]-2-(phenylmethyloxy)ethyl]-2-amino-2-methylpropanamide. Other particularly preferred GHS's comprise (i) 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, or the L-tartrate salt thereof; (ii) 2-amino-N-{1-(R)-benzyloxymethyl-2-[3a-(R)-(4-fluoro-benzyl)-2-methyl-3-oxo-2, 3,3a,4,6,7-hexahydro-pyrazolo[4,3-c]pyridin-5-yl]-2-oxo-ethyl}-isobutyramide; (iii) 2-amino-N-[2-(3a-(R)-benzyl-3-oxo-2,3,3a,4,6,7-hexahydro-pyrazolo[4,3-c]pyridin-5-yl)-1-(R)benzyloxymethyl-2-oxo-ethyl]isobutyramide; and (iv) 2-amino-N-{1-(2,4-difluoro-benzyloxymethyl)-2-oxo-2-[3-oxo-3a-pyridin-2-ylmethyl-2-(2,2,2-trifluoro-ethyl)-2,3,3,a, 4,6,7-hexahydro-pyrazolo[4,3-c]pyridin-5-yl]-ethyl}-2-methyl-propionamide. Additional growth hormones and growth hormone secretagogues will be known to one of ordinary skill in the relevant art.

Any prostaglandin agonist/antagonist may be used in combination with the compounds of formula (I) of the instant invention. The term "prostaglandin agonist/antagonist" refers to compounds that bind to prostaglandin receptors and mimic the action of prostaglandin in vivo (e.g., stimulate bone formation and increase bone mass). See, for example, S. An, et al., "Cloning and Expression of the $EP_2$ Subtype of Human Receptors for Prostaglandin $E_2$", Biochem. Biophys. Res. Comm., 197(1), pp. 263–270 (1993). Such actions are readily determined by those skilled in the art according to standard assays. See, for example, E. F. Ericksen, at al., "Bone Histomorphometry", pp. 1–74, Raven Press, New York (1994); S. J. Grier, et al., "The Use of Dual-Energy X-Ray Absorptiometry in Animals", Inv. Radiol., 31(1), pp. 50–62 (1996); and H. W. Wahner, et al., "The Evaluation of Osteoporosis: Dual-Energy X-Ray Absorptiometry in Clinical Practice", pp. 1–296, Martin Dunitz Ltd., London (1994). A variety of prostaglandin agonist/antagonists will be known to one skilled in the relevant art. Exemplary prostaglandin agonists/antagonists are disclosed in the following U.S. patents, the disclosure of which are incorporated herein by reference:

(i) commonly-assigned U.S. Pat. No. 3,932,389 discloses 2-descarboxy-2-(tetrazol-5-yl)-11-desoxy-15-substituted-omega-pentanorprostaglandins useful for bone formation activity;

(ii) commonly-assigned U.S. Pat. Nos. 3,982,016, 4,000, 309, and 4,018,892 disclose 16-aryl-13,14-dihydro-$PGE_2$ p-biphenyl esters useful for bone formation activity;

(iii) commonly-assigned U.S. Pat. Nos. 4,132,847 and 4,219,483 disclose 2,3,6-substituted-4-pyrones useful for bone formation activity;

(iv) U.S. Pat. No. 4,621,100 discloses substituted cyclopentanones useful for bone formation activity;

(v) U.S. Pat. No. 4,216,183 discloses cyclopentanones useful for bone formation activity;

(vi) commonly-assigned U.S. Pat. No. 6,288,120 and PCT International Application Publication No. WO 99/19300 which disclose prostaglandin EP2 agonists useful in preventing bone loss and/or restoring or augmenting bone mass; and (vii) commonly-assigned PCT International Application Publication Nos. WO 2001/46140 and WO 2002/ 042268, which disclose prostaglandin EP4 selective agonists useful in the treatment of conditions presenting with low bone mass.

Any parathyroid hormone may be used in combination with the compounds of formula (I) of the instant invention. The term "parathyroid hormone" refers to parathyroid hormone, fragments or metabolites thereof, and structural analogs thereof, that can stimulate bone formation and/or increase bone mass. Also included are parathyroid hormone-related peptides, and active fragments and analogs of parathyroid-related peptides. See, for example, PCT International Application Publication No. WO 94/01460. Such functional activity is readily determined by those skilled in the art according to standard assays. See, for example, E. F. Ericksen, at al., "Bone Histomorphometry", pp. 1–74, Raven Press, New York (1994); S. J. Grier, et al., "The Use of Dual-Energy X-Ray Absorptiometry in Animals", Inv. Radiol., 31(1), pp. 50–62 (1996); and H. W. Wahner, et al., "The Evaluation of Osteoporosis: Dual-Energy X-Ray Absorptiometry in Clinical Practice", pp. 1–296, Martin Dunitz Ltd., London (1994). Exemplary parathyroid hormones are disclosed in, for example, "Human Parathyroid Peptide Treatment of Vertebral Osteoporosis", Osteoporosis Int., 3 (Supp. 1), pp. 199–203; and "PTH 1-34 Treatment of Osteoporosis with Added Hormone Replacement Therapy: Biochemical, Kinetic and Histological Responses", Osteoporosis Int., 1, pp. 162–170. A variety of parathyroid hormones will be known to one of ordinary skill in the relevant art.

In yet another aspect, the invention provides pharmaceutical compositions comprising a compound for formula (I), or a pharmaceutically acceptable salt, stereoisomer, or prodrug thereof, or a pharmaceutically acceptable salt of the stereoisomer or prodrug, and a pharmaceutically acceptable carrier, vehicle, or diluent. Additionally, the pharmaceutical compositions of the invention may further comprise one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof.

The compounds of formula (I), the pharmaceutically acceptable salts, stereoisomers and prodrugs thereof, and the pharmaceutically acceptable salts of the stereoisomers and prodrugs, may be administered to a subject at dosage levels in the range of from about 0.0001 mg/kg per day to about 200 mg/kg per day, preferably from about 0.01 mg/kg per day to about 100 mg/kg per day. However, some variability in the general dosage range may be required depending upon the age and mass of the subject being treated, the intended route of administration, the particular compound being administered, and the like. The determination of dosage ranges and optimal dosages for a particular subject is within the ability of one of ordinary skill in the art having benefit of the instant disclosure.

In the combination aspect of the instant invention, the dosages of sodium fluoride, estrogen, bone anabolic agents, growth hormones or growth hormone secretagogues, prostaglandin agonists/antagonists, parathyroid hormones, the prodrugs thereof, or pharmaceutically acceptable salts thereof, will also be generally dependent upon a number of factors including the health of the subject being treated, the extent of treatment desired, the nature and kind of concurrent therapy, if any, and the frequency of treatment and the nature of the effect desired.

In general, effective dosage ranges for estrogen are from about 0.001 mg/kg per day to about 20 mg/kg per day.

In general, effective dosage ranges for bone anabolic agents are from about 0.001 mg/kg per day to about 100 mg/kg per day, preferably from about 0.01 mg/kg per day to about 50 mg/kg per day.

In general, effective dosage ranges for growth hormones or growth hormone secretagogues are from about 0.0001 mg/kg per day to about 100 mg/kg per day, preferably from about 0.01 mg/kg per day to about 5 mg/kg per day.

In general, effective dosage ranges for prostaglandin agonists/antagonists are from about 0.001 mg/kg per day to about 50 mg/kg per day.

In general, effective dosage ranges for parathyroid hormones are from about 0.001 mg/kg per day to about 1 mg/kg per day.

Some variability in the above general dosage ranges, however, may be required depending upon the age and body mass of the subject being treated, the intended route of administration, the particular bone anabolic agent(s), growth hormone(s) or growth hormone secretagogue(s), prostaglandin agonist(s)/antagonist(s), parathyroid hormone(s), prodrug(s) thereof, or pharmaceutically acceptable salt(s) thereof being administered, and the like. The determination of dosage ranges and optimal dosages for a particular subject is also well within the ability of one of ordinary skill in the art having benefit of the instant disclosure.

According to the methods of the present invention, a compound of formula (I), or a pharmaceutically acceptable salt, stereoisomer, or prodrug thereof, or a pharmaceutically acceptable salt of the stereoisomer or prodrug; or a compound of formula (I), or a pharmaceutically acceptable salt, stereoisomer, or prodrug thereof, or a pharmaceutically acceptable salt of the stereoisomer or prodrug, and one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof, is administered to a subject in need of treatment therewith, preferably in the form of a pharmaceutical composition. In the combination aspect of the invention, a compound of formula (I), or a pharmaceutically acceptable salt, stereoisomer, or prodrug thereof, or a pharmaceutically acceptable salt of the stereoisomer or prodrug, and one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof, may be administered either separately, or in the preferred pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the present invention, when the compound of formula (I), or the pharmaceutically acceptable salt, stereoisomer, or prodrug thereof, or the pharmaceutically acceptable salt of the stereoisomer or prodrug; or the compound of formula (I), or the pharmaceutically acceptable salt, stereoisomer, or prodrug thereof, or the pharmaceutically acceptable salt of the stereoisomer or prodrug, and one or more of sodium fluoride; estrogen, the bone anabolic agent, the growth hormone or growth hormone secretagogue, the prostaglandin agonist/antagonist, the parathyroid hormone, or prodrug thereof, or pharmaceutically acceptable salt thereof, are administered together, such administration can be sequential in time or simultaneous, with the simultaneous method being generally preferred. For sequential administration, the administration can be in any order. It is generally preferred that the administration be oral. It is especially preferred that the administration be oral and simultaneous. When the administration is sequential, the administration of each may be by the same or by different methods.

According to the methods of the present invention, a compound of formula (I), or a pharmaceutically acceptable salt, stereoisomer, or prodrug thereof, or a pharmaceutically acceptable salt of the stereoisomer or prodrug; or a compound of formula (I), or a pharmaceutically acceptable salt, stereoisomer, or prodrug thereof, or a pharmaceutically acceptable salt of the stereoisomer or prodrug, and one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof, is preferably administered in the form of a pharmaceutical composition comprising a pharmaceutically acceptable carrier, vehicle, or diluent. Accordingly, a compound of formula (I), or a pharmaceutically acceptable salt, stereoisomer, or prodrug thereof, or a pharmaceutically acceptable salt of the stereoisomer or prodrug, and one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof, may be administered to a subject separately or together in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for xeample, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

Since the invention relates to the treatment or prevention of diseases, disorders, conditions, or symptoms mediated by an ER or caused by lowered estrogen levels, using combinations of active ingredients that may be administered separately, the invention further relates to combining separate pharmaceutical compositions in kit form. A kit, according to the invention, comprises: (i) a first unit dosage form comprising an amount of a compound of formula (I), a pharmaceutically acceptable salt, stereoisomer, or prodrug thereof, or a pharmaceutically acceptable salt of said stereoisomer or prodrug; (ii) a second unit dosage form comprising an amount of one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof; and (iii) a container for containing said first and said second unit dosage forms. Preferably, each of the first and second unit dosage forms further comprise a pharmaceutically acceptable carrier, vehicle, or diluent. In the kit aspect of the invention, the container is used to separate the contain separate unit dosage forms and may comprise, for example, a divided bottle, or a divided foil packet, however, the separate unit dosage forms may also be contained within a single, undivided container. Normally, the kit will also include directions for administering the separate components. The kit form is particularly advantageous when the separate components are preferably administered in different dosage forms (e.g., oral and parenteral), are administered at different dosage levels, or when titration of the individual components of the combination is desired by the prescribing physician.

One particular example of such a kit comprises a so-called blister pack. Blister packs are well-known in the packaging industry and are used widely for the packaging of pharmaceutical unit dosage forms (e.g, tablets, capsules, and the like). Blister packs generally comprise a sheet of relatively rigid material covered with a foil of preferably transparent plastic material. During the packaging process, recesses are formed in the plastic foil. The recesses generally conform to the shape and size of the tablets or capsules contained therein. Next, the tablets or capsules are placed in the recesses and sheet of relatively rigid material is sealed against the plastic foil at the face of the foil that is opposite from the direction in which the recesses were formed. As a result, the tablets or capsules are sealed in the recesses between the plastic foil and the sheet. Preferably, the strength of the sheet is such that the tablets or capsules may be removed from the blister pack by the application of manual pressure on the recesses whereby an opening is formed in the sheet at the place of the recess. The tablet or capsule can then be removed through the formed opening.

It is further desirable to provide a memory aid on the pack, e.g., in the form of numbers or similar indicia next to the tablets or capsules whereby the indicia correspond with the days of regimen which the dosage form so specified is to be ingested. An additional example of such a memory aid is a calendar printed on the pack, e.g, as follows: "First Week, Monday, Tuesday, . . . etc. . . . Second Week, Monday, Tuesday, . . . ", etc. Other variations will be readily apparent. A "daily dose" can be a single tablet or capsule or multiple tablets or capsules to be ingested on a given day. Also, a daily dose comprising an amount of a compound of formula (I), a pharmaceutically acceptable salt, stereoisomer, or prodrug thereof, or a pharmaceutically acceptable salt of said steroisomer or prodrug, can consist of one tablet or capsule while a daily dose of comprising an amount of one or more of sodium fluoride, estrogen, a bone anabolic agent, a growth hormone or growth hormone secretagogue, a prostaglandin agonist/antagonist, a parathyroid hormone, or prodrugs thereof, or pharmaceutically acceptable salts thereof can consist of multiple tablets or capsules, or vice versa. The memory aid should reflect this.

In another specific embodiment of the invention, a pack designed to dispense the daily doses of one at a time in the order of their intended use is provided. Preferably, the pack is equipped with a memory aid, so as to further facilitate compliance with the dosage regimen. An example of such a memory aid is a mechanical counter that indicates the number of daily doses to be dispensed. Another example of such a memory aid is a battery-powered microchip memory coupled with a liquid-crystal readout, or audible reminder signal which, for example, reads out the date that the last daily dose has been taken and/or reminds the patient when the next dose is to be taken.

The compounds of formula (I), the pharmaceutically acceptable salts, stereoisomers, and prodrugs thereof, and the pharmaceutically acceptable salts of the stereoisomers and prodrugs, may be prepared according to the exemplary procedures and techniques disclosed in the Examples hereinbelow, as well as by known organic preparative methods. Unless otherwise noted, all reactants and reagents were obtained commercially.

Synthetic Schemes

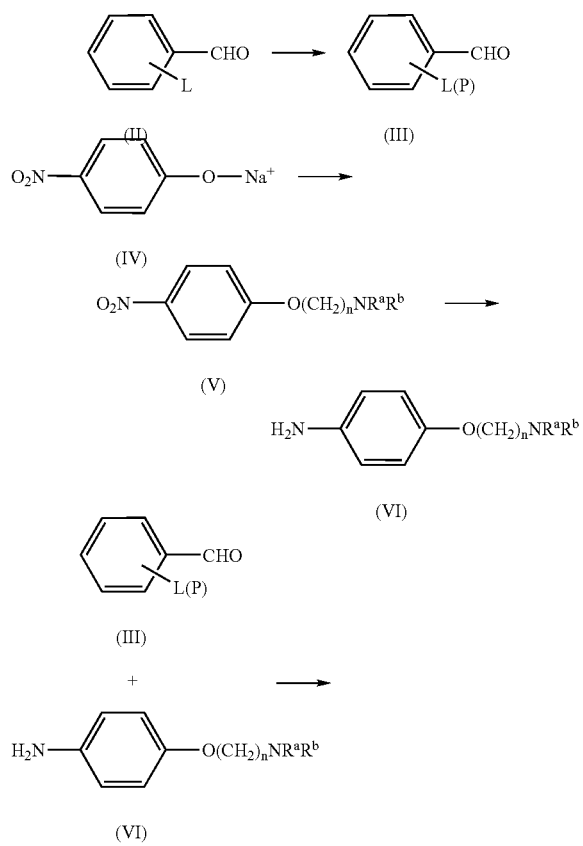

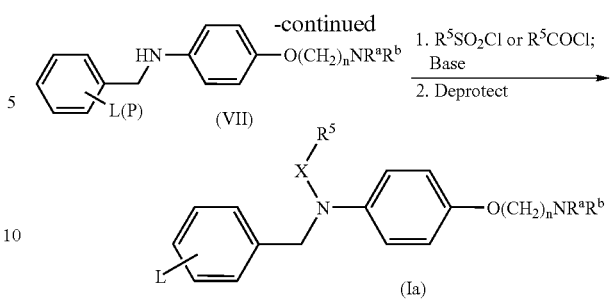

The compounds of formula (Ia), falling under the generic scope of the compounds of formula (I) hereinabove, may be prepared as outlined in Scheme 1.

In Scheme 1, a hydroxy-substituted benzaldehyde derivative (II) is protected to furnish protected aldehyde derivative (III). For matters of illustrative convenience, unless otherwise designated in the instant Schemes, L is intended to be, where chemically appropriate, a generic representation of any, or all, of the three variables $R^1$, $R^2$, and/or $R^3$ in the compounds of formula (I) disclosed herein. With respect to Scheme 1, L preferably represents 4-OH; 2-Cl, 4-OH; 2-OMe, 4-OH; 3-Me, 4-OH; 3-OH; or 2-OH, and n=2. The protection of hydroxy-substituted aldehyde derivative (II) to furnish the protected aldehyde derivative (III) may be effected according to well-known methods. See, for example, T. W. Greene, et al., "Protecting Groups in Organic Synthesis," Second Edition, John Wiley and Sons, Inc., 1981. The —OH component of L is preferably protected as a THP (tetrahydropyranyl) or a Ts (tosylate) derivative. The use of THP as a protecting group for alcohols will be well known to one of ordinary skill in the relevant art. Typically, the —OH group is reacted with 3,4-dihydro-2H-pyran in the presence of a mild acid such as pyridinium p-toluenesulfonate in an aprotic solvent, such as methylene chloride or tetrahydrofuran.

The protected aldehyde derivative (III) is then reductively aminated with amine (VI), which is preferably prepared by O-alkyation of the sodium salt of p-nitrophenol (IV), preferably with a haloalkylamine of the formula $X\text{-}(CH_2)_n\text{—}NR^aR^b$, wherein X is preferably chloro, bromo, or iodo, to provide nitro derivative (V). Reduction of (V) subsequently provides amine (VI). The O-alkylation step is preferably effected by combining (IV), and a haloalkylamine such as 1-(2-chloroethyl)pyrrolidine, in a high-boiling, aprotic solvent such as xylenes or dimethylformamide, along with an inorganic base, such as potassium carbonate, and heating the mixture until the reaction is complete. Alternatively, nitro derivative (V) may be prepared via the so-called Mitsunobu Reaction wherein p-nitrophenol is alkylated in the presence of a coupling agent such as triphenylphosphine/diethyl azodicarboxylate (DEAD), or diisopropyl azodicarboxylate in an inert solvent such as methylene chloride or tetrahydrofuran at a temperature of from about 0° C. to about 80° C. See, for example, O. Mitsunobu, Synthesis, 1, (1981). The nitro derivative (V) may be reduced to amine (VI) according to known methods, for example, by using reagents such as Zn/HCl;Sn/HCl; catalytic hydrogenation in the presence of Raney nickel, palladium, or platinum; and the like. See, for example, P. N. Rylander, "Hydrogenation Methods", Academic Press, New York, N.Y., 1985.

The reductive amination of aldehyde (III) with amine (VI) to afford (VII) may be effected with a hydride reducing agent such as sodium borohydride, sodium cyanoborohydride, or sodium triacetoxyborohydride. The reaction is typically performed in a polar, protic solvent, such as methanol or ethanol, at temperatures of between about −78° C. and about 40° C. See, for example, A. Abdel-Magid, et al., Tetrahedron Lett., 39, 5595–5598 (1990). Other reductive amination conditions involve the use of titanium isopropoxide and sodium cyanoborohydride (R. J. Matteson, J. Org. Chem., 55, 2552–2554 (1990)), or by preformation of an imine intermediate under dehydrating conditions, followed by reduction. With respect to Scheme 1, the reductive amination step is preferably effected by first condensing (III) and (VI) in a solvent such as methylene chloride in the presence of a dehydrating agent, such as magnesium sulfate to preform the imine intermediate. The imine so formed is then reduced, preferably in situ, using sodium borohydride in methanol, ethanol, or a mixture thereof.

Compound (VII) is then reacted with an appropriately $R^5$-substituted acid chloride or sulfonyl chloride to furnish, following O-deprotection, the compounds of formula (Ia), wherein X represents CO or $SO_2$, respectively. The reaction of (VII) with an appropriately $R^5$-substituted acid chloride or sulfonyl chloride is normally effected in an aprotic, non-polar solvent, such as dichloromethane or ether, in the presence of an weak organic base, such as triethylamine, pyridine, or N-methylmorpholine, at a temperature of about –20° C. to about 50° C. Alternatively, the compounds of formula (Ia), may be prepared by coupling amine (VII) with an appropriately-substitued carboxylic or sulfonic acid in the presence of a coupling agent, such as dicyclohexylcarbodiimide (DCC), 1-(3'-dimethylaminopropyl)-3-ethylcarbodiimide (EDC), or 1-propanephosphonic acid cyclic anhydride (PPAA), and a suitable base, such as triethylamine, N,N-dimethylaminopyridine (DMAP), or N-methylmorpholine, in a solvent such as methylene chloride, chloroform, or dimethylformamide at a temperature of about 0° C. to about 10° C. If appropriate, an additive such as 1-hydroxybenzotriazole (HOBT) may also be employed.

The O-deprotection step, where P represents THP, is preferably effected with hydrochloric acid in ethanol, with trifluoroacetic acid, optionally with reagents such as triethylsilane, or, in the instance where P represents Ts, with aqueous sodium hydroxide in methanol. See, for example, T. W. Greene, et al., supra.

The compounds falling within the scope of formula (Ia), numbered 1–149, that were prepared according to the methodologies disclosed in Scheme 1 are set forth in tabular form in Tables 1–5 hereinbelow.

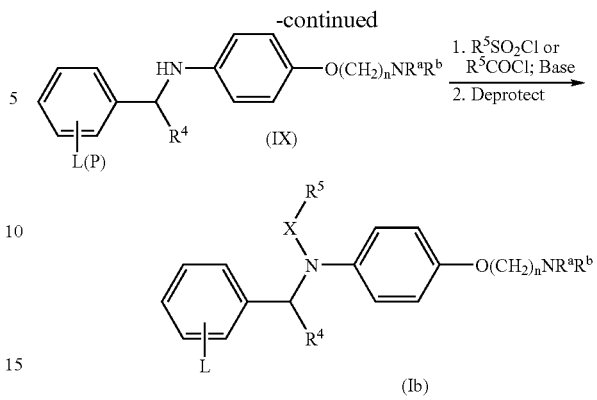

The compounds of formula (Ib) falling under the generic scope of the compounds of formula (I) hereinabove, may be prepared as outlined in Scheme 2.

In Scheme 2, the O-THP protected aldehyde derivative (IIa) is condensed with amine (VI) to afford imine (VII). Such condensation is typically performed in a polar, protic solvent, such as ethanol, at elevated temperature, preferably at the reflux temperature of the particular solvent employed. Alternatively, the condensation may be effected in a non-polar solvent such as dichloromethane in the presence of a dehydrating agent, such as magnesium sulfate.

The imine (VII) so formed is then alkylated, preferably with an alkyllithium derivative, in an aprotic solvent such as tetrahydrofuran, to afford hydroxy-protected amine (IX). N-acylation or N-sulfonylation as described hereinabove in Scheme 1, followed by O-deprotection, also as described hereinabove in Scheme 1, affords the hydroxylated compound of formula (Ib), wherein X represents CO or $SO_2$.

The compounds falling within the scope of formula (Ib), compounds 150–152, that were prepared according to the methodologies disclosed in Scheme 2 are set forth in tabular form in Table 6 hereinbelow.

Scheme 2

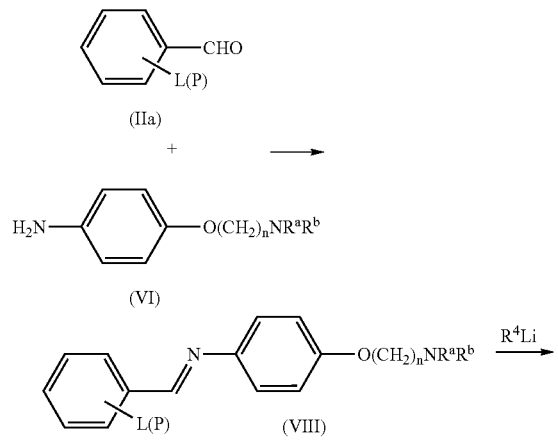

Scheme 3

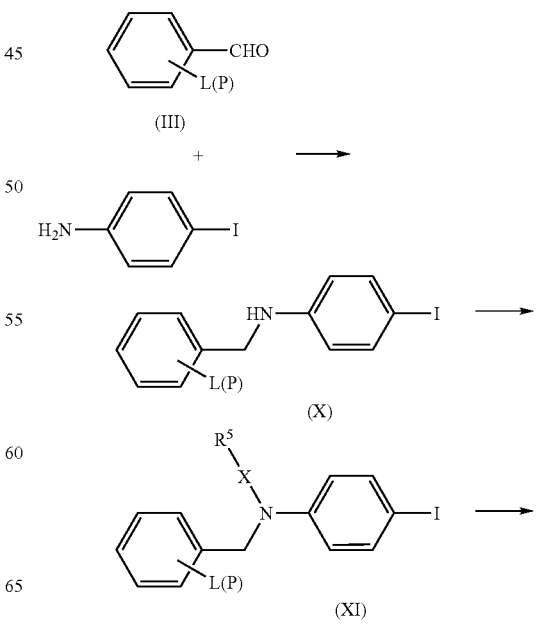

-continued

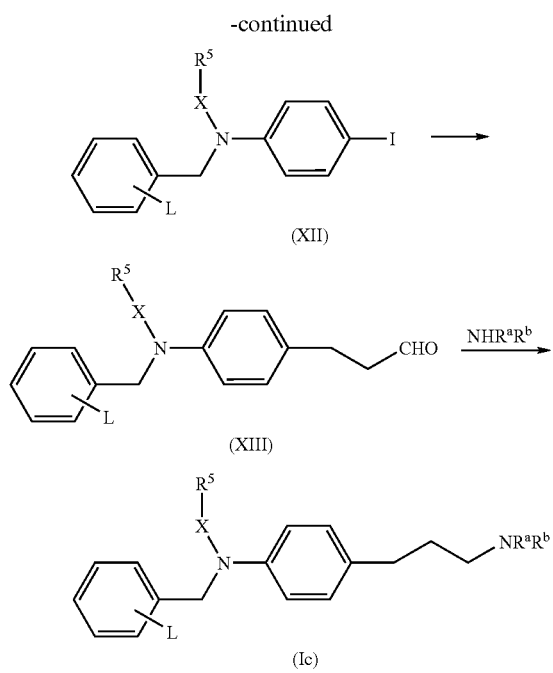

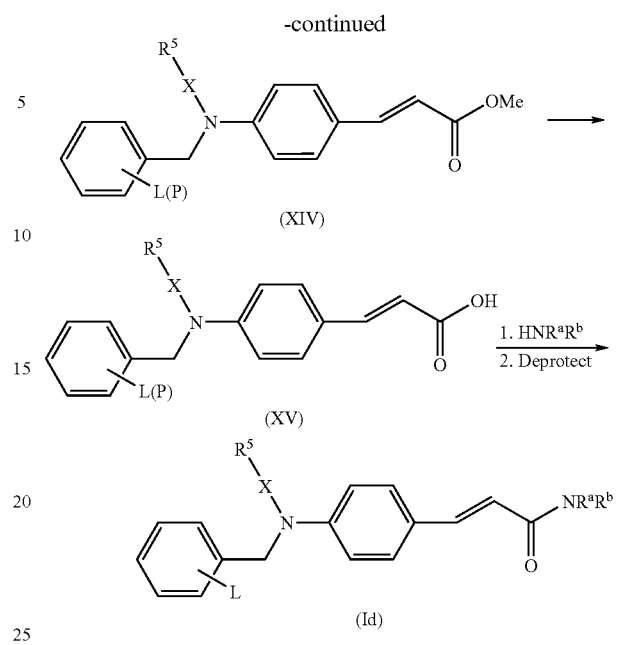

The compounds of formula (Ic) falling under the generic scope of the compounds of formula (I) hereinabove, may be prepared as outlined in Scheme 3.

In Scheme 3, protected aldehyde derivative (III) is reductively aminated with p-iodoaniline to form iodo amine (X). With respect to Scheme 3, L preferably represents 4-OH; 2-Cl, 4-OH; or 3-OH, and P preferably represents a THP protecting group, discussed hereinabove in Scheme 1.

Treatment of iodo amine (X) with an appropriately R⁵-substituted acid chloride, or sulfonyl chloride as described hereinabove in Scheme 1 furnishes iodo compound (XI). Deprotection of (XI), also as described hereinabove in Scheme 1, affords the deprotected compound (XII) which is formylated to provide aldehyde (XIII). The formylation step is preferably effected by the palladium catalyzed Heck Reaction of (XII) and allyl alcohol, followed by in situ isomerization to furnish aldehyde (XIII). Reductive amination of aldehyde (XIII) with an appropriately-substituted amine, according to the methods described hereinabove in Scheme 1, affords the amine compounds of formula (Ic).

The compounds falling within the scope of formula (Ic), compounds 153–190, that were prepared according to the methodologies disclosed in Scheme 3 are set forth in tabular form in Tables 7–9 hereinbelow.

Scheme 4

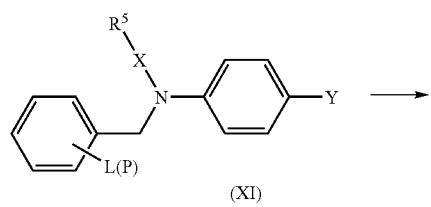

The compounds of formula (Id) falling under the generic scope of the compounds of formula (I) hereinabove, may be prepared as outlined in Scheme 4.

In Scheme 4, compound (XI), wherein Y is an appropriate leaving group, such as Br, I, or -OTf (triflate), is functionalized with acrylic acid methyl ester via the so-called Heck coupling to provide carboxymethylester (XIV). Such functionalization is preferably effected in the presence of a base, such as triethylamine, in a non-polar, aprotic solvent, such as dimethylformamide or acetonitrile, at a temperature of about 0° C. to about 150° C., employing a catalytic amount of a palladium metal catalyst, such as palladium acetate or palladium tetrakistriphenylphosphine. With respect to Scheme 4, L preferably represents 4-OH, or 3-OH, and P represents a THP protecting group.

Saponification of carboxymethylester (XIV) with base affords carboxylic acid (XV), which is then condensed with an appropriately-substituted amine to furnish the amide compounds of formula (Id). The condensation of (XV) with an amine is preferably effected in the presence of a coupling agent, such as 1-propanephosphonic acid cyclic anhydride, a base, such as triethylamine, and catalytic dimethylaminopyridine (DMAP) in an aprotic solvent such as methylene chloride. The O-deprotection step, which may be effected as described hereinabove in Scheme 1, affords the hydroxylated compounds of formula (Id). One of ordinary skill in the relevant art will appreciate that the α,β unsaturated amide intermediate (XIV) and/or compound (Id) may, where desired or appropriate, be reduced to the corresponding saturated analog(s) thereof. Such reductions are typically performed in the presence of a metal catalyst, such as palladium, and a hydrogen-transfer agent, such as ammonium formate. The reduction reaction is normally effected in a reaction-inert solvent, such as methanol, at elevated temperature, normally the reflux temperature of the solvent employed. Alternatively, the reduction reaction may be conducted in the presence of a metallic catalyst, such as palladium, and hydrogen gas in a reactioninert solvent, such as methanol, at ambient temperature. An example of such a reduction is provided hereinbelow in Example 209.

The compounds falling within the scope of formula (Id), compounds 191–200, that were prepared according to the methodologies disclosed in Scheme 4 are set forth in tabular form in Table 10 hereinbelow.

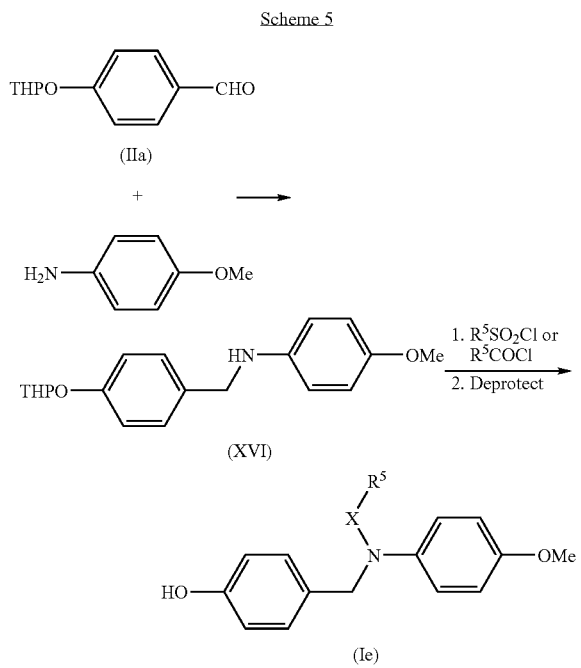

The compounds of formula (Ie) falling under the generic scope of the compounds of formula (I) hereinabove, may be prepared as outlined in Scheme 5.

In Scheme 5 hereinabove, reductive amination of protected aldehyde (IIa) with p-anisidine furnishes protected amine (XVI), which is treated with an appropriately $R^5$-substituted acid chloride or sulfonyl chloride to furnish, following O-deprotection, the hydroxylated compound of formula (Ie), wherein X represents CO or $SO_2$, respectively. The reductive amination of protected aldehyde (IIa) with p-anisidine may be effected according to the methods disclosed hereinabove in Scheme 1. The steps of treating amine (XVI) with the appropriately $R^5$-substituted acid chloride or sulfonyl chloride, and deprotecting the acylated or sulfonylated product thus formed, may also be effected as disclosed hereinabove in Scheme 1.

The compounds falling within the scope of formula (Ie), compounds 201–206, that were prepared according to the methodologies disclosed in Scheme 5 are set forth in tabular format in Table 11 hereinbelow.

PREPARATIVE EXPERIMENTAL

Unless otherwise noted, the following experimental abbreviations have the indicated meanings:
bs—broad singlet
d—doublet
dd—double doublet
dq—double quartet
dt—double triplet
HCl—hydrogen chloride/hydrochloric acid
HPLC—high performance liquid chromatography
hr—hour(s)
Hz—Hertz
J—coupling constant
m—multiplet
mL—milliliter(s)
MS—mass spectrometry
mmol—millimole(s)
NMR—nuclear magnetic resonance
p.s.i.—pounds per square inch
q—quartet
s—singlet
THP—tetrahydropyran(yl)
t—triplet
TLC—thin-layer chromatography
v/v—volume for volume
μl—microliter(s)
μmol—micromole(s)

HPLC reversed-phase purification procedures were performed on a 21×50 mm ODS column employing the solvent mixtures set forth in individual Examples.

Preparations 1 to 8

Intermediates useful in the preparation of the final compounds depicted in Scheme 1 hereinabove, and set forth in Tables 1 to 5 hereinbelow, were prepared as disclosed in Preparations 1 to 8.

Preparation 1

4-(2-Pyrrolidin-1-yl-ethoxy)-phenylamine

Step A: 1-[2-(4-Nitro-phenoxy)-ethyl]-pyrrolidine

Two identical reactions were set up side-by-side as follows. To a mixture of p-nitrophenoxide sodium salt (20.0 g, 124 mmol) and N-(2-chloroethyl)pyrrolidine hydrochloride (21.0 g, 123.5 mmol) was added 300 mL of xylenes followed by potassium carbonate (23.5 g, 170 mmol). The heterogenous mixture was heated under nitrogen at 130° C. overnight. The reaction was diluted with water and 200 mL of ethyl acetate. The layers were separated and the organic layer was washed with saturated aqueous sodium chloride. The aqueous layers were back-extracted with one portion of methylene chloride and the combined organic layers were dried over sodium sulfate, filtered, and concentrated. Silica gel flash chromatography of the combined residues from both reactions (10% methanol/ethyl acetate to 20% methanol/ethyl acetate to 50% methanol/ethyl acetate) afforded 35.22 g (60%) of the title compound of Step A. MS 237.4 $(M+1)^+$ Step B: 4-(2-Pyrrolidin-1-yl-ethoxy)-phenylamine Two identical reactions were set up side-by-side as follows. To a mixture of 1-[2-(4-nitro-phenoxy)-ethyl]-pyrrolidine (17.61 g, 74.5 mmol) and 5% palladium on carbon (2.0 g) was added 125 mL of ethyl acetate. The reaction mixture was hydrogenated at 45 psi at room temperature for 3 hr. The mixture was filtered through diatomaceous earth under nitrogen, and the filter cake was washed with ethyl acetate and methanol. The combined filtrates from both reactions were concentrated to yield 30.46 g (99%) of the title compound. MS 207.2 $(M+1)^+$ Preparation 2

Toluene-4-sulfonic 4-{[4-(2-pyrrolidin-1-yl-ethoxy)-phenylamino]-methyl}-phenyl ester Step A: Toluene-4-sulfonic acid 4-formyl-phenyl ester To a solution of 4-hydroxybenzaldehyde (5.93 g, 48.56 mmol) and triethylamine (10 mL) in 50 mL of dichloromethane was added tosyl chloride (11.8 g, 61.89 mmol). The reaction mixture was stirred at room temperature for 24 hr. The reaction mixture was diluted with water, acidified with 1 N HCl, and extracted into methylene chloride. The organic layer was separated, dried over magnesium sulfate, and concentrated. The residue was purified by silica gel chromatography (9:1 hexanes:ethyl acetate to 5:1 hexanes: ethyl acetate) to afford 9.50 g (71%) of the title compound of Step A. $^1$HNMR (CDCl$_3$): δ 9.81 (s, 1H), 7.69 (d, 2H, J=8.8 Hz), 7.57 (d, 2H, J=8.4 Hz), 7.19 (d, 2H, J=8.4 Hz), 7.03 (d, 2H, J=8.4 Hz), and 2.28 (s, 3H).

Step B: Toluene-4-sulfonic 4-{[4-(2-pyrrolidin-1-yl-ethoxy)-phenylamino]-methyl}-phenyl ester A solution of toluene-4-sulfonic acid 4-formyl-phenyl ester (3.28 g, 11.88 mmol) and 4-(2-pyrrolidin-1-yl-ethoxy)-phenylamine (2.45 g, 11.88 mol) in 40 mL of methanol was stirred at room temperature overnight. The reaction mixture was concentrated to dryness. A portion of the crude residue (1.36 g, ~2.92 mmol) was dissolved in 35 mL of ethanol and was treated with sodium borohydride (0.687 g, 18.16 mmols), which was added in portions over a period of about 3 hr. The reaction was stirred at room temperature overnight at which time it was concentrated to one-half of its original volume. To this mixture was added 25 mL of water and 25 mL of saturated sodium bicarbonate. The mixture was extracted three times with methylene chloride and the combined organic layers were dried (magnesium sulfate), filtered, and concentrated. Medium pressure silica gel chromatography of the residue (2% methanol/methylene chloride to 10% methanol/methylene chloride) afforded 1.06 g (80%) of the title compound. MS 467.1 (M+1)$^+$ Preparation 3

[4-(2-Pyrrolidin-1-yl-ethoxy)-phenyl]-[4-(tetrahydro-pyran-2-yloxy)-benzyl]-amine Step A: 4-(Tetrahydro-pyran-2-yloxy)-benzaldehyde To 4-hydroxybenzaldehyde (10.0 g, 81.89 mmol) was added 175 mL methylene chloride, 3,4-dihydro-2H-pyran (18.7 mL, 204.97 mmol) and pyridinium p-toluenesulfonate (2.06 g, 8.2 mmol). The reaction mixture was stirred at room temperature for three days. The reaction mixture was partitioned between methylene chloride and saturated aqueous sodium bicarbonate. The layers were separated and the aqueous layer was extracted with a second portion of methylene chloride. The combined organic layers were washed with saturated aqueous sodium chloride, which was then back-extracted with methylene chloride. The combined organic layers were dried over sodium sulfate, filtered, and concentrated. Silica gel flash chromatography of the residue (10% ether/hexanes to 20% ether/hexanes) afforded 17.32 g of the title compound of Step A. MS 207.4 (M+1)$^+$ Step B: [4-(2-Pyrrolidin-1-yl-ethoxy)-phenyl]-[4-(tetrahydro-pyran-2-yloxy)-benzyl]-amine To a solution of 4-(2-pyrrolidin-1-yl-ethoxy)-phenylamine (6.92 g, 33.5 mmol) and 4-(tetrahydro-pyran-2-yloxy)-benzaldehyde (7.25 g, 35.2 mmol) in 110 mL methylene chloride was added magnesium sulfate (14.2 g, 117.3 mmol). The reaction mixture was stirred overnight under nitrogen at room temperature. The reaction mixture was filtered and concentrated. The resulting solid was dissolved in 80 mL ethanol and 40 mL methanol and was treated with sodium borohydride (7.99 g, 211.1 mmol) which was added in portions over a period of 1 hr. The reaction was stirred overnight at room temperature at which time it was concentrated to one-half of its original volume. To this mixture was added 75 mL water and 75 mL saturated aqueous sodium bicarbonate. The mixture was extracted with methylene chloride and the organic layer was washed with water, dried (magnesium sulfate), filtered, and concentrated. Silica gel flash chromatography of the residue (methylene chloride to 10% methanol/methylene chloride) afforded 8.80 g (66%) of the title compound. MS 397.2 (M+1)$^+$ Preparation 4

[2-Chloro-4-(tetrahydro-pyran-2-yloxy-benzyl]-[4-(2-pyrrolidin-1-yl-ethoxy)-phenyl]-amine Step A: 2-Chloro-4-(tetrahydro-pyran-2-yloxy)-benzaldehyde To a solution of 2-chloro-4-hydroxybenzaldehyde (12.0 g, 76.64 mmol) in 175 mL methylene chloride and 10 mL tetrahydrofuran was added 3,4-dihydro-2H-pyran (17.5 mL, 191.6 mmol) and pyridinium p-toluenesulfonate (1.93 g, 7.66 mmol). The reaction mixture was stirred at room temperature for 4 days. Additional 3,4-dihydro-2H-pyran (17.0 mL, 186.3 mmol) and pyridinium p-toluenesulfonate (1.85 g, 7.36 mmol) were added, followed by 5A molecular sieves, and the reaction mixture continued to stir at room temperature for 3 days. Saturated aqueous sodium bicarbonate and water were added. The layers were separated and the aqueous layer was extracted with a second portion of methylene chloride. The combined organic layers were dried (sodium sulfate), filtered, and concentrated. Silica gel flash chromatography of the residue (20% ethyl acetate/hexanes to 50% ethyl acetate/hexanes) afforded 13.37 g (72%) of the title compound of Step A. MS 241.0 (M+1)$^+$ Step B: [2-Chloro-4-(tetrahydro-pyran-2-yloxy)-benzyl]-[4-(2-pyrrolidin-1-yl-ethoxy)-phenyl]-amine To a solution of 2-chloro-4-(tetrahydro-pyran-2-yloxy)-benzaldehyde (1.68 g, 6.97 mmol) and 4-(2-pyrrolidin-1-yl-ethoxy)-phenylamine (1.37 g, 6.64 mmol) in 25 mL methylene chloride was added magnesium sulfate (2.81 g, 23.3 mmol). The reaction mixture was stirred under nitrogen at room temperature overnight, then was filtered, and concentrated. The residue was dissolved in 25 mL of 2:1 (v/v) ethanol:methanol and was treated with sodium borohydride (1.51 g, 39.84 mmol) in portions added over 1 hr. The reaction mixture was stirred at room temperature for 2 hr. at which time it was concentrated to one-half of its original volume. To this mixture was added 25 mL water and 25 mL saturated aqueous sodium bicarbonate. The mixture was extracted with methylene chloride and the organic layer was dried (magnesium sulfate), filtered, and concentrated. Medium pressure silica gel chromatography of the residue (methylene chloride to 10% methanol/methylene chloride) afforded 2.04 g (71%) of the title compound. MS 431.1 (M+1)$^+$ Preparation 5

[2-Methoxy-4-(tetrahydro-pyran-2-yloxy)-benzyl]-[4-(2-pyrrolidin-1-yl-ethoxy)-phenyl]-amine Step A: 2-Methoxy-4-(tetrahydro-pyran-2-yloxy)-benzaldehyde To a solution of 2-methoxy-4-hydroxy-benzaldehyde (2.40 g, 15.8 mmol) and 3,4-dihydro-2H-pyran (3.6 mL, 39.5 mmol) in 50 mL methylene chloride was added pyridinium p-toluenesulfonate (0.397 g, 1.58 mmol). The reaction mixture was stirred at room temperature overnight at which time the reaction was concentrated to one-half its original volume. The layers were separated and the organic layer was washed with saturated aqueous sodium bicarbonate and water. The organic layer was dried (magnesium sulfate), filtered, and concentrated. Medium pressure silica gel chromatography of the residue (5% ethyl acetate/hexanes) afforded 2.13 g (58%) of the title compound of Step A. MS 152.9 (M+1-THP)$^+$ Step B: [2-Methoxy-4-(tetrahydro-pyran-2-yloxy)-benzyl]-[4-(2-pyrrolidin-1-yl-ethoxy)-phenyl]-amine To a solution of 2-methoxy-4-(tetrahydro-pyran-2-yloxy)-benzaldehyde (1.62 g, 6.84 mmol) and 4-(2-pyrrolidin-1-yl-ethoxy)-phenylamine (1.345 g, 6.51 mmol) in 25 mL methylene chloride was added magnesium sulfate (2.74 g, 22.8 mmol). The reaction mixture was stirred at room temperature overnight, then was filtered and concentrated. The residue was dissolved in 25 mL of 2:1 (v/v) ethanol: methanol and was treated with sodium borohydride (1.48 g, 39.1 mmol) in portions added over 1 hr. The reaction mixture was stirred at room temperature for 2 hr. at which time it was concentrated to one-half of its original volume. To this mixture was added 25 mL water and 25 mL saturated aqueous sodium bicarbonate. The mixture was extracted with methylene chloride and the organic layer was dried (magnesium sulfate), filtered, and concentrated. Medium pressure silica gel chromatography of the residue (methylene chloride to 10% methanol/methylene chloride) afforded 1.225 g (47%) of the title compound. MS 427.2 (M+1)$^+$ Preparation 6

[3-Methyl-4-(tetrahydro-pyran-2-yloxy)-benzyl]-[4-(2-pyrrolidin-1-yl-ethoxy)-phenyl]-amine Step A: 3-Methyl-4-(tetrahydro-pyran-2-yloxy)-benzaldehyde To a solution of 4-hydroxy-3-methylbenzaldehyde (3.0 g, 22.03 mmol) in 45 mL methylene chloride was added 3,4-dihydro-2H-pyran (5.0 mL, 54.8 mmol) and pyridinium p-toluenesulfonate (0.55 g, 2.19 mmol). The reaction mixture was stirred at room temperature overnight. The reaction mixture was partitioned between methylene chloride and saturated aqueous sodium bicarbonate. The layers were separated and the aqueous layer was extracted with three portions of methylene chloride. The combined organic layers were washed with saturated aqueous sodium chloride, dried (sodium sulfate), filtered, and concentrated. Silica gel flash chromatography of the residue (10% ether/hexanes to 20% ether/hexanes) afforded 4.35 g of the title compound of Step A. MS 221.1 (M+1)$^+$ Step B: [3-Methyl-4-(tetrahydro-pyran-2-yloxy)-benzyl]-[4-(2-pyrrolidin-1-yl-ethoxy)-phenyl]-amine To a solution of 3-methyl-4-(tetrahydro-pyran-2-yloxy)-benzaldehyde (0.700 g, 3.18 mmol) and 4-(2-pyrrolidin-1-yl-ethoxy)-phenylamine (0.624 g, 3.02 mmol) in 20 mL methylene chloride was added magnesium sulfate (1.82 g, 15.12 mmol). The reaction mixture was stirred overnight at room temperature. The reaction mixture was filtered and concentrated. The residue was redissolved in 20 mL methylene chloride and was treated with magnesium sulfate (1.82 g, 15.12 mmol). The reaction was again stirred overnight at room temperature. The reaction was filtered and concentrated. The residue was again redissolved in 20 mL methylene chloride and was treated with magnesium sulfate (1.82 g, 15.12 mmol). The reaction was once again stirred overnight at room temperature. The reaction was filtered and concentrated. The resulting oil was dissolved in 12 mL ethanol and 6 mL methanol and was treated with sodium borohyride (0.560 g, 14.80 mmol) which was added in two portions over a period of 1 hr. The reaction was stirred at room temperature for 4 days at which time the solvent was removed in vacuo. To the residue was added water, and the mixture was extracted three times with methylene chloride. The combined organic layers were washed with saturated aqueous sodium chloride, dried (sodium sulfate), filtered, and concentrated to afford 1.46 g of the title compound. MS 411.4 (M+1)$^+$ Preparation 7

[4-(2-pyrrolidin-1-yl-ethoxy)-phenyl]-[3-(tetrahydro-pyran-2-yloxy)-benzyl]-amine Step A: 3-(Tetrahydro-pyran-2-yloxy)-benzaldehyde To a solution of 3-hydroxy-benzaldehyde (6.51 g, 53.3 mmol) and 3,4-dihydro-2H-pyran (7.3 mL, 80.0 mmol) in 150 mL methylene chloride was added pyridinium p-toluenesulfonate (1.34 g, 5.33 mmol). The reaction mixture was stirred at room temperature overnight. The layers were separated and the organic layer was washed with saturated aqueous sodium bicarbonate. The organic layer was dried (magnesium sulfate), filtered, and concentrated. Medium pressure silica gel chromatography of the residue (5% ethyl acetate/hexanes to 10% ethyl acetate/hexanes) aforded 10.34 g (94%) of the title compound of Step A.

Step B: [4-(2-Pyrrolidin-1-yl-ethoxy)-phenyl]-[3-(tetrahydro-pyran-2-yloxy)-benzyl]-amine To a solution of 4-(2-pyrrolidin-1-yl-ethoxy)-phenylamine (1.92 g, 9.30 mmol) and 3-(tetrahydro-pyran-2-yloxy)-benzaldehyde (2.01 g, 9.76 mmol) in 35 mL methylene chloride was added magnesium sulfate (3.91 g, 32.5 mmol). The reaction mixture was stirred overnight under nitrogen at room temperature. The reaction mixture was filtered and concentrated. The residue was resuspended in 40 mL of 2:1 ethanol:methanol and was treated with sodium borohydride (1.76 g, 46.5 mmol) which was added in portions at room temperature over a period of 1 hr. The reaction was stirred at room temperature overnight. To this mixture was added water and saturated aqueous sodium bicarbonate. The mixture was extracted with methylene chloride and the organic layer was dried (magnesium sulfate), filtered, and concentrated. Medium pressure silica gel chromatography of the residue (methylene chloride to 10% methanol/methylene chloride) afforded 2.34 g (64%) of the title compound. MS 397.2 (M+1)$^+$ Preparation 8

[4-(2-Pyrrolidin-1-yl-ethoxy)-phenyl]-[2-(tetrahydro-pyran-2-yloxy)-benzyl]-amine Step A: 2-(Tetrahydro-pyran-2-yloxy)-benzaldehyde To salicylaldehyde (2.35 mL, 22.05 mmol) was added 45 mL methylene chloride, 3,4-dihydro-2H-pyran (5.0 mL, 54.8 mmol) and pyridinium p-toluenesulfonate (0.55 g, 2.19 mmol). The reaction mixture was allowed to stir at room temperature overnight. Additional pyridinium p-toluenesulfonate (0.55 g, 2.19 mmol) was added and the reaction mixture was stirred at room temperature for 4 days. The reaction mixture was poured into saturated aqueous sodium bicarbonate. The layers were separated and the aqueous layer was extracted with two portions of methylene chloride. The combined organic layers were washed with saturated aqueous sodium chloride, dried (sodium sulfate), filtered, and concentrated to afford 2.96 g of an inseparable 60:40 mixture of salicylaldehyde and the title compound of Step A.

Step B: [4-(2-Pyrrolidin-1-yl-ethoxy)-phenyl]-[2-(tetrahydro-pyran-2-yloxy)-benzyl]-amine To a solution of the crude 2-(tetrahydro-pyran-2-yloxy)-benzaldehyde (1.325 g, 6.42 mmol maximum) and 4-(2-pyrrolidin-1-yl-ethoxy)-phenylamine (1.25 g, 6.06 mmol) in 40 mL methylene chloride was added NaB(OAc)$_3$H (6.76 g, 31.9 mmol) and glacial acetic acid (0.75 mL, 13.05 mmol). The reaction mixture was stirred at room temperature. The solvent was removed in vacuo and the residue was purified via silica gel flash chromatography (10% methanol/methylene chloride to 20% methanol/methylene chloride) to afford 1.09 g of an inseparable mixture of 2-{[4-(2-pyrrolidin-1-yl-ethoxy)-phenylamino]-methyl}-phenol and the title compound. MS 397.5 (M+1)$^+$

EXAMPLES 1 TO 61

The compounds of the general structure

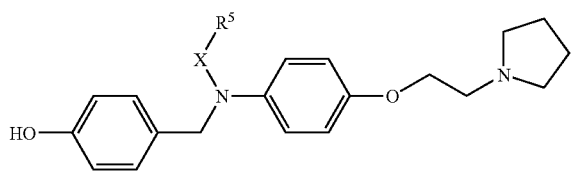

prepared according to the methods depicted in Scheme 1 hereinabove, and set forth in Table 1 hereinbelow, were prepared as disclosed in the following Examples 1 to 61.

Example 1

Cyclohexanecarboxylic acid (4-hydroxy-benzyl)-[4-(2-pyrrolidin-1-yl-ethoxy)-phenyl]-amide Step A: Toluene-4-sulfonic acid 4-({cyclohexanecarbonyl-[4-(2-pyrrolidin-1-yl-ethoxy)-phenyl]-amino}-methyl)-phenyl ester To a solution of toluene-4-sulfonic acid 4-{[4-(2-pyrrolidin-1-yl-ethoxy)-phenylamino]-methyl}-phenyl ester (0.120 g, 0.26 mmol) and triethylamine (0.18 mL, 1.36 mmol) in 2 mL methylene chloride was added cyclohexanecarbonyl chloride (0.138 mL, 1.03 mmol). The reaction mixture was stirred for 3 hr. at room temperature. Saturated aqueous sodium bicarbonate was added and the layers were separated. The aqueous layer was washed with an additional 2 mL of methylene chloride. The combined organic layers were dried (magnesium sulfate), filtered, and concentrated. Flash filter chromatography afforded the title compound of Step A. MS 577.1 (M+1)$^+$ Step B: Cyclohexanecarboxylic acid (4-hydroxy-benzyl)-[4-(2-pyrrolidin-1-yl-ethoxy)-phenyl]-amide To a solution of toluene-4-sulfonic acid 4-({cyclohexanecarbonyl-[4-(2-pyrrolidin-1-yl-ethoxy)-phenyl]-amino}-methyl)-phenyl ester in 5 mL methanol was added 5N NaOH (0.50 mL). The reaction mixture was heated at reflux until complete as judged by TLC and MS. The reaction mixture was washed with methylene chloride. The organic layer was concentrated to afford 0.045 g (41%) of the title compound. MS 423.2 (M+1)$^+$ Example 2

Cyclohexanecarboxylic acid (4-hydroxy-benzyl)-[4-(2-pyrrolidin-1-yl-ethoxy)-phenyl]-amide hydrochloride salt Step A: Cyclohexanecarboxylic acid [4-(2-pyrrolidin-1-yl-ethoxy)-phenyl]-[4-(tetrahydro-pyran-2-yloxy)-benzyl]-amide To a solution of [4-(2-pyrrolidin-1-yl-ethoxy)-phenyl]-[4-(tetrahydro-pyran-2-yloxy)-benzyl]-amine (1.70 g, 4.29 mmol) and triethylamine (2.40 mL, 17.2 mmol) in methylene chloride (8–10 mL) at 0° C. was added cyclohexanecarbonyl chloride (1.72 mL, 12.87 mmol) in methylene chloride (30 mL) dropwise. The reaction mixture was stirred for 1 hr. and was quenched with water/saturated sodium bicarbonate (1/1, 40–50 mL). The layers were separated and the aqueous solution was washed with methylene chloride (2×25 mL). The combined organic solutions were dried (magnesium sulfate), filtered, and concentrated. Medium pressure chromatography using a solvent gradient (methylene chloride to 10% methanol/methylene chloride) afforded the title compound of Step A. MS 507 (M+1)$^+$ Step B: Cyclohexanecarboxylic acid (4-hydroxy-benzyl)-[4-(2-pyrrolidin-1-yl-ethoxy)-phenyl]-amide A mixture of cyclohexanecarboxylic acid [4-(2-pyrrolidin-1-yl-ethoxy)-phenyl]-[4-(tetrahydro-pyran-2-yloxy)-benzyl]-amide (1.64 g, 3.24 mmol), pyridinium p-toluenesulfonate (85 mg, 0.32 mmmol) and ethanol (30 mL) was stirred at room temperature for 24 hr. Aqueous 1N HCl (10 mL) was added and the reaction was stirred for 3–4 hr. The reaction mixture was concentrated to 1/3 the volume and saturated aqueous sodium bicarbonate was added. The aqueous solution was washed with methylene chloride and the organic solution was dried (magnesium sulfate), filtered, and concentrated. Medium pressure chromatography using a solvent gradient (3% methanol in methylene chloride to 15% methanol in methylene chloride) provided the title compound as a white solid (1.16 g). The solid was suspended in methanol (15 mL) and 1.4 mL of 4N HCl in dioxane was added dropwise. The reaction was stirred at room temperature for 0.5 hr. and was concentrated to provide the title compound as the hydrochloride salt. MS 423.2 (M+1)$^+$ Example 3

N-(4-Hydroxy-benzyl)-3,3-dimethyl-N-[4-(2-pyrrolidin-1-yl-ethoxy)-phenyl]-butyramide Prepared in a manner analogous to that described in Example 1. MS 411.2 (M+1)$^+$ Example 4

N-(4-Hydroxy-benzyl)-3-phenyl-N-[4-(2-pyrrolidin-1-yl-ethoxy)-phenyl]-propionamide, trifluoroacetate salt Step A: 3-Phenyl-N-[4-(2-pyrrolidin-1-yl-ethoxy)-phenyl]-N-[4-(tetrahydro-pyran-2-yloxy)-benzyl]-propionamide To a solution of [4-(2-pyrrolidin-1-yl-ethoxy)-phenyl]-[4-(tetrahydro-pyran-2-yloxy)-benzyl]-amine (0.125 g, 0.34 mmol) and triethylamine (0.18 mL, 1.36 mmol) in 2 mL methylene chloride was added hydrocinnamoyl chloride (0.152 mL, 1.02 mmol), dropwise. The reaction mixture was stirred for 1 hr. at room temperature. Saturated aqueous sodium bicarbonate was added and the layers were separated. The aqueous layer was washed with an additional 2 mL of methylene chloride. The combined organic layers were concentrated to give the title compound of Step A. MS 529.2 (M+1)$^+$ Step B: N-(4-Hydroxy-benzyl)-3-phenyl-N-[4-(2-Dyrrolidin-1-yl-ethoxy)-phenyl]-propionamide, trifluoroacetate salt The crude 3-phenyl-N-[4-(2-pyrrolidin-1-yl-ethoxy)-phenyl]-N-[4-(tetrahydro-pyran-2-yloxy)-benzyl]-propionamide prepared in Step A was suspended in 2 mL of a 3:1 (v/v) mixture of ethanol:1N HCl and was stirred at room temperature for 24 hr. An additional 1 mL of 1N HCl was added and the reaction was stirred at room temperature for 24 hr. The reaction mixture was quenched with saturated aqueous sodium bicarbonate and was washed with two portions of methylene chloride. The combined organic layers were concentrated. The residue was purified by reverse phase HPLC (98:2 water:0.1% trifluoroacetic acid to 98:2 acetonitrile:water) to afford the title compound. MS 445.2 (M+1)$^+$ Example 5

Cyclopropanecarboxylic acid (4-hydroxy-benzyl)-[4-(2-pyrrolidin-1-yl-ethoxy)-phenyl]-amide, trifluoroacetate salt Prepared in a manner analogous to that described in Example 4. MS 381.2 (M+1)$^+$ Example 6

2-Ethyl-N-(4-hydroxy-benzyl)-N-[4-(2-pyrrolidin-1-yl-ethoxy)-phenyl]-butyramide, trifluoroacetate salt Prepared in a manner analogous to that described in Example 4. MS 411.3 (M+1)$^+$ Example 7

Cyclopentanecarboxylic acid (4-hydroxy-benzyl)-[4-(2-pyrrolidin-1-yl-ethoxy)-phenyl]-amide, trifluoroacetate salt Prepared in a manner analogous to that described in Example 4. MS 409.2 (M+1)$^+$ Example 8

Cyclohex-3-enecarboxylic acid (4-hydroxy-benzyl)-[4-(2-pyrrolidin-1-yl-ethoxy)-phenyl]-amide, trifluoroacetate salt Prepared in a manner analogous to that described in Example 4. MS 421.2 (M+1)$^+$ Example 9

N-(4-Hydroxy-benzyl)-N-[4-(2-pyrrolidin-1-yl-ethoxy)-phenyl]-benzenesulfonamide, trifluoroacetate salt Step A: N-[4-(2-Pyrrolidin-1-yl-ethoxy)-phenyl]-N-[4-(tetrahydro-pyran-2-yloxy)-benzyl]-benzenesulfonamide To a solution of (4-(2-pyrrolidin-1-yl-ethoxy)-phenyl)-[4-(tetrahydro-pyran-2-yloxy)-benzyl]-amine (117 mg, 0.295 mmol) and pyridine (0.1 mL) in 2 mL methylene chloride was added benzenesulfonyl chloride (0.113 mL, 0.885 mmol) dropwise. The reaction mixture was stirred for 2 hr. at room temperature. Saturated aqueous sodium bicarbonate was added and the layers were separated. The aqueous layer was washed with an additional 1–2 mL of methylene chloride. The combined organic layers were concentrated to give the title compound of Step A.

Step B: N-(4-Hydroxy-benzyl)-N-[4-(2-pyrrolidin-1-yl-ethoxy)-phenyl]-benzenesulfonamide trifluoroacetate salt The crude N-[4-(2-pyrrolidin-1-yl-ethoxy)-phenyl]-N-[4-(tetrahydro-pyran-2-yloxy)-benzyl]-benzenesulfonamide prepared in Step A was suspended in 2 mL of a 3:1 (v/v) mixture of ethanol:1N HCl and was stirred at room temperature for 24 hr.

The reaction mixture was quenched with saturated aqueous sodium bicarbonate and was washed with two portions of methylene chloride. The combined organic layers were concentrated. The residue was purified by reverse phase HPLC (98:2 H$_2$O:0.1% trifluoroacetic acid to 98:2 acetonitrile:water) to yield the title compound. MS 453.1 (M+1)$^+$ Example 10

N-(4-Hydroxy-benzyl)-4-methyl-N-[4-(2-pyrrolidin-1-yl-ethoxy)-phenyl]-benzenesulfonamide, trifluoroacetate salt Prepared in a manner analogous to that described in Example 9. MS 467.1 (M+1)$^+$ Example 11

N-(4-Hydroxy-benzyl)-C-phenyl-N-[4-(2-pyrrolidin-1-yl-ethoxy)-phenyl]-methanesulfonamide, trifluoroacetate salt Prepared in a manner analogous to that described in Example 9. MS 467.1 (M+1)$^+$ Example 12

Propane-2-sulfonic acid (4-hydroxy-benzyl)-[4-(2-pyrrolidin-1-yl-ethoxy)-phenyl]-amide, trifluoroacetate salt Prepared in a manner anaogous to that described in Example 9. MS 419.1 (M+1)$^+$ Example 13

2-Phenyl-ethenesulfonic acid (4-hydroxy-benzyl)-[4-(2-pyrrolidin-1-yl-ethoxy)-phenyl]-amide, trifluoroacetate salt Prepared in a manner analogous to that described in Example 9. MS 479.1 (M+1)$^+$ Example 14

Naphthalene-2-sulfonic acid (4-hydroxy-benzyl)-[4-(2-pyrrolidin-1-yl-ethoxy)-phenyl]-amide, trifluoroacetate salt Prepared in a manner analogous to that described in Example 9. MS 503.1 (M+1)$^+$

Example 15

2-Naphthalen-1-yl-ethanesulfonic acid (4-hydroxy-benzyl)-[4-(2-pyrrolidin-1-yl-ethoxy)-phenyl]-amide, trifluoroacetate salt Prepared in a manner analogous to that described in Example 9. MS 531.1 $(M+1)^+$

Example 16

N-(4-Hydroxy-benzyl)-4-methoxy-N-[4-(2-pyrrolidin-1-yl-ethoxy)-phenyl]-benzenesulfonamide, trifluoroacetate salt Prepared in a manner analogous to that described in Example 9. MS 483.1 $(M+1)^+$

Example 17

Quinoline-8-sulfonic acid (4-hydroxy-benzyl)-[4-(2-pyrrolidin-1-yl-ethoxy)-phenyl]-amide, trifluoroacetate salt Prepared in a manner analogous to that described in Example 9. MS 504.1 $(M+1)^+$

Example 18

N-(4-Hydroxy-benzyl)-4-methoxy-N-[4-(2-pyrrolidin-1-yl-ethoxy)-phenyl]-benzenesulfonamide, hydrochloride salt Step A: 4-methoxy-N-[4-(2-pyrrolidin-1-yl-ethoxy)-phenyl]-N-[4-(tetrahydro-pyran-2-yloxy)-benzyl]-benzenesulfonamide To a solution of [4-(2-pyrrolidin-1-yl-ethoxy)-phenyl]-[4-(tetrahydro-pyran-2-yloxy)-benzyl]-amine (1.40 g, 3.53 mmol) and triethylamine (1.48 mL, 10.59 mmol) in methylene chloride (35 mL) was added 4-methoxy-benzenesulfonyl chloride (1.46 g, 7.06 mmol) in three portions over 15 minutes. The reaction mixture was stirred at room temperature for 24 hr. The reaction mixture was quenched with saturated sodium bicarbonate and the aqueous solution was washed with methylene chloride. The combined organic solutions were dried (magnesium sulfate), filtered, and concentrated. Medium pressure chromatography using a solvent gradient (4% to 10% methanol/methylene chloride) afforded the title compound of Step A. MS 483.1 $(M+1)^+$ Step B: N-(4-Hydroxy-benzyl)-4-methoxy-N-[4-(2-pyrrolidin-1-yl-ethoxy)-phenyl]-benzenesulfonamide hydrochloride salt 4-Methoxy-N-[4-(2-pyrrolidin-1-yl-ethoxy)-phenyl]-N-[4-(tetrahydro-pyran-2-yloxy)-benzyl]-benzenesulfonamide (1.58 g, 2.79 mmol) was suspended in 3:1 ethanol:1N HCl (30 mL) and the solution was stirred at room temperature for 24 hr. The reaction mixture was quenched with sodium bicarbonate solution and the aqueous solution was washed with methylene chloride. The organic layer was dried (sodium sulfate), filtered, and concentrated to a white solid. The crude material was purified via Biotage® (A Dynax Corp., Charlottesville, Va.) chromatography using 10% methanol/methylene chloride as the eluant. The purified material was suspended in methanol (15 mL) and 4.0M HCl in dioxane (1.5 equiv.) was added. The mixture was stirred at room temperature and was concentrated to dryness to yield the title compound as the HCl salt. MS 483.1 $(M+1)^+$

Example 19

2-Chloro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 487.1 $(M+1)^+$

Example 20

N-(4-Hydroxy-benzyl)-N-[4-(2-pyrrolidin-1-yl-ethoxy)-phenyl]-2-trifluoromethyl-benzenesulfonamide, trifluoroacetate salt Prepared in a manner analogous to that described in Example 4. MS 521.1 $(M+1)^+$

Example 21

2-Cyano-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 478.1 $(M+1)^+$

Example 22

N-(4-Hydroxy-benzyl)-N-[4-(2-pyrrolidin-1-yl-ethoxy)-phenyl]-3-trifluoromethyl-benzenesulfonamide, trifluoroacetate salt Prepared in a manner analogous to that described in Example 4. MS 521.1 $(M+1)^+$

Example 23

N-(4-Hydroxy-benzyl)-3-methyl-N-[4-(2-pyrrolidin-1-yl-ethoxy)-phenyl]-benzenesulfonamide, trifluoroacetate salt Prepared in a manner analogous to that described in Example 4. MS 467.1 $(M+1)^+$

Example 24

3,5-Dichloro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 521.0 $(M+1)^+$

Example 25

N-(4-Hydroxy-benzyl)-2,5-dimethyl-N-[4-(2-pyrrolidin-1-yl-ethoxy)-phenyl]-benzenesulfonamide, trifluoroacetate salt Prepared in a manner analogous to that described in Example 4. MS 481.1 $(M+1)^+$

Example 26

N-(4-Hydroxy-benzyl)-5-methoxy-2-methyl-N-[4-(2-pyrrolidin-1-yl-ethoxy)-phenyl]-benzenesulfonamide, trifluoroacetate salt Prepared in a manner analogous to that described in Example 4. MS 497.2 $(M+1)^+$

Example 27

N-(4-Hydroxy-benzyl)-2,4,6-trimethyl-N-[4-(2-pyrrolidin-1-yl-ethoxy)-phenyl]-benzenesulfonamide, trifluoroacetate salt Prepared in a manner analogous to that described in Example 4. MS 495.2 $(M+1)^+$

Example 28

N-(4-Hydroxy-benzyl)-2,4,6-trimethyl-N-[4-(2-pyrrolidin-1-yl-ethoxy)-phenyl]-benzenesulfonamide, hydrochloride salt Step A: 2,4,6-Trimethyl-N-[4-(2-Dvrrolidin-1-yl-ethoxy)-phenyl]-N-[4-(tetrahydro-pyran-2-yloxy)-benzyl]-benzenesulfonamide

[4-(2-Pyrrolidin-1-yl-ethoxy)-phenyl]-[4-(tetrahydro-pyran-2-yloxy)-benzyl]-amine (421 mg, 1.062 mmol) was dissolved in methylene chloride (10 mL) and triethylamine (0.5 mL, 3.59 mmol) and 2,4,6-trimethyl-benzenesulfonyl chloride (350 mg, 1.06 mmol) were added. The reaction mixture was stirred at room temperature for 20 hr. Water was added and the aqueous solution was washed with methylene chloride (3x). The organic layers were combined, dried (magnesium sulfate), filtered, and concentrated in vacuo. The crude product was purified via radial chromatography using a solvent gradient (methylene chloride to 5% methanol/methylene chloride) to obtain the title product of Step A.

Step B: N-(4-Hydroxy-benzyl)-2,4,6-trimethyl-N-[4-(2-pyrrolidin-1-yl-ethoxy)-phenyl]-benzenesulfonamide, hydrochloride salt 2,4,6-Trimethyl-N-[4-(2-pyrrolidin-1-yl-ethoxy)-phenyl]-N-[4-(tetrahydro-pyran-2-yloxy)-benzyl]-benzenesulfonamide was dissolved in methanol (30 mL) and 1N HCl (5 mL) was added. The reaction mixture was stirred for 30 minutes at room temperature and was concentrated in vacuo. The residue was triturated with methylene chloride followed by ether to obtain the title compound as the HCl salt. MS 495.4 $(M+1)^+$

Example 29

Naphthalene-1-sulfonic acid (4-hydroxy-benzyl)-[4-(2-pyrrolidin-1-yl-ethoxy)-phenyl]-amide, trifluoroacetate salt Prepared in a manner analogous to that described in Example 4. MS 503.1 $(M+1)^+$

Example 30

4-Chloro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 487.1 $(M+1)^+$

Example 31

4-Fluoro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 471.1 $(M+1)^+$

Example 32

N-(4-Hydroxy-benzyl)-N-[4-(2-pyrrolidin-1-yl-ethoxy)-phenyl]-4-trifluoromethoxy-benzenesulfonamide, trifluoroacetate salt Prepared in a manner analogous to that described in Example 4. MS 537.1 $(M+1)^+$

Example 33

N-(4-Hydroxy-benzyl)-4-isopropyl-N-[4-(2-pyrrolidin-1-yl-ethoxy)-phenyl]-benzenesulfonamide, trifluoroacetate salt Prepared in a manner analogous to that described in Example 4. MS 495.2 $(M+1)^+$

Example 34

4-tert-Butyl-N-(4-hydroxy-benzyl)-N-[4-(2-Pyrrolidin-1-yl-ethoxy)-phenyl]-benzenesulfonamide, trifluoroacetate salt Prepared in a manner analogous to that described in Example 4. MS 509.1 $(M+1)^+$

Example 35

4-Cyano-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 478.1 $(M+1)^+$

Example 36

N-(4-Hydroxy-benzyl)-2-methyl-N-[4-(2-pyrrolidin-1-yl-ethoxy)-phenyl]-benzenesulfonamide, trifluoroacetate salt Prepared in a manner analogous to that described in Example 4. MS 467.2 $(M+1)^+$

Example 37

3-Chloro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 487.1 $(M+1)^+$

Example 38

3-Fluoro-N-(4-hydroxy-benzyl)-N-[4-(2-pyrrolidin-1-yl-ethoxy)-phenyl]-benzenesulfonamide, trifluoroacetate salt Prepared in a manner analogous to that described in Example 4. MS 471.1 (M+1)$^+$

Example 39

N-(4-Hydroxy-benzyl)-N-[4-(2-pyrrolidin-1-yl-ethoxy)-phenyl]-4-trifluoromethyl-benzenesulfonamide, trifluoroacetate salt Prepared in a manner analogous to that described in Example 4. MS 521.1 (M+1)$^+$

Example 40

4-Hydroxy-N-(4-hydroxy-benzyl)-N-[4-(2-pyrrolidin-1-yl-ethoxy)-phenyl]-benzenesulfonamide Step A: 4-Hydroxy-N-[4-(2-pyrrolidin-1-yl-ethoxy)-phenyl]-N-[4-(tetrahydro-pyran-2-yloxy)-benzyl]-benzenesulfonamide A solution of [4-(2-pyrrolidin-1-yl-ethoxy)-phenyl]-[4-(tetrahydro-pyran-2-yloxy)-benzyl]-amine (264 mg, 0.666 mmol) in methylene chloride (10 mL) was treated with carbonic acid 4-chlorosulfonyl-phenyl ester ethyl ester (278 mg, 1.05 mmol) and triethylamine (0.3 mL). The reaction mixture was stirred for 60 hr. and water was added. The aqueous solution was washed with methylene chloride (2×). The combined organic layers were dried (sodium sulfate), filtered, and concentrated in vacuo. The crude product was purified via radial chromatography using a solvent gradient (methylene chloride to 5% methanol/methylene chloride) to obtain the title compound of Step A.

Step B: 4-Hydroxy-N-(4-hydroxy-benzyl)-N-[4-(2-pyrrolidin-1-yl-ethoxy)-phenyl]-benzenesulfonamide To a solution of 4-hydroxy-N-[4-(2-pyrrolidin-1-yl-ethoxy)-phenyl]-N-[4-(tetrahydro-pyran-2-yloxy)-benzyl]-benzenesulfonamide in methanol (20 mL) was added 1N HCl (5 mL). After stirring for 2 hr., water was added and the aqueous solution was washed with methylene chloride (3×). The combined organic solutions were washed with saturated aqueous sodium bicarbonate, dried (magnesium sulfate), filtered, and concentrated. The residue was purified via radial chromatography using a solvent gradient (methylene chloride to 10% methanol/methylene chloride) to provide the title compound. $^1$H NMR (CD$_3$OD) δ 7.44 (d, 2H, J=8.0 Hz), 6.96 (d, 2H, J=8.0 Hz), 6.85–6.74 (m, 4H), 6.73 (d, 2H, J=8.0 Hz), 6.58 (d, 2H, J=8.0 Hz), 4.55 (s, 2H), 4.02 (t, 2H, J=5.6 Hz), 2.89 (t, 2H, J=5.6 Hz), 2.67 (bs, 4H), 1.81 (bs, 4H).

Example 41

2-Chloro-N-(4-hydroxy-benzyl)-N-[4-(2-pyrrolidin-1-yl-ethoxy)-phenyl]-4-trifluoromethyl-benzenesulfonamide Step A: 2-Chloro-N-[4-(2-pyrrolidin-1-yl-ethoxy)-phenyl]-N-[4-(tetrahydro-pyran-2-yloxy)-benzyl]-4-trifluoromethyl-benzenesulfonamide To a solution of [4-(2-pyrrolidin-1-yl-ethoxy)-phenyl]-[4-(tetrahydro-pyran-2-yloxy)-benzyl]-amine (0.060 g, 0.15 mmol) in 0.4 mL methylene chloride was added triethylamine (0.06 mL, 0.45 mmol) and 2-chloro-4-trifluoromethyl benzenesulfonyl chloride (0.084 g, 0.3 mmol). The reaction mixture was stirred at room temperature for 6 days. PS-isocyanate resin (Argonaut Technologies, Foster City, Calif.; 0.050 g) and PS-trisamine resin (Argonaut Technologies; 0.050 g) were added and the reaction mixture was stirred for 2 hr. at room temperature. The resin was filtered off and was washed with methylene chloride. The filtrate was concentrated to give the title compound of Step A. MS 639.4 (M+1)$^+$ Step B: 2-Chloro-N-(4-hydroxy-benzyl)-N-[4-(2-pyrrolidin-1-yl-ethoxy)-phenyl]-4-trifluoromethyl-benzenesulfonamide To a solution of crude 2-chloro-N-[4-(2-pyrrolidin-1-yl-ethoxy)-phenyl]-N-[4-(tetrahydro-pyran-2-yloxy)-benzyl]-4-trifluoromethyl-benzenesulfonamide (0.096 g, 0.15 mmol) in 4 mL ethanol was added 1 mL of 1.2N HCl. The reaction mixture was stirred at room temperature for 24 hr. and was diluted with 10 mL saturated aqueous sodium bicarbonate. The aqueous solution was washed with methylene chloride (2×10 mL). The combined organic layers were dried (sodium sulfate), filtered, and concentrated in vacuo. The residue was purified by preparative TLC (1.0 mm silica gel layer, elution with 10% methanol/methylene chloride) to afford 0.039 g (84%) of the title compound. MS 555.3 (M+1)$^+$

Example 42

N-(4-Hydroxy-benzyl)-2-meihoxv-5-methyl-N-[4-(2-pyrrolidin-1-yl-ethoxy)-phenyl]-benzenesulfonamide Prepared in a manner analogous to that described in Example 41. MS 497.4 (M+1)$^+$

Example 43

2,5-Dibromo-N-(4-hydroxy-benzyl)-N-[4-(2-pyrrolidin-1-yl-ethoxy)-phenyl]-benzenesulfonamide Prepared in a manner analogous to that described in Example 41. MS 611.2 (M+1)$^+$

Example 44

2-Chloro-N-(4-hydroxy-benzyl)-N-[4-(2-pyrrolidin-1-yl-ethoxy)-phenyl]-5-trifluoromethyl-benzenesulfonamide Prepared in a manner analogous to that described in Example 41. MS 555.3 (M+1)$^+$

Example 45

N-(4-Hydroxy-benzyl)-2,5-dimethoxy-N-[4-(2-pyrrolidin-1-yl-ethoxy)-phenyl]-benzenesulfonamide Prepared in a manner analogous to that described in Example 41. MS 513.4 (M+1)$^+$

Example 46

5-Fluoro-N-(4-hydroxy-benzyl)-2-methyl-N-[4-(2-pyrrolidin-1-yl-ethoxy)-phenyl]-benzenesulfonamide Prepared in a manner analogous to that described in Example 41. MS 485.3 (M+1)$^+$

Example 47

5-Bromo-N-(4-hydroxy-benzyl)-2-methoxy-N-[4-(2-pyrrolidin-1-yl-ethoxy)-phenyl]-benzenesulfonamide Prepared in a manner analogous to that described in Example 41. MS 563.3 (M+1)$^+$

Example 48

5-Chloro-N-(4-hydroxy-benzyl)-2-methoxy-N-[4-(2-pyrrolidin-1-yl-ethoxy)-phenyl]-benzenesulfonamide Prepared in a manner analogous to that described in, Example 41. MS 517.3 (M+1)$^+$

Example 49

2,5-Dichloro-N-(4-hydroxV-benzyl)-N-[4-(2-pyrrolidin-1-yl-ethoxy)-phenyl]-benzenesulfonamide Prepared in a manner analogous to that described in Example 41. MS 521.3 (M+1)$^+$

Example 50

5-Chloro-N-(4-hydroxy-benzyl)-2-methyl-N-[4-(2-pyrrolidin-1-yl-ethoxy)-phenyl]-benzenesulfonamide Prepared in a manner analogous to that described in Example 41. MS 501.3 (M+1)$^+$

Example 51

4-Bromo-N-(4-hydroxy-benzyl)-N-[4-(2-pyrrolidin-1-yl-ethoxy)-phenyl]-2-trifluoromethoxy-benzenesulfonamide Prepared in a manner analogous to that described in Example 41. MS 617.2 (M+1)$^+$

Example 52

4-Bromo-2-ethyl-N-(4-hydroxy-benzyl)-N-[4-(2-pyrrolidin-1-yl-ethoxy)-phenyl]-benzenesulfonamide Prepared in a manner analogous to that described in Example 41. MS 561.2 (M+1)$^+$

Example 53

4-Bromo-N-(4-hydroxy-benzyl)-2-methyl-N-[4-(2-pyrrolidin-1-yl-ethoxy)-phenyl]-benzenesulfonamide Prepared in a manner analogous to that described in Example 41. MS 547.2 (M+1)$^+$

Example 54

2-Chloro-4-fluoro-N-(4-hydroxy-benzyl)-N-[4-(2-pyrrolidin-1-yl-ethoxy)-phenyl]-benzenesulfonamide Prepared in a manner analogous to that described in Example 41. MS 505.3 (M+1)$^+$

Example 55

2,3,4-Trifluoro-N-(4-hydroxy-benzyl)-N-[4-(2-pyrrolidin-1-yl-ethoxy)-phenyl]-benzenesulfonamide Prepared in a manner analogous to that described in Example 41. MS 507.3 (M+1)$^+$

Example 56

2,4-Difluoro-N-(4-hydroxy-benzyl)-N-[4-(2-pyrrolidin-1-yl-ethoxy)-phenyl]-benzenesulfonamide Prepared in a manner analogous to that described in Example 41. MS 489.3 (M+1)$^+$

Example 57

2,4-Dichloro-N-(4-hydroxy-benzyl)-6-methyl-N-[4-(2-pyrrolidin-1-yl-ethoxy)-phenyl]-benzenesulfonamide Prepared in a manner analogous to that described in Example 41. MS 535.3 (M+1)$^+$

Example 58

2,4-Dichloro-N-(4-hydroxy-benzyl)-N-[4-(2-pyrrolidin-1-yl-ethoxy)-phenyl]-benzenesulfonamide Prepared in a manner analogous to that described in Example 41. MS 521.2 (M+1)$^+$

Example 59

2,6-Dichloro-N-(4-hydroxy-benzyl)-N-[4-(2-pyrrolidin-1-yl-ethoxy)-phenyl]-4-trifluoromethyl-benzenesulfonamide Prepared in a manner analogous to that described in Example 41. MS 589.3 (M+1)$^+$

Example 60

4-Chloro-N-(4-hydroxy-benzyl)-N-[4-(2-pyrrolidin-1-yl-ethoxy)-phenyl]-benzenesulfonamide Prepared in a manner analogous to that described in Example 41. MS 486.7 (M+1)$^+$

Example 61

4-Chloro-N-(4-hydroxy-benzyl)-N-[4-(2-pyrrolidin-1-yl-ethoxy)-phenyl]-benzenesulfonamide, hydrochloride To a solution of 4-chloro-N-(4-hydroxy-benzyl)-N-[4-(2-pyrrolidin-1-yl-ethoxy)-phenyl]benzenesulfonamide (0.016 g, 32.9 µmol) in methanol (1 mL) was added HCl as a 1M solution in ether (0.045 ml). The reaction mixture was stirred at room temperature for 1 hr., and then concentrated in vacuo to give the title compound (0.017 g, 32.5 µmol).

TABLE 1

[Structure: HO-C6H4-CH2-N(X-R5)-C6H4-O-CH2CH2-pyrrolidine]

| Example | X | R5 | MS (M + 1)+ or 1H NMR |
|---|---|---|---|
| 1 | CO | cyclohexyl | 423.2 |
| 2 | CO | cyclohexyl | 423.2 |
| 3 | CO | neopentyl | 411.2 |
| 4 | CO | —CH2CH2Ph | 445.2 |
| 5 | CO | cyclopropyl | 381.2 |
| 6 | CO | —CH(CH2CH3)2 | 411.3 |
| 7 | CO | cyclopentyl | 409.2 |
| 8 | CO | 4-cyclohexenyl | 421.2 |
| 9 | SO2 | Ph | 453.1 |
| 10 | SO2 | p-tolyl | 467.1 |
| 11 | SO2 | benzyl | 467.1 |
| 12 | SO2 | isopropyl | 419.1 |
| 13 | SO2 | —CH=CHPh | 479.1 |
| 14 | SO2 | 2-naphthyl | 503.1 |
| 15 | SO2 | 2-naphthalen-1-yl-ethyl | 531.1 |
| 16 | SO2 | p-anisoyl | 483.1 |
| 17 | SO2 | 8-quinolinyl | 504.1 |
| 18 | SO2 | p-anisoyl | 483.1 |
| 19 | SO2 | 2-Cl—Ph | 487.1 |
| 20 | SO2 | 2-CF3—Ph | 521.1 |
| 21 | SO2 | 2-CN—Ph | 478.1 |
| 22 | SO2 | 3-CF3—Ph | 521.1 |
| 23 | SO2 | m-tolyl | 467.1 |
| 24 | SO2 | 3,5-dichlorophenyl | 521.0 |
| 25 | SO2 | 2,5-dimethylphenyl | 481.1 |
| 26 | SO2 | 2-Me-5-OMe—Ph | 497.2 |
| 27 | SO2 | 2,4,6-trimethylphenyl | 495.2 |
| 28 | SO2 | 2,4,6-trimethylphenyl | 495.4 |
| 29 | SO2 | 1-naphthyl | 503.1 |
| 30 | SO2 | 4-Cl—Ph | 487.1 |
| 31 | SO2 | 4-F—Ph | 471.1 |
| 32 | SO2 | 4-OCF3—Ph | 537.1 |
| 33 | SO2 | 4-i-propyl-Ph | 495.2 |
| 34 | SO2 | 4-tert-butyl-Ph | 509.1 |
| 35 | SO2 | 4-CN—Ph | 478.1 |
| 36 | SO2 | o-tolyl | 467.2 |
| 37 | SO2 | 3-Cl—Ph | 487.1 |
| 38 | SO2 | 3-F—Ph | 471.1 |
| 39 | SO2 | 4-CF3—Ph | 521.1 |
| 40 | SO2 | 4-OH—Ph | 1H NMR (CD3OD) δ 7.44 (d, 2H, J = 8.0 Hz), 6.96 (d, 2H, J = 8.0 Hz), 6.85–6.74 (m, 4H,), 6.73 (d, 2H, J = 8.0 Hz), 6.58 (d, 2H, J = 8.0 Hz), 4.55 (s, 2H), 4.02 (t, 2H, J = 5.6 Hz), 2.89 (t, 2H, J = 5.6 Hz), 2.67 (bs, 4H), 1.81 (bs, 4H). |
| 41 | SO2 | 2-Cl-4-CF3—Ph | 555.3 |
| 42 | SO2 | 2-OMe-5-Me-phenyl | 497.4 |
| 43 | SO2 | 2,5-dibromo-phenyl | 611.2 |
| 44 | SO2 | 2-Cl-5-CF3-phenyl | 555.3 |
| 45 | SO2 | 2,5-dimethoxyphenyl | 513.4 |
| 46 | SO2 | 2-Me-5-F-phenyl | 485.3 |
| 47 | SO2 | 2-OMe-5-Br-phenyl | 563.3 |
| 48 | SO2 | 2-OMe-5-Cl-phenyl | 517.3 |
| 49 | SO2 | 2,5-dichloro-phenyl | 521.3 |
| 50 | SO2 | 2-Me-5-Cl-phenyl | 501.3 |
| 51 | SO2 | 2-OCF3-4-Br—Ph | 617.2 |
| 52 | SO2 | 2-Et-4-Br—Ph | 561.2 |
| 53 | SO2 | 2-Me-4-Br—Ph | 547.2 |
| 54 | SO2 | 2-Cl-4-F—Ph | 505.3 |
| 55 | SO2 | 2,3,4-trifluorophenyl | 507.3 |
| 56 | SO2 | 2,4-difluorophenyl | 489.3 |

TABLE 1-continued

| Example | X | R⁵ | MS (M + 1)⁺ or ¹H NMR |
|---------|-----|-----------------------|------------------------|
| 57 | SO₂ | 2,4-dichloro-6-Me—Ph | 535.3 |
| 58 | SO₂ | 2,4-dichlorophenyl | 521.2 |
| 59 | SO₂ | 2,6-dichloro-4-CF₃—Ph | 589.3 |
| 60 | SO₂ | 4-Cl—Ph | 486.7 |
| 61 | SO₂ | 4-Cl—Ph | $^1$H NMR (CD$_3$OD) δ 7.60 (d, 2H, J = 8.4 Hz), 7.54 (d, 2H, J = 8.8 Hz), 6.96 (d, 2H, J = 8.4 Hz), 6.88–6.82 (m, 4H), 6.57 (d, 2H, J = 8.4 Hz), 4.61 (s, 2H), 4.23 (t, 2H, J = 4.8 Hz), 3.70–3.60 (m, 2H), 3.58 (t, 2H, J = 4.8 Hz), 3.17–3.13 (m, 2H), 2.15–2.12 (m, 2H), 2.02–1.98 (m, 2H). |

EXAMPLES 62 TO 83

The compounds of the general structure

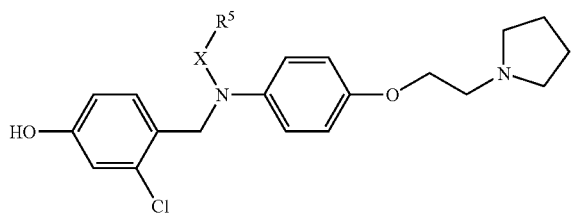

prepared according to the methods depicted in Scheme 1 hereinabove, and set forth in Table 2 hereinbelow, were prepared as disclosed in the following Examples 62 to 83.

Example 62

N-(2-Chloro-4-hydroxy-benzyl)-3,3-dimethyl-N-[4-(2-pyrrolidin-1-yl-ethoxy)-phenyl]-butyramide, trifluoroacetate salt Step A: N-[2-Chloro-4-(tetrahydro-pyran-2-yloxy)-benzyl]-3,3-dimethyl-N-[4-(2-pyrrolidin-1-yl-ethoxy)-phenyl]-butyramide To a solution of [2-chloro-4-(tetrahydro-pyran-2-yloxy)-benzyl]-[4-(2-pyrrolidin-1-yl-ethoxy)-phenyl]-amine (0.100 g, 0.232 mmol) and triethylamine (0.100 mL, 0.696 mmol) in 2 mL methylene chloride was added tert-butylacetyl chloride (0.081 mL, 0.58 mmol) dropwise. The reaction mixture was stirred for 1 hr. at room temperature. Saturated aqueous sodium bicarbonate was added and the layers were separated. The aqueous layer was extracted with an additional 2 mL of methylene chloride. The combined organic layers were concentrated to give the title compound of Step A. MS 529.2 (M+1)⁺

Step B: N-(2-Chloro-4-hydroxy-benzyl)-3,3-dimethyl-N-[4-(2-pyrrolidin-1-yl-ethoxy)-phenyl]-butyramide, trifluoroacetate salt The crude N-[2-chloro-4-(tetrahydro-pyran-2-yloxy)-benzyl]-3,3-dimethyl-N-[4-(2-pyrrolidin-1-yl-ethoxy)-phenyl]-butyramide prepared in Step A was suspended in 2 mL of a 3:1 (v/v) mixture of ethanol:1N HCl and the reaction mixture was stirred at room temperature for 24 hr. The reaction was quenched with saturated aqueous sodium bicarbonate and the aqueous solution was washed with two portions of methylene chloride. The combined organic layers were concentrated. The residue was purified by reverse phase HPLC (98:2 water:0.1% trifluoroacetic acid to 98:2 acetonitrile:water) to afford the title compound. MS 445.2 (M+1)⁺

Example 63

N-(2-Chloro-4-hydroxy-benzyl)-N-[4-(2-pyrrolidin-1-yl-ethoxy)-phenyl]-benzenesulfonamide, trifluoroacetate salt Prepared in a manner analogous to that described in Example 62. MS 487.0 (M+1)⁺

Example 64

Cyclohexanecarboxylic acid (2-chloro-4-hydroxy-benzyl)-[4-(2-pyrrolidin-1-yl-ethoxy)-phenyl]-amide Prepared in a manner analogous to that described in Example 62. MS 457.1 (M+1)⁺

Example 65

N-(2-Chloro-4-hydroxy-benzyl)-3-phenyl-N-[4-(2-pyrrolidin-1-yl-ethoxy)-phenyl]-propionamide, trifluoroacetate salt Prepared in a manner analogous to that described in Example 62. MS 479.1 (M+1)⁺

Example 66

N-(2-Chloro-4-hydroxy-benzyl)-N-[4-(2-pyrrolidin-1-yl-ethoxy)-phenyl]-benzamide, trifluoroacetate salt Prepared in a manner analogous to that described in Example 62. MS 451.1 (M+1)$^+$

Example 67

Cyclohexanecarboxylic acid (2-chloro-4-hydroxy-benzyl)-[4-(2-pyrrolidin-yl-ethoxy)-phenyl]-amide, hydrochloride salt Step A: Cyclohexanecarboxylic acid [2-chloro-4-(tetrahydro-pyran-2-yloxy)-benzyl]-[4-(2-Pyrrolidin-1-yl-ethoxy)-phenyl]-amide To a solution of cyclohexanecarbonyl chloride (990 mg, 6.75 mmol) in methylene chloride (30 mL) was added a mixture of (2-chloro-4-(tetrahydro-pyran-2-yloxy)-benzyl]-[4-(2-pyrrolidin-1-yl-ethoxy)-phenyl]-amine (1.94 g, 4.5 mmol) and triethylamine (1.3 mL, 9.0 mmol) in methylene chloride (15 mL) dropwise. The reaction mixture was stirred at room temperature for 24 hr. The reaction mixture was quenched with saturated aqueous sodium bicarbonate solution and the aqueous solution was washed with methylene chloride. The organic solution was dried (sodium sulfate), filtered and concentrated in vacuo. The crude product was purified by Biotage® chromatography using 5% methanol/methylene chloride to afford the title compound of Step A as an oil (2.12 g). MS 541.3 (M+1)$^+$ Step B: Cyclohexanecarboxylic acid (2-chloro-4-hydroxy-benzyl)-[4-(2-pyrrolidin-1-yl-ethoxy)-phenyl]-amide, hydrochloride salt A solution of cyclohexanecarboxylic acid [2-chloro-4-(tetrahydro-pyran-2-yloxy)-benzyl]-[4-(2-pyrrolidin-1-yl-ethoxy)-phenyl]-amide (2.0 g) in 3:1 ethanol:1N HCl (40 mL) was stirred at room temperature for 1.5 hr. Saturated aqueous sodium bicarbonate solution was added and the aqueous solution was washed with methylene chloride. The organic solution was dried (magnesium sulfate), filtered and concentrated in vacuo. The crude product was purified by Biotage® chromatography (methylene chloride to 4% methanol/methylene chloride). The resulting white solid (1.53 g) was suspended in methanol (20 mL) and 4M HCl in dioxane was added. The mixture was stirred at room temperature for 1 hr. and was concentrated in vacuo to yield the title compound as a tan solid (1.60 g). MS 317.2 (MH$^+$–40)

Example 68

N-(2-Chloro-4-hydroxy-benzyl)-3-methyl-N-[4-(2-pyrrolidin-1-yl-ethoxy)-phenyl]-benzamide, trifluoroacetate salt Step A: N-[Chloro-4-(tetrahydro-pyran-2-yloxy)-benzyl]-3-methyl-N-[4-(2-pyrrolidin-1-yl-ethoxy)-phenyl]-benzamide A solution of [2-chloro-4-(tetrahydro-pyran-2-yloxy)-benzyl]-[4-(2-pyrrolidin-1-yl-ethoxy)-phenyl]-amine (100 mg, 0.232 mmol) and triethylamine (0.100 mL, 0.696 mmol) in methylene chloride was added to m-toluenecarbonyl chloride (72 mg, 0.46 mmol). The reaction mixture was stirred at room temperature for 24 hr. Saturated aqueous sodium bicarbonate was added and the layers were separated. The aqueous layer was washed with 2 mL of methylene chloride. The combined organic layers were concentrated to give the title compound of Step A. MS 549.1 (M+1)$^+$ Step B: N-(2-Chloro-4-hydroxy-benzyl)-3-methyl-N-[4-(2-pyrrolidin-1-yl-ethoxy)-phenyl]-benzamide The crude N-[2-chloro-4-(tetrahydro-pyran-2-yloxy)-benzyl]-3-methyl-N-[4-(2-pyrrolidin-1-yl-ethoxy)-phenyl]-benzamide prepared in Step A was suspended in 3 mL of a 3:1 (v/v) mixture of ethanol:1N HCl and stirred at room temperature for 24 hr. Saturated aqueous sodium bicarbonate was added and the aqueous solution was washed with methylene chloride. The organic solution was concentrated. The residue was purified by reverse phase HPLC (98:2 water:0.1% trifluoroacetic acid to 98:2 acetonitrile:water) to afford N-(2-chloro-4-hydroxy-benzyl)-3-methyl-N-[4-(2-pyrrolidin-1-yl-ethoxy)-phenyl]-benzamide as the trifluoroacetate salt. MS 465.3 (M+1)$^+$

Example 69

N-(2-Chloro-4-hydroxy-benzyl)-4-methoxy-N-[4-(2-pyrrolidin-1-yl-ethoxy)-phenyl]-benzenesulfonamide trifluoroacetate Prepared in a manner analogous to that described in Example 68. MS 517.2 (M+1)$^+$

Example 70

N-(2-Chloro-4-hydroxy-benzyl)-3-methyl-N-[4-(2-pyrrolidin-1-yl-ethoxy)-phenyl]-benzenesulfonamide trifluoroacetate Prepared in a manner analogous to that described in Example 62. MS 501.1 (M+1)$^+$

Example 71

2-Phenyl-ethenesulfonic acid (2-chloro-4-hydroxy-benzyl)-[4-(2-pyrrolidin-1-yl-ethoxy)-phenyl]-amide trifluoroacetate Prepared in a manner analogous to that described in Example 62. MS 513.2 (M+1)$^+$

Example 72

2,4-Dichloro-N-(2-chloro-4-hydroxy-benzyl)-N-[4-(2-pyrrolidin-1-yl-ethoxy)-phenyl]-benzenesulfonamide Step A: 2,4-Dichloro-N-[2-chloro-4-(tetrahydro-pyran-2-yloxy)-benzyl]-N-[4-(2-pyrrolidin-1-yl-ethoxy)-phenyl]-benzenesulfonamide To a solution of [2-chloro-4-(tetrahydro-pyran-2-yloxy)-benzyl]-[4-(2-pyrrolidin-1-yl-ethoxy)-phenyl]-amine (0.060 g, 0.15 mmol) in 0.4 mL methylene chloride was added triethylamine (0.06 mL, 0.45 mmol) and 2,4-dichlorobenzenesulfonyl chloride (0.074 g, 0.3 mmol). The reaction mixture was stirred at room temperature for 6 days. PS-isocyanate resin (0.050 g) and PStrisamine resin (0.050 g) were added and the reaction mixture was stirred for 2 hr. at room temperature. The resin was filtered off with the aid of methylene chloride. The filtrate was concentrated to afford the title compound of Step A (0.096 g). MS 639.3 (M+1)$^+$ Step B: 2,4-Dichloro-N-(2-chloro-4-hydroxy-benzyl)-N-[4-(2-pyrrolidin-1-yl-ethoxy)-phenyl]-benzenesulfonamide To a solution of crude 2,4-dichloro-N-[2-chloro-4-(tetrahydro-pyran-2-yloxy)-benzyl]-N-[4-(2-pyrrolidin-1-yl-ethoxy)-phenyl]-benzenesulfonamide (0.096 g, 0.15 mmol) in 4 mL absolute ethanol was added 1 mL of 1.2N HCl. The reaction mixture was stirred at room temperature for 24 hr. and was diluted with 10 mL saturated aqueous sodium bicarbonate. The aqueous solution was washed with methylene chloride (2×10 mL). The combined organic layers were dried (sodium sulfate), filtered, and concentrated. The residue was purified by preparative TLC (1.0 mm silica gel layer, elution with 10% methanol/ethyl acetate) to afford 0.029 g of the title compound. MS 557.3 (M+1)$^+$

Example 73

2-Chloro-N-(2-chloro-4-hydroxy-benzyl)-N-[4-(2-pyrrolidin-1-yl-ethoxy)-phenyl]-4-trifluoromethyl-benzenesulfonamide Prepared in a manner analogous to that described in Example 72. MS 589.2 (M+1)$^+$

Example 74

4-Bromo-N-(2-chloro-4-hydroxy-benzyl)-N-[4-(2-pyrrolidin-1-yl-ethoxy)-phenyl]-2-trifluoromethoxy-benzenesulfonamide Prepared in a manner analogous to that described in Example 72. MS 651.1 (M+1)$^+$

Example 75

4-Bromo-N-(2-chloro-4-hydroxy-benzyl)-2-ethyl-N-[4-(2-pyrrolidin-1-yl-ethoxy)-phenyl]-benzenesulfonamide Prepared in a manner analogous to that described in Example 72. MS 595.1 (M+1)$^+$

Example 76

4-Bromo-N-(2-chloro-4-hydroxy-benzyl)-2-methyl-N-[4-(2-pyrrolidin-1-yl-ethoxy)-phenyl]-benzenesulfonamide Prepared in a manner analogous to that described in Example 72. MS 581.1 (M+1)$^+$

Example 77

2-Chloro-N-(2-chloro-4-hydroxy-benzyl)-4-fluoro-N-[4-(2-pyrrolidin-1-yl-ethoxy)-phenyl]-benzenesulfonamide Prepared in a manner analogous to that described in Example 72. MS 539.2 (M+1)$^+$

Example 78

N-(2-Chloro-4-hydroxy-benzyl)-2,3,4-trifluoro-N-[4-(2-pyrrolidin-1-yl-ethoxy)-phenyl]-benzenesulfonamide Prepared in a manner analogous to that described in Example 72. MS 541.2 (M+1)$^+$

Example 79

N-(2-Chloro-4-hydroxy-benzyl)-2,4-difluoro-N-[4-(2-pyrrolidin-1-yl-ethoxy)-phenyl]-benzenesulfonamide Prepared in a manner analogous to that described in Example 72. MS 523.3 (M+1)$^+$

Example 80

2,4-Dichloro-N-(2-chloro-4-hydroxy-benzyl)-6-methyl-N-[4-(2-pyrrolidin-1-yl-ethoxy)-phenyl]-benzenesulfonamide Prepared in a manner analogous to that described in Example 72. MS 569.3 (M+1)$^+$

Example 81

2,6-Dichloro-N-(2-chloro-4-hydroxy-benzyl)-N-[4-(2-pyrrolidin-1-yl-ethoxy)-phenyl]-4-trifluoromethyl-benzenesulfonamide Prepared in a manner analogous to that described in Example 72. MS 623.2 (M+1)$^+$

Example 82

N-(2-Chloro-4-hydroxy-benzyl)-4-methoxy-N-[4-(2-pyrrolidin-1-yl-ethoxy)-phenyl]-benzenesulfonamide Prepared in a manner analogous to that described in Example 72. MS 516.6 (M+1)$^+$

Example 83

N-(2-Chloro-4-hydroxy-benzyl)-4-methoxy-N-[4-(2-pyrrolidin-1-yl-ethoxy)-phenyl]-benzenesulfonamide, hydrochloride Prepared in a manner a manner analogous to that described in Example 72. The HCl salt was prepared by the following procedure:

To a solution of N-(2-chloro-4-hydroxy-benzyl)-4-methoxy-N-[4-(2-pyrrolidin-1-yl-ethoxy)-phenyl]-benzenesulfonamide (0.016 g, 30.9 μmol) in methanol (1 mL) was added HCl as a 1.0M solution in ether (0.04 ml, 40.0 μmol). The reaction mixture was stirred at room temperature for 1 hr., and then concentrated to give the title hydrochloride salt. $^1$H NMR (CD$_3$OD) δ 7.56 (d, 2H, J=9.2 Hz), 7.13 (d, 1H, J=8.4 Hz), 7.03 (d, 2H, J=8.8 Hz), 6.89 (d, 2H, J=9.2 Hz), 6.82 (d, 2H, J=8.8 Hz), 6.61 (d, J=2.4 Hz), 6.53 (dd, 1H, J=2.0 Hz, J=8.4 Hz), 4.72 (s, 2H), 4.23 (t, 2H, J=4.8 Hz), 3.86 (s, 3H), 3.70–3.60 (m, 2H), 3.58 (t, 2H, J=4.8 Hz), 3.17–3.13 (m, 2H), 2.16–2.13 (m, 2H), 2.02–1.98 (m, 2H).

TABLE 2

[Structure: HO-phenyl(Cl)-CH2-N(aryl-O-CH2CH2-pyrrolidinyl)-X-R5]

| Example | X | R⁵ | MS (M + 1)⁺ or ¹H NMR |
|---|---|---|---|
| 62 | CO | neopentyl | 445.2 |
| 63 | SO₂ | Ph | 487.0 |
| 64 | CO | cyclohexyl | 457.1 |
| 65 | CO | —CH2CH2Ph | 479.1 |
| 66 | CO | Ph | 451.1 |
| 67 | CO | cyclohexyl | 317.2 |
| 68 | CO | m-tolyl | 465.3 |
| 69 | SO₂ | p-anisoyl | 517.2 |
| 70 | SO₂ | m-tolyl | 501.1 |
| 71 | SO₂ | —CH=CHPh | 513.2 |
| 72 | SO₂ | 2,4-dichlorophenyl | 557.3 |
| 73 | SO₂ | 2-Cl-4-CF₃—Ph | 589.2 |
| 74 | SO₂ | 2-OCF₃-4-Br—Ph | 651.1 |
| 75 | SO₂ | 2-Et-4-Br—Ph | 595.1 |
| 76 | SO₂ | 2-Me-4-Br—Ph | 581.1 |
| 77 | SO₂ | 2-Cl-4-F—Ph | 539.2 |
| 78 | SO₂ | 2,3,4-trifluorophenyl | 541.2 |
| 79 | SO₂ | 2,4-difluorophenyl | 523.3 |
| 80 | SO₂ | 2,4-dichloro-6-Me—Ph | 569.3 |
| 81 | SO₂ | 2,6-dichloro-4-CF₃-Ph | 623.2 |
| 82 | SO₂ | p-anisoyl | 516.6 |
| 83 | SO₂ | p-anisoyl | ¹H NMR (CD₃OD) δ 7.56 (d, 2H, J = 9.2 Hz), 7.13 (d, 1H, J = 8.4 Hz), 7.03 (d, 2H, J = 8.8 Hz), 6.89 (d, 2H, J = 9.2 Hz), 6.82 (d, 2H, J = 8.8 Hz), 6.61 (d, 1H, J = 2.4 Hz), 6.53 (dd, 1H, J = 2.0 Hz, J = 8.4 Hz), 4.72 (s, 2H), 4.23 (t, 2H, J = 4.8 Hz), 3.86 (s, 3H), 3.70–3.60 (m, 2H), 3.58 (t, 2H, J = 4.8 Hz), 3.17–3.13 (m, 2H), 2.16–2.13 (m, 2H), 2.02–1.98 (m, 2H). |

EXAMPLES 84 TO 89

The compounds of the general structure

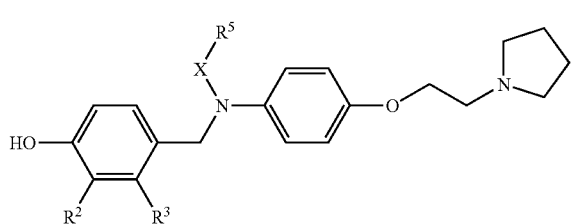

prepared according to the methods depicted in Scheme 1 hereinabove, and set forth in Table 3 hereinbelow, were prepared as disclosed in the following Examples 84 to 89.

Example 84

Cyclohexanecarboxylic acid (4-hydroxy-2-methoxy-benzyl)-[4-(2-pyrrolidin-1-yl-ethoxy)-phenyl]-amide, trifluoroacetate salt Step A: Cyclohexanecarboxylic acid [2-methoxy-4-(tetrahydro-pyran-2-yloxy)-benzyl]-[4-(2-pyrrolidin-1-yl-ethoxy)-phenyl]-amide To a solution of [2-methoxy-4-(tetrahydro-pyran-2-yloxy)-benzyl]-[4-(2-pyrrolidin-1-yl-ethoxy)-phenyl]-amine (0.100 g, 0.23 mmol) and triethylamine (0.10 mL, 0.70 mmol) in 2 mL methylene chloride was added cyclohexanecarbonyl chloride (0.078 mL, 0.58 mmol), dropwise. The reaction mixture was stirred for 1 hr. at room temperature. Saturated aqueous sodium bicarbonate was added and the layers were separated. The aqueous layer was washed with an additional 2 mL of methylene chloride. The combined organic layers were concentrated in vacuo to give the title compound of Step A. MS 537.2 $(M+1)^+$ Step B: Cyclohexanecarboxylic acid (4-hydroxy-2-methoxy-benzyl)-[4-(2-pyrrolidin-1-yl-ethoxy)-phenyl]-amide, trifluoroacetate salt The crude cyclohexanecarboxylic acid [2-methoxy-4-(tetrahydro-pyran-2-yloxy)-benzyl]-[4-(2-pyrrolidin-1-yl-ethoxy)-phenyl]-amide prepared in Step A was suspended in 2 mL of a 3:1 (v/v) mixture of ethanol:1N HCl and the reaction mixture was stirred at room temperature for 24 hr. The reaction mixture was quenched with saturated aqueous sodium bicarbonate and the aqueous solution was washed with two portions of methylene chloride. The combined organic layers were concentrated. The residue was purified by reverse phase HPLC (98:2 water:0.1% trilfuoroacetic acid to 98:2 acetonitrile:water) to afford cyclohexanecarboxylic acid (4-hydroxy-2-methoxy-benzyl)-[4-(2-pyrrolidin-1-ylethoxy)-phenyl]-amide as the trifluoroacetate salt. MS 453.2 $(M+1)^+$ Example 85

N-(4-Hydroxy-3-methyl-benzyl)-2,4,6-trimethyl-N-[4-(2-pyrrolidin-1-yl-ethoxy)-phenyl]-benzenesulfonamide Step A: 2,4,6-Trimethyl-N-[3-methyl-4-(tetrahydro-pyran-2-yloxy)-benzyl]-N-[4-(2-pyrrolidin-1-yl-ethoxy)-phenyl]-benzenesulfonamide To a solution of [3-methyl-4-(tetrahydro-pyran-2-yloxy)-benzyl]-[4-(2-pyrrolidin-1-yl-ethoxy)-phenyl]-amine (0.062 g, 0.15 mmol) in 0.4 mL methylene chloride was added triethylamine (0.06 mL, 0.45 mmol) and 2-mesitylene sulfonyl chloride (0.066 g, 0.3 mmol). The reaction mixture was stirred at room temperature for 24 hr. PS-isocyanate resin (0.050 g) and PS-trisamine resin (0.050 g) were added and the reaction mixture was stirred for 2 hr. at room temperature. The resin was filtered off with the aid of methylene chloride. The filtrate was concentrated to give the title compound of Step A (0.089 g). MS 593.3 $(M+1)^+$ Step B: N-(4-Hydroxy-3-methyl-benzyl)-2,4,6-trimethyl-N-[4-(2-Pyrrolidin-1-yl-ethoxy)-phenyl]-benzenesulfonamide To a solution of crude 2,4,6-trimethyl-N-[3-methyl-4-(tetrahydro-pyran-2-yloxy)-benzyl]-N-[4-(2-pyrrolidin-1-yl-ethoxy)-phenyl]-benzenesulfonamide (0.089 g, 0.15 mmol) prepared in Step A in 4 mL ethanol was added 0.8 mL of 1.2N HCl. The reaction mixture was stirred at room temperature for 2 days and was diluted with 10 mL saturated aqueous sodium bicarbonate. The aqueous solution was washed with methylene chloride (2×10 mL). The combined organic layers were dried (sodium sulfate), filtered, and concentrated in vacuo. The residue was purified by preparative TLC (1.0 mm silica gel layer, eluting with 10% methanol/ethyl acetate) to afford 0.040 g of the title compound. MS 509.1 $(M+1)^+$ Example 86

2-Chloro-N-(4-hydroxy-3-methyl-benzyl)-N-[4-(2-pyrrolidin-1-yl-ethoxy)phenyl]-benzenesulfonamide Prepared in a manner analogous to that described in Example 85. MS 501.2 $(M+1)^+$ Example 87

3-Chloro-N-(4-hydroxy-3-methyl-benzyl)-N-[4-(2-pyrrolidin-1-yl-ethoxy)-phenyl]-benzenesulfonamide Prepared in a manner analogous to that described in Example 85. MS 501.4 $(M+1)^+$ Example 88

N-(4-Hydroxy-3-methyl-benzyl)-N-[4-(2-pyrrolidin-1-yl-ethoxy)-phenyl]-benzenesulfonamide Prepared in a manner analogous to that described in Example 85. MS 467.1 $(M+1)^+$ Example 89

N-(4-Hydroxy-3-methyl-benzyl)-4-methyl-N-[4-(2-pyrrolidin-1-yl-ethoxy)-phenyl]-benzenesulfonamide Prepared in a manner analogous to that described in Example 85. MS 481.2 $(M+1)^+$

TABLE 3

| Example | $R^2$ | $R^3$ | X | $R^5$ | MS $(M+1)^+$ |
|---|---|---|---|---|---|
| 84 | H | OMe | CO | Cyclohexyl | 453.2 |
| 85 | Me | H | $SO_2$ | 2,4,6-trimethylphenyl | 509.1 |
| 86 | Me | H | $SO_2$ | 2-Cl—Ph | 501.2 |
| 87 | Me | H | $SO_2$ | 3-Cl—Ph | 501.4 |
| 88 | Me | H | $SO_2$ | Ph | 467.1 |
| 89 | Me | H | $SO_2$ | p-tolyl | 481.2 |

EXAMPLES 90 TO 147

The compounds of the general structure

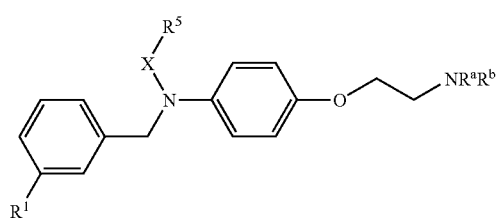

prepared according to the methods depicted in Scheme 1 hereinabove, and set forth in Table 4 hereinbelow, were prepared as disclosed in the following Examples 90 to 147.

Example 90

Cyclohexanecarboxylic acid (3-hydroxy-benzyl)-[4-(2-pyrrolidin-1-yl-ethoxy)-phenyl]-amide Step A: Cyclohexanecarboxylic acid [4-(2-pyrrolidin-1-yl-ethoxy)-phenyl]-[3-(tetrahydro-pyran-2-yloxy)-benzyl]-amide A solution of [4-(2-pyrrolidin-1-yl-ethoxy)-phenyl]-[3-(tetrahydro-pyran-2-yloxy)-benzyl]-amine (119 mg, 0.3 mmol) and triethylamine (0.125 mL, 0.90 mmol) in methylene chloride was added to a vial charged with cyclohexanecarbonyl chloride (88 mg, 0.6 mmol). The reaction mixture was stirred at room temperature for 24 hr. Saturated aqueous sodium bicarbonate was added until the solution was basic and the layers were separated. The aqueous layer was washed with methylene chloride. The organic layers were combined and evaporated under a stream of nitrogen to give the title compound of Step A.

Step B: Cyclohexanecarboxylic acid (3-hydroxy-benzyl)-[4-(2-pyrrolidin-1-yl-ethoxy)-phenyl]-amide Cyclohexanecarboxylic acid [4-(2-pyrrolidin-1-yl-ethoxy)-phenyl]-[3-(tetrahydro-pyran-2-yloxy)-benzyl]-amide was deprotected by stirring in a 3:1 solution of ethanol:1N HCl at room temperature for 24 hr. Saturated sodium bicarbonate solution was added until basic, and the aqueous solution was washed with methylene chloride. The organic layer was poured onto a silica gel plug and the product was eluted using a solvent gradient (methylene chloride to 10% methanol/methylene chloride) to obtain the title compound. MS 423.2 (M+1)$^+$

Example 91

2,4,6-Trichloro-N-(3-hydroxy-benzyl)-N-[4-(2-pyrrolidin-1-yl-ethoxy)-phenyl]-benzamide Step A: 2,4,6-Trichloro-N-[4-(2-pyrrolidin-1-yl-ethoxy)-phenyl]-N-[3-(tetrahydro-pyran-2-yloxy)-benzyl]-benzamide To a solution of [4-(2-pyrrolidin-1-yl-ethoxy)-phenyl]-[3-(tetrahydro-pyran-2-yloxy)-benzyl]-amine (0.050 g, 0.13 mmol) in 0.5 mL methylene chloride was added triethylamine (0.035 mL, 0.25 mmol), 2,4,6-trichlorobenzoyl chloride (0.061 g, 0.25 mmol), and catalytic N,N-dimethylaminopyridine (DMAP). The reaction mixture was stirred overnight at room temperature. The reaction was concentrated to give the title compound of Step A which was used in Step B without further purification. MS 605.4 (M+1)$^+$ Step B: 2,4,6-Trichloro-N-(3-hydroxy-benzyl)-N-[4-(2-pyrrolidin-1-yl-ethoxy)-phenyl]-benzamide To a solution of crude 2,4,6-trichloro-N-[4-(2-pyrrolidin-1-yl-ethoxy)-phenyl]-N-[3-(tetrahydro-pyran-2-yloxy)-benzyl]-benzamide (0.076 g, 0.13 mmol) prepared in Step A in 0.5 mL methanol was added HCl (0.78 mL of a 4.0M solution in 1,4-dioxane, 3.12 mmol) and triethylsilane (0.20 mL, 1.30 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. The residue was purified by preparative TLC (1.0 mm silica gel layer, eluting with 10% methanol/methylene chloride) to afford 0.022 g of 2,4,6-trichloro-N-(3-hydroxy-benzyl)-N-[4-(2-pyrrolidin-1-yl-ethoxy)-phenyl]-benzamide. $^1$H NMR (CDCl$_3$) δ 7.13 (s, 2H), 7.10–7.05 (m, 1H), 7.03 (d, 2H, J=12.0 Hz), 6.79–6.67 (m, 3H), 6.58 (d, 2H, J=11.6 Hz), 4.94 (s, 2H), 4.17–4.13 (m, 2H), 3.15 (bs, 2H), 2.99 (bs, 4H), 1.94 (bs, 4H).

Example 92

N-(3-Hydroxy-benzyl)-N-[4-(2-pyrrolidin-1-yl-ethoxy)-phenyl]-benzamide

Prepared in a manner anlogous to that described in Example 91. $^1$H NMR (CDCl$_3$) δ 7.30–7.23 (m, 2H), 7.20 (d, 1H, J=10.0 Hz), 7.14–7.04 (m, 3H), 6.89 (s, 1H), 6.77–6.68 (m, 4H), 6.53 (d, 2H, J=11.6 Hz), 5.00 (s, 2H), 3.97 (t, 2H, J=8.0 Hz), 2.90 (t, 2H, J=7.6 Hz), 2.68 (bs, 4H), 1.83 (bs, 4H).

Example 93

N-(3-Hydroxy-benzyl)-N-[4-(2-pyrrolidin-1-yl-ethoxy)-phenyl]-4-trifluoromethyl-benzamide Prepared in a manner anlogous to that described in Example 91, except that during Step A, PPM (1-propanephosphonic acid cyclic anhydride, 0.05 mL of a 50% solution in ethyl acetate, 83.5 µmol) and additional DMAP were added after stirring overnight at room temperature. Stirring was continued for an additional 12 hr. $^1$H NMR (CDCl$_3$) δ 7.39 (bs, 4H), 7.06 (t, 1H, J=10.4 Hz), 6.86 (s, 1H), 6.75–6.66 (m, 4H), 6.54 (d, 2H, J=12.0 Hz), 4.99 (s, 2H), 3.99 (t, 2H, J=7.6 Hz), 2.92 (t, 2H, J=7.6 Hz), 2.69 (bs, 4H), 1.84 (bs, 4H)

Example 94

N-(3-Hydroxy-benzyl)-N-[4-(2-pyrrolidin-1-yl-ethoxy)-phenyl]-benzenesulfonamide

Prepared in a manner analogous to that described in Example 90. MS 453.1 (M+1)$^+$

Example 95

N-(3-Hydroxy-benzyl)-4-methoxy-N-[4-(2-pyrrolidin-1-yl-ethoxy)-phenyl]-benzenesulfonamide Prepared in a manner analogous to that described in Example 90. MS 483.1 (M+1)$^+$

Example 96

2-Phenyl-ethenesulfonic acid (3-hydroxy-benzyl)-[4-(2-pyrrolidin-1-yl-ethoxy)-phenyl]-amide Prepared in a manner analogous to that described in Example 90. MS 479.1 (M+1)$^+$

Example 97

2-Cyano-N-(3-hydroxy-benzyl)-N-[4-(2-pyrrolidin-1-yl-ethoxy)-phenyl]-benzenesulfonamide tyrifluoroacetate salt Step A: 2-Cyano-N-[4-(2-pyrrolidin-1-yl-ethoxy)-phenyl]-N-[3-(tetrahydro-pyran-2-yloxy)-benzyl]-benzenesulfonamide To a solution of [4-(2-pyrrolidin-1-yl-ethoxy)-phenyl]-[3-(tetrahydro-pyran-2-yloxy)-benzyl]-amine (0.091 g, 0.23 mmol) and triethylamine (0.097 mL, 0.69 mmol) in 2 mL methylene chloride was added 2-cyanobenzenesulfonyl chloride (0.093 g, 0.46 mmol). The reaction mixture was stirred at room temperature for 24 hr. Saturated aqueous sodium bicarbonate was added and the layers were separated. The aqueous layer was washed with an additional 2 mL of methylene chloride. The combined organic layers were concentrated to afford the title compound of Step A.

Step B: 2-Cyano-N-(3-hydroxy-benzyl)-N-[4-(2-pyrrolidin-1-yl-ethoxy)-phenyl]-benzenesulfonamide, trifluoroacetate salt The crude 2-cyano-N-[4-(2-pyrrolidin-1-yl-ethoxy)-phenyl]-N-[3-(tetrahydropyran-2-yloxy)-benzyl]-benzenesulfonamide prepared in Step A was suspended in 3 mL of a 3:1 (v/v) mixture of ethanol:1N HCl and was stirred at room temperature for 24 hr. The reaction mixture was quenched with saturated aqueous sodium bicarbonate and the aqueous solution was washed with two portions of methylene chloride. The combined organic layers were concentrated. The residue was purified by reverse phase HPLC (98:2 water:0.1% trifluoroacetic acid to 98:2 acetonitrile:water) to afford the title compound. MS 478.2 (M+1)$^+$ Example 98

N-(3-Hydroxy-benzyl)-2-methyl-N-[4-(2-pyrrolidin-1-yl-ethoxy)-phenyl]-benzenesulfonamide, trifluoroacetate salt Prepared in a manner analogous to that described in Example 97. MS 467.2 (M+1)$^+$ Example 99

N-(3-Hydroxy-benzyl)-N-[4-(2-pyrrolidin-1-yl-ethoxy)-phenyl]-2-trifluoromethoxy-benzenesulfonamide, trifluoroacetate salt Prepared in a manner analogous to that described in Example 97. MS 537.1 (M+1)$^+$ Example 100

2-Fluoro-N-(3-hydroxy-benzyl)-N-[4-(2-pyrrolidin-1-yl-ethoxy)-phenyl]-benzenesulfonamide, trifluoroacetate salt Prepared in a manner analogous to that described in Example 97. MS 471.1 (M+1)$^+$ Example 101

3-Fluoro-N-(3-hydroxy-benzyl)-N-[4-(2-pyrrolidin-1-yl-ethoxy)-phenyl]-benzenesulfonamide, trifluoroacetate salt Prepared in a manner analogous to that described in Example 97. MS 471.1 (M+1)$^+$ Example 102

3-Chloro-N-(3-hydroxy-benzyl)-N-[4-(2-pyrrolidin-1-yl-ethoxy)-phenyl]-benzenesulfonamide, trifluoroacetate salt Prepared in a manner anlogous to that described in Example 97. MS 487.1 (M+1)$^+$ Example 103

N-(3-Hydroxy-benzyl)-3-methyl-N-[4-(2-pyrrolidin-1-yl-ethoxy)-phenyl]-benzenesulfonamide, trifluoroacetate salt Prepared in a manner analogous to that described in Example 97. MS 467.2 (M+1)$^+$ Example 104

N-(3-Hydroxy-benzyl)-N-[4-(2-pyrrolidin-1-yl-ethoxy)-phenyl]-3-trifluoromethyl-benzenesulfonamide, trifluoroacetate salt Prepared in a manner analogous to that described in Example 97. MS 521.1 (M+1)$^+$ Example 105

N-(3-Hydroxy-benzyl)-N-[4-(2-pyrrolidin-1-yl-ethoxy)-phenyl]-4-trifluoromethyl-benzenesulfonamide, trifluoroacetate salt Prepared in a manner analogous to that described in Example 97. MS 521.1 (M+1)$^+$ Example 106

N-(3-Hydroxy-benzyl)-N-[4-(2-pyrrolidin-1-yl-ethoxy)-phenyl]-4-trifluoromethoxy-benzenesulfonamide, trifluoroacetate salt Prepared in a manner analogous to that described in Example 97. MS 537.1 (M+1)$^+$ Example 107

4-Fluoro-N-(3-hydroxy-benzyl)-N-[4-(2-pyrrolidin-1-yl-ethoxy)-phenyl]-benzenesulfonamide, trifluoroacetate salt Prepared in a manner analogous to that described in Example 97. MS 471.1 (M+1)$^+$ Example 108

4-Chloro-N-(3-hydroxy-benzyl)-N-[4-(2-pyrrolidin-1-yl-ethoxy)-phenyl]-benzenesulfonamide, trifluoroacetate salt Prepared in a manner analogous to that described in Example 97. MS 487.1 (M+1)$^+$ Example 109

N-(3-Hydroxy-benzyl)-2,4,6-trimethyl-N-[4-(2-pyrrolidin-1-yl-ethoxy)-phenyl]-benzenesulfonamide, trifluoroacetate salt Prepared in a manner analogous to that described in Example 97. MS 495.2 (M+1)$^+$

Example 109A

N-(3-Hydroxy-benzyl)-2,4,6-trimethyl-N-[4-(2-pyrrolidin-1-yl-ethoxy)-phenyl]-benzenesulfonamide, hydrochloride salt Step A: 2.4.6-Trimethyl-N-[4-(2-pyrrolidin-1-yl-ethoxy)-phenyl]-N-[3-(tetrahydro-pyran-2-yloxy)-benzyl]-benzenesulfonamide To a solution of [4-(2-pyrrolidin-1-yl-ethoxy)-phenyl]-[3-tetrahydro-pyran-2-yloxy)-benzyl]-amine (6.5 g, 16.4 mmol) and triethylamine (6.9 mL, 49.2 mmol) in dichloromethane (80 mL) was added mesitylene sulfonyl chloride (7.17 g, 32.8 mmol). The reaction mixture was stirred at room temperature overnight. The reaction mixture was diluted with dichloromethane (100 mL) and washed with saturated aqueous sodium bicarbonate solution (80 mL). The aqueous layer was further extracted with dichloromethane (2×50 mL). The combined extracts were dried over magnesium sulfate, filtered, and concentrated in vacuo. The residue was purified by flash chromatography (silica gel, 5% methanol/dichloromethane to 10% methanol/dichloromethane) to give the title compound of Step A (7.84 g, 13.5 mmol 84% yield).

Step B: N-(3-hydroxy-benzyl)-2,4,6-trimethyl-N-[4-(2-pyrrolidin-1-Yl-ethoxy)-phenyl]-benzenesulfonamide, hydrochloride salt A solution of 2,4,6-trimethyl-N-[4-(2-pyrrolidin-1-yl-ethoxy)-phenyl]-N-[3-(tetrahydro-pyran-2-yloxy)-benzyl]-benzenesulfonamide (7.80 g, 13.5 mmol) in 1N hydrochloric acid (60 mL) and ethanol (39 mL) was stirred at room temperature overnight. The reaction mixture was neutralized to pH 7 with saturated aqueous sodium bicarbonate solution and extracted with dichloromethane (3×100 mL). The combined extracts were dried over magnesium sulfate, filtered, and concentrated in vacuo. The residue was purified by flash chromatography (silica gel, 5% methanol/dichloromethane) to afford the title free base (5.2 g, 10.5 mmol, 78% yield).

To a solution of N-(3-hydroxy-benzyl)-2,4,6-trimethyl-N-[4-(2-pyrrolidin-1-yl-ethoxy)-phenyl]-benzenesulfonamide (2.38 g, 4.81 mmol) in tetrahydrofuran (30 mL) was added 1M hydrochloric acid as a solution in diethyl ether (5.53 mL, 5.53 mmol). The mixture was stirred at room temperature for 30 min., upon which it was concentrated in vacuo to give the title hydrochloride salt.

Example 110

3,5-Dichloro-N-(3-hydroxy-benzyl)-N-[4-(2-pyrrolidin-1-yl-ethoxy)-phenyl]-benzenesulfonamide, trifluoroacetate salt Prepared in a manner analogous to that described in Example 97. MS 521.0 (M+1)$^+$

Example 111

N-(3-Hydroxy-benzyl)-2,5-dimethyl-N-[4-(2-pyrrolidin-1-yl-ethoxy)-phenyl]-benzenesulfonamide, trifluoroacetate salt Prepared in a manner analogous to that described in Example 97. MS 481.2 (M+1)$^+$

Example 112

Naphthalene-1-sulfonic acid (3-hydroxy-benzyl)-[4-(2-pyrrolidin-1-yl-ethoxy)-phenyl]-amide, trifluoroacetate salt Prepared in a manner analogous to that described in Example 97. MS 503.1 (M+1)$^+$

Example 113

Naphthalene-2-sulfonic acid (3-hydroxy-benzyl)-[4-(2-pyrrolidin-1-yl-ethoxy)-phenyl]-amide, trifluoroacetate salt Prepared in a manner analogous to that described in Example 97. MS 503.1 (M+1)$^+$

Example 114

2,4,5-Trichloro-N-(3-hydroxy-benzyl)-N-[4-(2-pyrrolidin-1-yl-ethoxy)-phenyl]-benzenesulfonamide Prepared in a manner analogous to that described in Example 91. MS 556.8 (M+1)$^+$

Example 115

2,4-Difluoro-N-(3-hydroxy-benzyl)-N-[4-(2-pyrrolidin-1-yl-ethoxy)-phenyl]-benzenesulfonamide Prepared in a manner analogous to that described in Example 91. MS 489.3 (M+1)$^+$

Example 116

2,4-Dichloro-N-(3-hydroxy-benzyl)-5-methyl-N-[4-(2-pyrrolidin-1-yl-ethoxy)-phenyl]-benzenesulfonamide Prepared in a manner analogous to that described in Example 91. MS 537.3 (M+1)$^+$

Example 117

4-Chloro-N-(3-hydroxy-benzyl)-2,5-dimethyl-N-[4-(2-pyrrolidin-1-yl-ethoxy)-phenyl]-benzenesulfonamide Prepared in a manner analogous to that described in Example 91. MS 515.3 (M+1)$^+$

Example 118

2-Chloro-4-fluoro-N-(3-hydroxy-benzyl)-N-[4-(2-pyrrolidin-1-yl-ethoxy)-phenyl]-benzenesulfonamide Prepared in a manner analogous to that described in Example 91. MS 505.3 (M+1)$^+$

Example 119

2,4,6-Trichloro-N-(3-hydroxy-benzyl)-N-[4-(2-pyrrolidin-1-yl-ethoxy)-phenyl]-benzenesulfonamide Prepared in a manner analogous to that described in Example 91. MS 557.4 (M+1)$^+$

Example 120

2-Chloro-N-(3-hydroxy-benzyl)-N-[4-(2-pyrrolidin-1-yl-ethoxy)-phenyl]-4-trifluoromethyl-benzenesulfonamide Prepared in a manner analogous to that described in Example 91. MS 555.2 (M+1)$^+$

Example 121

2,4-Dichloro-N-(3-hydroxy-benzyl)-N-[4-(2-pyrrolidin-1-yl-ethoxy)-phenyl]-benzenesulfonamide Prepared in a manner analogous to that described in Example 91. MS 521.2 (M+1)$^+$

Example 122

N-(3-Hydroxy-benzyl)-2,4,6-triisopropyl-N-[4-(2-pyrrolidin-1-yl-ethoxy)-phenyl]-benzenesulfonamide Prepared in a manner analogous to that described in Example 91. MS 579.5 (M+1)$^+$

Example 123

2,3,4,5,6-Pentafluoro-N-(3-hydroxy-benzyl)-N-[4-(2-pyrrolidin-1-yl-ethoxy)-phenyl]-benzenesulfonamide Prepared in a manner analogous to that described in Example 91. MS 543.3 (M+1)$^+$

Example 124

4-Bromo-N-(3-hydroxy-benzyl)-N-[4-(2-pyrrolidin-1-yl-ethoxy)-phenyl]-2-trifluoromethoxy-benzenesulfonamide Step A: 4-Bromo-N-[4-(2-pyrrolidin-1-yl-ethoxy)-phenyl]-N-[3-(tetrahydro-pyran-2-yloxy)-benzyl]-2-trifluoromethoxy-benzenesulfonamide To a solution of [4-(2-pyrrolidin-1-yl-ethoxy)-phenyl]-[3-(tetrahydro-pyran-2-yloxy)-benzyl]-amine (0.060 g, 0.15 mmol) in 0.4 mL methylene chloride was added triethylamine (0.06 mL, 0.45 mmol) and 4-bromo-2-trifluoromethoxybenzenesulfonyl chloride (0.103 g, 0.3 mmol). The reaction mixture was stirred at room temperature for 24 hr. PS-isocyanate resin (0.050 g) and PS-trisamine resin (0.050 g) were added and the reaction mixture was stirred for 2 hr. at room temperature. The resin was filtered off with the aid of methylene chloride. The filtrate was concentrated to afford the title compound of Step A (0.106 g). MS 700.8 (M+1)$^+$ Step B: 4-Bromo-N-(3-hydroxy-benzyl)-N-[4-(2-pyrrolidin-1-yl-ethoxy)-phenyl]-2-trifluoromethoxy-benzenesulfonamide To a solution of 4-bromo-N-[4-(2-pyrrolidin-1-yl-ethoxy)-phenyl]-N-[3-(tetrahydro-pyran-2-yloxy)-benzyl]-2-trifluoromethoxy-benzenesulfonamide (0.106 g, 0.15 mmol) in 4 mL ethanol was added 0.8 mL of 1.2N HCl. The reaction mixture was stirred at room temperature for 6 days and was diluted with 10 mL saturated aqueous sodium bicarbonate. The aqueous solution was washed with methylene chloride (2×10 mL). The combined organic layers were dried (sodium sulfate), filtered, and concentrated in vacuo. The residue was purified by preparative TLC (1.0 mm silica gel layer, eluting with 10% methanol/ethyl acetate) to afford 0.030 g (29%) of 4-bromo-N-(3-hydroxy-benzyl)-N-[4-(2-pyrrolidin-1-yl-ethoxy)-phenyl]-2-trifluoromethoxy-benzenesulfonamide. MS 617.3 (M+1)$^+$

Example 125

N-(3-Hydroxy-benzyl)-2,3,4,5,6-pentamethyl-N-[4-(2-pyrrolidin-1-yl-ethoxy)-phenyl]-benzenesulfonamide Prepared in a manner analogous to that described in Example 124. MS 523.5 (M+1)$^+$

Example 126

4-Bromo-2,5-difluoro-N-(3-hydroxy-benzyl)-N-[4-(2-pyrrolidin-1-yl-ethoxy)-phenyl]-benzenesulfonamide Prepared in a manner analogous to that described in Example 124. MS 569.1 (M+1)$^+$

Example 127

2,3,4-Trifluoro-N-(3-hydroxy-benzyl)-N-[4-(2-pyrrolidin-1-yl-ethoxy)-phenyl]-benzenesulfonamide Prepared in a manner analogous to that described in Example 124. MS 507.3 (M+1)$^+$

Example 128

4-Bromo-2-ethyl-N-(3-hydroxy-benzyl)-N-[4-(2-pyrrolidin-1-yl-ethoxy)-phenyl]-benzenesulfonamide Prepared in a manner analogous to that described in Example 124. MS 561.3 (M+1)$^+$

Example 129

2,4-Dichloro-N-(3-hydroxy-benzyl)-6-methyl-N-[4-(2-pyrrolidin-1-yl-ethoxy)-phenyl]-benzenesulfonamide Prepared in a manner analogous to that described in Example 124. MS 535.2 (M+1)$^+$

Example 130

4-Bromo-N-(3-hydroxy-benzyl)-2-methyl-N-[4-(2-pyrrolidin-1-yl-ethoxy)-phenyl]-benzenesulfonamide Prepared in a manner analogous to that described in Example 124. MS 547.2 (M+1)$^+$

Example 131

2,6-Dichloro-N-(3-hydroxy-benzyl)-N-[4-(2-pyrrolidin-1-yl-ethoxy)-phenyl]-4-trifluoromethyl-benzenesulfonamide Prepared in a manner analogous to that described in Example 124. MS 589.2 (M+1)$^+$

Example 132

5-Chloro-thiophene-2-sulfonic acid (3-hydroxy-benzyl)-[4-(2-pyrrolidin-1-yl-ethoxy)-phenyl]-amide Prepared in a manner analogous to that described in Example 91. MS 493.3 $(M+1)^+$

Example 133

-3,5-Dimethyl-isoxazole-4-sulfonic acid (3-hydroxy-benzyl)-[4-(2-pyrrolidin-1-yl-ethoxy)-phenyl]-amide Prepared in a manner analogous to that described in Example 91. MS 472.3 $(M+1)^+$

Example 134

2-Chloro-4-cyano-N-(3-hydroxy-benzyl)-N-[4-(2-pyrrolidin-1-yl-ethoxy)-phenyl]-benzenesulfonamide Prepared in a manner analogous to that described in Example 91. MS 512.3 $(M+1)^+$

Example 135

N-(3-Hydroxy-benzyl)-2,4-dimethyl-N-[4-(2-pyrrolidin-1-yl-ethoxy)-phenyl]-benzenesulfonamide Prepared in a manner analogous to that described in Example 91. MS 481.4 $(M+1)^+$

Example 136

2,3,4-Trichloro-N-(3-hydroxy-benzyl)-N-[4-(2-pyrrolidin-1-yl-ethoxy)-Phenyl]-benzenesulfonamide Prepared in a manner analogous to that described in Example 91. MS 557.4 $(M+1)^+$

Example 137

2,4,5-Trifluoro-N-(3-hydroxy-benzyl)-N-[4-(2-pyrrolidin-1-yl-ethoxy)-phenyl]-benzenesulfonamide Prepared in a manner analogous to that described in Example 91. MS 507.5 $(M+1)^+$

Example 138

4-Bromo-N-(3-hydroxy-benzyl)-N-[4-(2-pyrrolidin-1-yl-ethoxy)-phenyl]-benzenesulfonamide Prepared in a manner analogous to that described in Example 124. MS 533.2 $(M+1)^+$

Example 139

N-(4-{(3-Hydroxy-benzyl)-[4-(2-pyrrolidin-1-yl-ethoxy)-phenyl]-sulfamoyl}-phenyl)-acetamide Prepared in a manner analogous to that described in Example 124. MS 510.4 $(M+1)^+$

Example 140

4-tert-Butyl-N-(3-hydroxy-benzyl)-N-[4-(2-pyrrolidin-1-yl-ethoxy)-phenyl]-benzenesulfonamide Prepared in a manner analogous to that described in Example 124. MS 509.4 $(M+1)^+$

Example 141

4-Cyano-N-(3-hydroxy-benzyl)-N-[4-(2-pyrrolidin-1-yl-ethoxy)-phenyl]-benzenesulfonamide Prepared in a manner analogous to that described in Example 124. MS 478.3 $(M+1)^+$

Example 142

4-Ethyl-N-(3-hydroxy-benzyl)-N-[4-(2-pyrrolidin-1-yl-ethoxy)-phenyl]-benzenesulfonamide Prepared in a manner analogous to that described in Example 124. MS 481.3 $(M+1)^+$

Example 143

N-(3-Hydroxy-benzyl)-4-propyl-N-[4-(2-pyrrolidin-1-yl-ethoxy)-phenyl]-benzenesulfonamide Prepared in a manner analogous to that described in Example 124. MS 495.4 $(M+1)^+$

Example 144

N-(3-Hydroxy-benzyl)-4-isopropyl-N-[4-(2-pyrrolidin-1-yl-ethoxy)-phenyl]-benzenesulfonamide Prepared in a manner analogous to that described in Example 124. MS 495.4 $(M+1)^+$

Example 145

N-(3-Hydroxy-benzyl)-4-methyl-N-[4-(2-pyrrolidin-1-yl-ethoxy)-phenyl]-benzenesulfonamide Prepared in a manner analogous to that described in Example 124. MS 467.3 $(M+1)^+$

Example 146

Cyclohexanecarboxylic acid (3-fluoro-benzyl)-[4-(2-pyrrolidin-1-yl-ethoxy)-phenyl]-amide Step A: Cyclohexanecarboxylic acid [4-(2-pyrrolidin-1-yl-ethoxy)-phenyl]-amide To a solution of 4-(2-pyrrolidin-1-yl-ethoxy)-phenylamine (2.15 g, 10.42 mmol) and triethylamine (3.27 mL, 23.4 mmol) in 100 mL methylene chloride at 0° C. was added cyclohexanecarbonyl chloride (1.46 mL, 10.94 mmol), dropwise. The reaction mixture was stirred at room temperature for 24 hr. Saturated aqueous sodium bicarbonate was added and the layers were separated. The aqueous layer was washed with 50 mL methylene chloride. The combined organic layers were dried (magnesium sulfate), filtered, and concentrated to afford the title compound of Step A. MS 317.2 $(M+1)^+$ Step B: Cyclohexanecarboxylic acid (3-fluoro-benzyl)-[4-(2-pyrrolidin-1-yl-ethoxy)-phenyl]-amide To a solution of cyclohexanecarboxylic acid (4-(2-pyrrolidin-1-yl-ethoxy)phenyl]-amide (0.250 g, 0.79 mmol) in 5 mL N,N-dimethylformamide at 0° C. was added sodium hydride (0.041 g of a 60% dispersion in mineral oil, 1.03 mmol). The reaction mixture was stirred at 0° C. for 5 minutes and 3-fluorobenzyl bromide (0.117 mL, 0.95 mmol) was added. The reaction mixture was stirred at room temperature for 24 hr. and water was added. The aqueous solution was washed with ethyl acetate (2×). The combined organic layers were dried (magnesium sulfate), filtered, and concentrated. Medium pressure silica gel chromatography (methylene chloride to 5% methanol/methylene chloride) afforded the title compound. MS 425.2 $(M+1)^+$ Example 147

N-(3-Hydroxy-benzyl)-2,4,6-trimethyl-N-[4-(2-piperidin-1-yl-ethoxy)-phenyl]-benzenesulfonamide Step A: (4-Benzyloxy-phenyl)-[3-(tetrahydro-pyran-2-yloxy)-benzylidenel-amine To a solution of 3-(tetrahydro-pyran-2-yloxy)-benzaldehyde (11.3 g, 54.8 mmol) in 200 mL methylene chloride was added 4-benzyloxyaniline (10.9 g, 54.8 mmol) and magnesium sulfate (70 g, 582 mmol). The reaction mixture was stirred at room temperature for 24 hr. The magnesium sulfate was filtered off with the aid of methylene chloride (2×100 mL). The filtrate was concentrated to afford 21.0 g of the title compound of Step A.

Step B: (4-Benzyloxy-phenyl)-[3-(tetrahydro-pyran-2-yloxy)-benzyl]-amine

To a solution of (4-benzyloxy-phenyl)-[3-(tetrahydro-pyran-2-yloxy)-benzylidene]-amine (21.0 g, 54.2 mmol) in 350 mL methanol and 150 mL methylene chloride at 0° C. was added sodium borohydride (3.3 g, 86.7 mmol) in portions over 20 minutes. The reaction mixture was stirred at 0° C. for 1 hr. and at room temperature for 3 days. Saturated aqueous sodium bicarbonate (250 mL) was added and the aqueous solution was washed with methylene chloride (3×500 mL). The combined organic layers were washed with 500 mL saturated aqueous sodium chloride, dried (magnesium sulfate), filtered, and concentrated to afford 20.6 of the title compound of Step B.

Step C: N-(4-Benzyloxy-phenyl)-2,4,6-trimethyl-N-[3-(tetrahydro-pyran-2-yloxy)-benzyl]-benzenesulfonamide To a solution of (4-benzyloxy-phenyl)-[3-(tetrahydro-pyran-2-yloxy)-benzyl]-amine (12.7 g, 32.6 mmol) in 25 mL methylene chloride at 0° C. was added triethylamine (14.0 mL, 97.8 mmol), DMAP (0.400 g, 3.27 mmol) and 2-mesitylenesulfonyl chloride (14.3 g, 65.2 mmol). The reaction mixture was stirred at room temperature for 17 hr. The reaction mixture was diluted to a volume of 800 mL with methylene chloride and was washed with water (3×200 mL) and saturated aqueous sodium chloride (1×200 mL). The organic layer was dried (magnesium sulfate), filtered, and concentrated. Medium pressure silica gel chromatography (10% ethyl acetate/hexanes to 25% ethyl acetate/hexanes) afforded 8.82 g of the title compound of Step C.

Step D: N-(4-Hydroxy-phenyl)-2,4,6-trimethyl-N-[3-(tetrahydro-pyran-2-yloxy)-benzyl]-benzenesulfonamide To a solution of N-(4-benzyloxy-phenyl)-2,4,6-trimethyl-N-[3-(tetrahydro-pyran-2-yloxy)-benzyl]-benzenesulfonamide (7.39 g, 12.9 mol) in 300 mL methanol was added palladium black (0.800 g) and ammonium formate (8.15 g, 129 mmol). The reaction mixture was heated at reflux for 3 hr. and was cooled. The reaction mixture was filtered through diatomaceous earth with the aid of methanol (2×50 mL). The filtrate was concentrated and the residue was partitioned between 600 mL ethyl acetate and 250 mL water. The layers were separated and the organic layer was washed with water (2×300 mL) and saturated aqueous sodium chloride (1×300 mL). The organic layer was dried (magnesium sulfate), filtered, and concentrated. Medium pressure silica gel chromatography (25% ethyl acetate/hexanes) afforded 5.00 g of the title compound of Step D. MS 482.2 $(M+1)^+$ Step E: N-[4-(2-Bromo-ethoxy)-phenyl]-2,4.6-trimethyl-N-[3-(tetrahydro-pyran-2-yloxy)-benzyl]-benzenesulfonamide To a suspension of N-(4-hydroxy-phenyl)-2,4,6-trimethyl-N-[3-(tetrahydro-pyran-2-yloxy)-benzyl]-benzenesulfonamide (0.238 g, 0.49 mmol) and 1,2-dibromoethane (0.43 mL, 4.94 mmol) in 1 mL water was added sodium hydroxide (0.020 g, 0.49 mmol, dissolved in 0.1 mL of water). The reaction mixture was heated at reflux for 3 hr. and was cooled to room temperature. The reaction mixture was diluted with 10 mL water and the aqueous solution was washed with ethyl acetate (3×15 mL). The combined organic layers were washed with saturated aqueous sodium chloride, dried (magnesium sulfate), and concentrated. Medium pressure silica gel chromatography (25% ethyl acetate/hexanes) afforded 0.075 g of the title compound of Step E.

Step F: N-(3-Hydroxy-benzyl)-2,4,6-trimethyl-N-14-(2-DiDeridin-1-yl-ethoxy)-phenyl]-benzenesulfonamide To a solution of N-[4-(2-bromo-ethoxy)-phenyl]-2,4,6-trimethyl-N-[3-(tetrahydro-pyran-2-yloxy)-benzyl]-benzenesulfonamide (0.070 g, 0.12 mmol) in 2 mL tetrahydrofuran was added piperidine (0.12 mL, 1.21 mmol). The reaction mixture was stirred at room temperature for 2 hr. The reaction mixture was diluted to a volume of 30 mL with ethyl acetate and was washed with saturated aqueous sodium bicarbonate (2×15 mL) and saturated aqueous sodium chloride (1×15 mL). The organic layer was dried (magnesium sulfate) and concentrated. Medium pressure silica gel chromatography (5% methanol/methylene chloride) afforded 0.010 g of an oil. The oil was further purified by preparative TLC (0.5 mm silica gel layer, eluting with 10% methanol/methylene chloride) to afford 0.003 g of the title compound. MS 509.2 $(M+1)^+$

TABLE 4

[Structure: central N attached to (1) a benzyl group with R¹ at meta position, (2) a phenyl group para-substituted with O-CH₂-CH₂-NRᵃRᵇ, and (3) an X-R⁵ group where X bears R⁵]

| Example | X | R¹ | NRᵃRᵇ | R⁵ | MS (M + 1)⁺ or ¹H NMR |
|---|---|---|---|---|---|
| 90 | CO | OH | pyrrolidine | cyclohexyl | 423.2 |
| 91 | CO | OH | pyrrolidine | 2,4,6-trichlorophenyl | ¹H NMR (CDCl₃) δ 7.13 (s, 2H), 7.10–7.05 (m, 1H), 7.03 (d, 2H, J = 12.0 Hz), 6.79–6.67 (m, 3H), 6.58 (d, 2H, J = 11.6 Hz), 4.94 (s, 2H), 4.17–4.13 (m, 2H), 3.15 (bs, 2H), 2.99 (bs, 4H), 1.94 (bs, 4H) |
| 92 | CO | OH | pyrrolidine | Ph | ¹H NMR (CDCl₃) δ 7.30–7.23 (m, 2H), 7.20 (d, 1H, J = 10.0 Hz), 7.14–7.04 (m, 3H), 6.89 (s, 1H), 6.77–6.68 (m, 4H), 6.53 (d, 2H, J = 11.6 Hz), 5.00 (s, 2H), 3.97 (t, 2H, J = 8.0 Hz), 2.90 (t, 2H, J = 7.6 Hz), 2.68 (bs, 4H), 1.83 (bs, 4H) |
| 93 | CO | OH | pyrrolidine | 4-CF₃-Ph | ¹H NMR (CDCl₃) δ 7.39 (bs, 4H), 7.06 (t, 1H, J = 10.4 Hz), 6.86 (s, 1H), 6.75–6.66 (m, 4H), 6.54 (d, 2H, J = 12.0 Hz), 4.99 (s, 2H), 3.99 (t, 2H, J = 7.6 Hz), 2.92 (t, 2H, J = 7.6 Hz), 2.69 (bs, 4H), 1.84 (bs, 4H) |
| 94 | SO₂ | OH | pyrrolidine | Ph | 453.1 |
| 95 | SO₂ | OH | pyrrolidine | p-anisoyl | 483.1 |
| 96 | SO₂ | OH | pyrrolidine | —CH=CHPh | 479.1 |
| 97 | SO₂ | OH | pyrrolidine | 2-CN—Ph | 478.2 |
| 98 | SO₂ | OH | pyrrolidine | o-tolyl | 467.2 |
| 99 | SO₂ | OH | pyrrolidine | 2-OCF₃—Ph | 537.1 |
| 100 | SO₂ | OH | pyrrolidine | 2-F—Ph | 471.1 |
| 101 | SO₂ | OH | pyrrolidine | 3-F—Ph | 471.1 |
| 102 | SO₂ | OH | pyrrolidine | 3-Cl—Ph | 487.1 |
| 103 | SO₂ | OH | pyrrolidine | m-tolyl | 467.2 |
| 104 | SO₂ | OH | pyrrolidine | 3-CF₃—Ph | 521.1 |
| 105 | SO₂ | OH | pyrrolidine | 4-CF₃—Ph | 521.1 |
| 106 | SO₂ | OH | pyrrolidine | 4-OCF₃—Ph | 537.1 |
| 107 | SO₂ | OH | pyrrolidine | 4-F—Ph | 471.1 |
| 108 | SO₂ | OH | pyrrolidine | 4-Cl—Ph | 487.1 |
| 109 | SO₂ | OH | pyrrolidine | 2,4,6-trimethylphenyl | 495.2 |
| 110 | SO₂ | OH | pyrrolidine | 3,5-dichlorophenyl | 521.0 |
| 111 | SO₂ | OH | pyrrolidine | 2,5-dimethylphenyl | 481.2 |
| 112 | SO₂ | OH | pyrrolidine | 1-naphthyl | 503.1 |
| 113 | SO₂ | OH | pyrrolidine | 2-naphthyl | 503.1 |
| 114 | SO₂ | OH | pyrrolidine | 2,4,5-trichlorophenyl | 556.8 |
| 115 | SO₂ | OH | pyrrolidine | 2,4-difluorophenyl | 489.3 |
| 116 | SO₂ | OH | pyrrolidine | 2,4-dichloro-5-Me—Ph | 537.3 |
| 117 | SO₂ | OH | pyrrolidine | 2,5-dimethyl-4-Cl—Ph | 515.3 |
| 118 | SO₂ | OH | pyrrolidine | 2-Cl-4-F—Ph | 505.3 |
| 119 | SO₂ | OH | pyrrolidine | 2,4,6-trichlorophenyl | 557.4 |
| 120 | SO₂ | OH | pyrrolidine | 2-Cl-4-CF₃—Ph | 555.2 |
| 121 | SO₂ | OH | pyrrolidine | 2,4-dichlorophenyl | 521.2 |
| 122 | SO₂ | OH | pyrrolidine | 2,4,6-trisopropylphenyl | 579.5 |
| 123 | SO₂ | OH | pyrrolidine | 2,3,4,5,6-pentafluorophenyl | 543.3 |
| 124 | SO₂ | OH | pyrrolidine | 2-OCF₃-4-Br—Ph | 617.3 |
| 125 | SO₂ | OH | pyrrolidine | 2,3,4,5,6-pentamethylphenyl | 523.5 |
| 126 | SO₂ | OH | pyrrolidine | 2,5-difluoro-4-Br—Ph | 569.1 |
| 127 | SO₂ | OH | pyrrolidine | 2,3,4-trifluorophenyl | 507.3 |
| 128 | SO₂ | OH | pyrrolidine | 2-Et-4-Br | 561.3 |
| 129 | SO₂ | OH | pyrrolidine | 2,4-dichloro-6-Me—Ph | 535.2 |
| 130 | SO₂ | OH | pyrrolidine | 2-Me-4-Br—Ph | 547.2 |
| 131 | SO₂ | OH | pyrrolidine | 2,6-dichloro-4-CF₃—Ph | 589.2 |

TABLE 4-continued

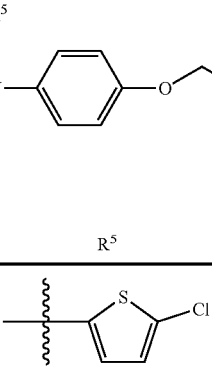

| Example | X | R¹ | NRᵃRᵇ | R⁵ | MS (M + 1)⁺ or ¹H NMR |
|---|---|---|---|---|---|
| 132 | SO₂ | OH | pyrrolidine | (5-chlorothien-2-yl) | 493.3 |
| 133 | SO₂ | OH | pyrrolidine | (3,5-dimethylisoxazol-4-yl) | 472.3 |
| 134 | SO₂ | OH | pyrrolidine | 2-Cl-4-CN-Ph | 512.3 |
| 135 | SO₂ | OH | pyrrolidine | 2,4-dimethylphenyl | 481.4 |
| 136 | SO₂ | OH | pyrrolidine | 2,3,4-trichlorophenyl | 557.4 |
| 137 | SO₂ | OH | pyrrolidine | 2,4,5-trifluorophenyl | 507.5 |
| 138 | SO₂ | OH | pyrrolidine | 4-Br-Ph | 533.2 |
| 139 | SO₂ | OH | pyrrolidine | 4-NHAc-Ph | 510.4 |
| 140 | SO₂ | OH | pyrrolidine | 4-t-butyl-Ph | 509.4 |
| 141 | SO₂ | OH | pyrrolidine | 4-CN-Ph | 478.3 |
| 142 | SO₂ | OH | pyrrolidine | 4-Et-Ph | 481.3 |
| 143 | SO₂ | OH | pyrrolidine | 4-n-propyl-Ph | 495.4 |
| 144 | SO₂ | OH | pyrrolidine | 4-i-propyl-Ph | 495.4 |
| 145 | SO₂ | OH | pyrrolidine | p-tolyl | 467.3 |
| 146 | CO | F | pyrrolidine | cyclohexyl | 425.2 |
| 147 | SO₂ | OH | piperidine | 2,4,6-trimethylphenyl | 509.2 |

EXAMPLES 148 AND 149

The compounds of the general structure

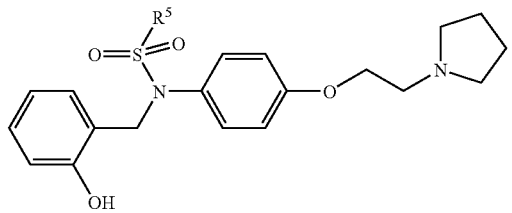

prepared according to the methods depicted in Scheme 1 hereinabove, and set forth in Table 5 hereinbelow, were prepared as disclosed in the following Examples 148 and 149.

Example 148

N-(2-Hydroxy-benzyl)-2,4,6-trimethyl-N-[4-(2-Pyrrolidin-1-yl-ethoxy)-phenyl]-benzenesulfonamide Step A: 2,4,6-Trimethyl-N-[4-(2-pyrrolidin-1-yl-ethoxy)-phenyl]-N-[2-(tetrahydro-pyran-2-yloxy)-benzyl]-benzenesulfonamide To a solution of [4-(2-pyrrolidin-1-yl-ethoxy)-phenyl]-[2-(tetrahydro-pyran-2-yloxy)-benzyl]-amine (0.060 g, 0.19 mmol) in 0.4 mL methylene chloride was added triethylamine (0.06 mL, 0.43 mmol) and 2-mesitylene sulfonyl chloride (0.066 g, 0.30 mmol). The reaction mixture was stirred at room temperature for 24 hr. PS-isocyanate resin (0.050 g), PS-trisamine resin (0.050 g), and 1.5 mL methylene chloride were added and the mixture was stirred for 2 hr. at room temperature. The resin was filtered off with the aid of methylene chloride. The filtrate was concentrated. The residue was purified by preparative TLC (1.0 mm silica gel layer, eluting with 10% methanol/methylene chloride) to afford the title compound of Step A (0.039 g). MS 579.3 (M+1)⁺

Step B: N-(2-Hydroxy-benzyl)-2,4,6-trimethyl-N-[4-(2-pyrrolidin-1-yl-ethoxy)-phenyl]-benzenesulfonamide To a solution of 2,4,6-trimethyl-N-[4-(2-pyrrolidin-1-yl-ethoxy)-phenyl]-N-[2-(tetrahydro-pyran-2-yloxy)-benzyl]-benzenesulfonamide (0.039 g, 0.07 mmol) in 4 mL absolute ethanol was added 1 mL of 1.2N HCl. The reaction mixture was stirred at room temperature for 24 hr. and was poured into saturated aqueous sodium bicarbonate. The aqueous solution was washed with two portions of ethyl acetate. The combined organic layers were dried (sodium sulfate), filtered, and concentrated. The residue was purified by preparative TLC (1.0 mm silica gel layer, eluting with 10% methanol/methylene chloride) to afford 0.004 g of the title compound. MS 494.8 (M+1)⁺

Example 149

2-Chloro-N-(2-hydroxy-benzyl)-N-[4-(2-pyrrolidin-1-yl-ethoxy)-phenyl]-benzenesulfonamide Prepared in a manner analogous to that described in Example 148. MS 488.4 (M+1)$^+$

TABLE 5

| Example | R$^5$ | MS (M + 1)$^+$ |
|---|---|---|
| 148 | 2,4,6-trimethylphenyl | 494.8 |
| 149 | 2-Cl—Ph | 488.4 |

Preparations 9 and 10

Intermediates useful in the preparation of the final compounds depicted in Scheme 2 hereinabove, and set forth in Table 6 hereinbelow, were prepared as disclosed in Preparations 9 and 10.

Preparation 9

[4-(2-Pyrrolidin-1-yl-ethoxy)-phenyl]-{1-(1-[4-tetrahydro-pyran-2-yloxy)-phenyl]-pentyl}-amine Step A: [4-(2-Pyrrolidin-1-yl-ethoxy)-phenyl]-[4-(tetrahydro-pyran-2-yloxy)-benzylidene]-amine To a solution of 4-(2-pyrrolidin-1-yl-ethoxy)-phenylamine (6.92 g, 33.5 mmol) and 4-(tetrahydro-pyran-2-yloxy)-benzaldehyde (7.25 g, 35.2 mmol) in 110 mL methylene chloride was added magnesium sulfate (14.2 g, 117.3 mmol). The reaction mixture was stirred at room temperature overnight under nitrogen. The reaction was filtered and concentrated to afford 13.3 g of the crude title compound of Step A which was used without further purification. MS 395.2 (M+1)$^+$ Step B: [4-(2-Pyrrolidin-1-yl-ethoxy)-phenyl-{1—4-(tetrahydro-pyran-2-yloxy)-phenyl]-ethyl}-amine To a solution of [4-(2-pyrrolidin-1-yl-ethoxy)-phenyl]-[4-(tetrahydro-pyran-2-yloxy)-benzylidene]-amine (1.01 g, 2.56 mmol) in 12 mL tetrahydrofuran at 0° C. was added n-BuLi (2.15 mL of a 2.5 M solution in hexanes, 5.37 mmol) dropwise. The reaction mixture was allowed to slowly warm to room temperature and was stirred overnight. The reaction mixture was poured into water and the mixture was extracted with ethyl acetate. The organic layer was dried (magnesium sulfate) and concentrated. Medium pressure silica gel chromatography (1% methanol/methylene chloride to 10% methanol/methylene chloride) afforded 0.937 g (81%) of the title compound. MS 453.2 (M+1)$^+$ Preparation 10

[4-(2-Pyrrolidin-1-yl-ethoxy)-phenyl]-{1-[4-tetrahydro-pyran-2-yloxy)-phenyl]-ethyl}-amine To a solution of [4-(2-pyrrolidin-1-yl-ethoxy)-phenyl]-[4-(tetrahydro-pyran-2-yloxy)-benzylidene]-amine (0.275 g, 0.70 mmol) (prepared in Step A of Preparation 10 above) in 5.5 mL tetrahydrofuran at 0° C. was added methyllithium (0.94 mL of a 1.6M solution in ether, 1.50 mmol) dropwise. The reaction mixture was allowed to slowly warm to room temperature and was stirred overnight. The reaction mixture was poured into water and the mixture was extracted twice with ethyl acetate. The combined organic layers were washed with saturated aqueous sodium chloride, dried (sodium sulfate), filtered, and concentrated to afford 0.306 g of the crude title compound which was used without further purification. MS 411.3 (M+1)$^+$

EXAMPLES 150 TO 152

The compounds of the general structure

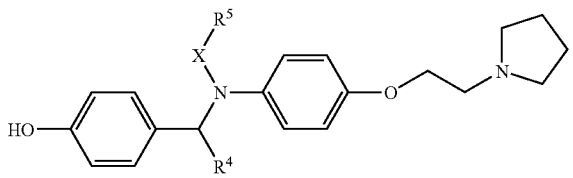

prepared according to the methods depicted in Scheme 2 hereinabove, and set forth in Table 6 hereinbelow, were prepared as disclosed in the following Examples 150 to 152.

Example 150

N-[1-(4-Hydroxy-phenyl)-ethyl]-2,4,6-trimethyl-N-[4-(2-pyrrolidin-1-yl-ethoxy)-phenyl]-benzenesulfonamide Step A: 2,4,6-Trimethyl-N-[4-(2-pyrrolidin-1-yl-ethoxy)-phenyl]-N-{1-[4-(tetrahydro-pyran-2-yloxy)-phenyl]-ethyl}-benzenesulfonamide To a solution of [4-(2-pyrrolid in-1-yl-ethoxy)-phenyl]-{1-[4-(tetrahydro-pyran-2-yloxy)-phenyl]-ethyl}-amine (0.050 g, 0.12 mmol) in 0.4 mL methylene chloride was added triethylamine (0.05 mL, 0.36 mmol) and 2-mesitylenesulfonyl chloride (0.066 g, 0.30 mmol). The reaction mixture was stirred at room temperature for 3 days. PS-isocyanate resin (0.050 g) and PS-trisamine resin (0.050 g) were added and the reaction mixture was stirred at room temperature for 45 minutes. The resin was filtered off with the aid of methylene chloride. The filtrate was concentrated to afford 0.071 g of the crude title compound of Step A which was used without further purification. MS 593.2 (M+1)$^+$ Step B: N-[1-(4-Hydroxy-phenyl)-ethyl]-2,4,6-trimethyl-N-[4-(2-pyrrolidin-1-yl-ethoxy)-phenyl]-benzenesulfonamide To a solution of crude 2,4,6-trimethyl-N-[4-(2-pyrrolidin-1-yl-ethoxy)-phenyl]-N-{1-[4-(tetrahydro-pyran-2-yloxy)-phenyl]-ethyl}-benzenesulfonamide (0.071 g, 0.12 mmol) in 4 mL absolute ethanol was added 0.8 mL of 1.2N HCl. The reaction mixture was stirred at room temperature overnight, was diluted with 10 mL saturated aqueous sodium bicarbonate, and the aqueous solution was washed with methylene chloride (3×10 mL). The combined organic layers were dried (sodium sulfate), filtered, and concentrated. The residue was purified by preparative TLC (1.0 mm silica gel layer, elution with 15% methanol/methylene chloride) to afford 0.010 g of N-[1-(4-hydroxy-phenyl)-ethyl]-2,4,6-trimethyl-N-[4-(2-pyrrolidin-1-yl-ethoxy)-phenyl]-benzenesulfonamide. MS 509.0 (M+1)$^+$ Example 151

N-[1-(4-Hydroxy-phenyl)-pentyl]-3-phenyl-N-[4-(2-pyrrolidin-1-yl-ethoxy)-phenyl]-propionamide, trifluoroacetate salt Step A: 3-Phenyl-N-[4-(2-pyrrolidin-1-yl-ethoxy)-phenyl]-N-[1-[4-(tetrahydro-pyran-2-yloxy)-phenyl]-pentyl]-propionamide To a solution of [4-(2-pyrrolidin-1-yl-ethoxy)-phenyl]-{1-[4-(tetrahydro-pyran-2-yloxy)-phenyl]-pentyl}-amine (0.100 g, 0.22 mmol) and triethylamine (0.092 mL, 0.66 mmol) in 2 mL methylene chloride was added hydrocinnamoyl chloride (0.082 mL, 0.55 mmol), dropwise. The reaction mixture was stirred for 1 hr. at room temperature. Saturated aqueous sodium bicarbonate was added and the layers were separated. The aqueous layer was extracted with an additional 2 mL of methylene chloride. The combined organic layers were concentrated to give the title compound of Step A. MS 585.1 (M+1)$^+$ Step B: N-[1-(4-Hydroxy-phenyl)-pentyl]-3-phenyl-N-[4-(2-pyrrolidin-1-yl-ethoxy)-phenyl]-propionamide, trifluoroacetate salt The crude 3-phenyl-N-[4-(2-pyrrolidin-1-yl-ethoxy)-phenyl]-N-{1-[4-(tetrahydro-pyran-2-yloxy)-phenyl]-pentyl}-propionamide was suspended in 2 mL of a 3:1 (v/v) mixture of ethanol:1N HCl and was stirred overnight at room temperature. The reaction mixture was quenched with saturated aqueous sodium bicarbonate and was extracted with two portions of methylene chloride. The combined organic layers were concentrated. The residue was purified by reverse phase HPLC (98:2H$_2$O:0.1% trifluoroacetic acid to 98:2 acetonitrile:water) to afford N-[1-(4-hydroxy-phenyl)-pentyl]-3-phenyl-N-[4-(2-pyrrolidin-1-yl-ethoxy)-phenyl)-propionamide trifluoroacetate salt. MS 501.2 (M+1)$^+$ Example 152

2-Chloro-N-[1-(4-hydroxy-phenyl)-ethyl]-N-[4-(2-pyrrolidin-1-yl-ethoxy)-phenyl]-benzenesulfonamide Step A:

To a solution of [4-(2-pyrrolidin-1-yl-ethoxy)-phenyl]-{1-[4-(tetrahydro-pyran-2-yloxy)-phenyl]-ethyl}-amine (0.062 g, 0.15 mmol) in methylene chloride (0.4 mL) was added 2-chlorobenzenesulphonyl chloride (0.063 g, 0.30 mmol) and triethylamine (62 µl, 0.45 mmol). The reaction mixture was stirred at room temperature overnight. Polymer-supported isocyanate resin (Argonaut Technologies, 0.050 g, 0.06 mmol) and polymer-supported trisamine (Argonaut Technologies, 0.050 g, 0.17 mmol) were added to the reaction. The reaction mixture was stirred for a further two hr. at room temperature, and then filtered. The crude title compound of Step A was taken directly into step B.

Step B: 2-Chloro-N-[1-(4-hydroxy-phenyl)-ethyl]-N-[4-(2-pyrrolidin-1-yl-ethoxy)-phenyl]-benzenesulfonamide To a solution of 2-chloro-N-[4-(2-pyrrolidin-1-yl-ethoxy)-phenyl]-N-{1-[4-(tetrahydro-pyran-2-yloxy)-phenyl]-ethyl}-benzenesulfonamide (0.088 g, 0.150 mmol) in absolute ethanol (4.0 mL) was added HCl (1.2N, 0.8 mL). The reaction was stirred at room temperature overnight. The reaction mixture was quenched with sat. sodium bicarbonate solution (ca. 10 mL) and extracted with methylene chloride (2×10 mL). The combined organic layers were dried (sodium sulfate), filtered and concentrated. The residue was purified by preparative TLC (SiO$_2$, 10% methanol/ethyl acetate) to afford the title compound (0.007 g, 14.6 µmol). MS 501.4 (M+1)$^+$

TABLE 6

| Example | X | R$^4$ | R$^5$ | MS (M + 1)$^+$ |
|---|---|---|---|---|
| 150 | SO$_2$ | Me | 2,4,6-trimethylphenyl | 509.0 |
| 151 | CO | n-butyl | 2-phenyl-ethyl | 501.2 |
| 152 | SO$_2$ | Me | 2-Cl—Ph | 501.4 |

Preparations 11 to 13

Intermediates useful in the preparation of the final compounds depicted in Scheme 3 hereinabove, and set forth in Table 7 hereinbelow, were prepared as disclosed in Preparations 11 to 13.

Preparation 11

N-(4-Hydroxy-benzyl)-N-[4-(3-oxo-propyl)-phenyl]-benzenesulfonate

Step A: (4-Iodo-phenyl)-[4-(tetrahydro-pyran-2-yloxy)-benzyl]-amine

To a solution of 4-(tetrahydro-pyran-2-yloxy)-benzaldehyde (9.07 g, 43.96 mmol) and 4-iodoaniline (8.87 g, 40.49 mmol) in 200 mL methylene chloride was added magnesium sulfate (26.7 g, 221.82 mmol). The reaction mixture was stirred at room temperature overnight. The reaction mixture was filtered through diatomaceous earth and the filtrate was concentrated. The residue was dissolved in 150 mL ethanol and 75 mL methanol and sodium borohydride (6 g, 158.60 mmol) was added in portions over a period of 2 hr. The reaction mixture was stirred at room temperature for an additional 2 hr. The reaction mixture was quenched with water and the aqueous solution was washed three times with methylene chloride. The combined organic extracts were dried (magnesium sulfate) and concentrated. Medium pressure silica gel chromatography (10% hexanes/ethyl acetate) followed by crystallization from methylene chloride/methanol afforded the title compound of Step A.

Step B: N-(4-Hydroxy-benzyl)-N-(4-iodo-phenyl)-benzenesulfonamide

To a solution of (4-iodo-phenyl)-[4-(tetrahydro-pyran-2-yloxy)-benzyl]-amine (3.43 g, 8.38 mmol) in 10 mL methylene chloride was added triethylamine (2.0 mL, 14.35 mmol) and benzenesulfonyl chloride (1.2 mL, 9.40 mmol). The reaction mixture was stirred at room temperature for 24 hr. The reaction mixture was quenched with water, was acidified with 1N HCl, and the aqueous solution was washed three times with methylene chloride. The combined organic extracts were washed with saturated aqueous sodium bicarbonate, dried (magnesium sulfate), filtered, and concentrated. The residue was dissolved in methanol and the solution was treated with a catalytic amount of 1N HCl. The reaction mixture was stirred at room temperature for 20 hr. The reaction mixture was made basic with saturated aqueous sodium bicarbonate and the aqueous solution was washed two times with methylene chloride. The combined organic extracts were dried (magnesium sulfate) and concentrated. Medium pressure silica gel chromatography (10% ethyl acetate/hexanes to 20% ethyl acetate/hexanes) afforded 3.21 g (82%) of the title compound of Step B.

Step C: N-(4-Hydroxy-benzyl)-N-[4-(3-oxo-propyl)-phenyl]-benzenesulfonamide

To a solution of N-(4-hydroxy-benzyl)-N-(4-iodo-phenyl)-benzenesulfonamide (3.20 g, 6.88 mmol) in 16 mL dimethylformamide was added allyl alcohol (1.20 mL, 17.60 mmol), Pd(OAc)$_2$ (0.094 g, 0.42 mmol), sodium bicarbonate (1.42 g, 16.9 mmol), and tetrabutylammonium chloride (1.95 g, 7.02 mmol). The reaction was stirred at 50° C. for 19 hr. The reaction mixture was cooled, water and ethyl acetate were added, and the mixture was filtered through diatomaceous earth. The aqueous layer was washed twice with ethyl acetate. The combined organic layers were dried (magnesium sulfate) and concentrated. Medium pressure silica gel chromatography (25% ethyl acetate/hexanes to 50% ethyl acetate/hexanes) afforded 2.12 g (78%) of N-(4-hydroxy-benzyl)-N-[4-(3-oxo-propyl)-phenyl]-benzenesulfonamide.

Preparation 12

N-(2-Chloro-4-hydroxy-benzyl)-N-(4-iodo-phenyl)-2,4,6-trimethyl-benzenesulfonate Step A: [2-Chloro-4-(tetrahydro-pyran-2-yloxy)-benzyl]-(4-iodo-phenyl)-amine To a solution of 4-iodoaniline (4.618 g, 21.1 mmol) and 2-chloro-4-(tetrahydro-pyran-2-yloxy)-benzaldehyde (5.33 g, 22.1 mmol) in 100 mL methylene chloride was added magnesium sulfate (25.38 g, 211 mmol). The reaction mixture was stirred at room temperature overnight. The magnesium sulfate was filtered off and additional magnesium sulfate (26 g) was added to the filtrate. The reaction mixture was stirred at room temperature for 3 days. The magnesium sulfate was filtered off and additional magnesium sulfate (40 g) was added to the filtrate. The reaction mixture was stirred at room temperature overnight. The reaction mixture was filtered and concentrated in vacuo. The resulting residue was dissolved in 50 mL of toluene and was heated to reflux for 3 hr., then was stirred at room temperature overnight. The toluene was removed in vacuo and the residue was crystallized from methanol/ethanol/methylene chloride. The crystalline product (9.07 g) was dissolved in 150 mL methylene chloride and 30 mL methanol and was treated with sodium borohydride (3.90 g, 103 mmol) which was added in portions. The reaction was stirred at room temperature overnight at which time saturated aqueous sodium bicarbonate was added. The mixture was extracted with methylene chloride and the organic layer was dried (magnesium sulfate), filtered, and concentrated. Medium pressure silica gel chromatography of the residue (1:1 methylene chloride: hexanes) afforded 5.97 g (64%) of the title compound of Step A.

Step B: N-[2-Chloro-4-(tetrahydro-pyran-2-yloxy)-benzyl]-N-(4-iodo-phenyl)-2,4,6-trimethyl-benzenesulfonamide To a solution of [2-chloro-4-(tetrahydro-pyran-2-yloxy)-benzyl]-(4-iodophenyl)-amine (3.00 g, 6.76 mmol) in 4 mL methylene chloride was added triethylamine (2.84 mL, 20.3 mmol) and 2-mesitylenesulfonyl chloride (2.96 g, 13.5 mmol). The reaction mixture was stirred at room temperature overnight. Additional triethylamine (1 mL, 7.15 mmol) was added and the reaction mixture was allowed to stir at room temperature overnight. DMAP was added and the reaction mixture was allowed to stir at room temperature for three days. Additional methylene chloride (2 mL), triethylamine (1 mL, 7.15 mmol) and 2-mesitylenesulfonyl chloride (1.00 g, 4.57 mmol) were added. The reaction mixture was stirred at 30° C. overnight. Additional triethylamine (2.84 mL, 20.3 mmol) and DMAP were added and the reaction was stirred at 30° C. overnight. Additional 2-mesitylenesulfonyl chloride (0.54 g, 2.47 mmol) was added and the reaction mixture was stirred at 30° C. overnight. Saturated aqueous sodium bicarbonate was added and the mixture was extracted with methylene chloride. The organic layer was dried (magnesium sulfate) and concentrated. Medium pressure silica gel chromatography of the residue afforded 2.30 g (54%) of the title compound of Step B.

Step C: N-(2-Chloro-4-hydroxy-benzyl)-N-(4-iodo-phenyl)-2,4,6-trimethyl-benzenesulfonamide To a solution of N-[2-chloro-4-(tetrahydro-pyran-2-yloxy)-benzyl]-N-(4-iodo-phenyl)-2,4,6-trimethyl-benzenesulfonamide (1.13 g, 1.80 mmol) in 1 mL tetrahydrofuran and 2 mL methanol was added HCl (4.5 mL of a 4.0 M solution in 1,4-dioxane, 18.05 mmol) and triethylsilane (2.88 mL, 18.05 mmol). The reaction mixture was stirred at room temperature overnight. Additional HCl (1 mL of a 4.0 M solution in 1,4-dioxane, 4 mmol) was added and the reaction mixture was stirred at room temperature for 2 days. Saturated aqueous sodium bicarbonate was added and the mixture was extracted with methylene chloride. The organic layer was dried (magnesium sulfate) and concentrated. Medium pressure silica gel chromatography of the residue (methylene chloride) afforded 0.70 g (72%) of the title compound of Step C.

Step D: N-(2-Chloro-4-hydroxy-benzyl)-2,4,6-trimethyl-N-[4-(3-oxo-propyl)-phenyl]-benzenesulfonamide To a solution of N-(2-chloro-4-hydroxy-benzyl)-N-(4-iodo-phenyl)-2,4,6-trimethyl-benzenesulfonamide (0.652 g, 1.20 mmol) in 6 mL dimethylformamide was added allyl alcohol (0.204 mL, 3.01 mmol), Pd(OAc)$_2$, sodium bicarbonate (0.253 g, 3.01 mmol), and tetrabutylammonium chloride (0.333 g, 1.20 mmol). The reaction mixture was stirred at 50° C. for 6 hr. and at room temperature overnight. Additional allyl alcohol (0.100 mL, 1.47 mmol), was added and the reaction mixture was stirred at 50° C. for an additional 4 hr. The reaction mixture was allowed to cool, water and ethyl acetate were added, and the mixture was filtered through diatomaceous earth. The filtrate was washed several times with water and the combined aqueous layers were extracted with ethyl acetate. The combined organic layers were dried (magnesium sulfate) and concentrated. Medium pressure silica gel chromatography of the residue (2:1 hexanes:ethyl acetate) afforded 0.52 g (92%) of the title compound.

Preparation 13

N-(3-Hydroxy-benzyl)-2,4,6-trimethyl-N-[4-(3-oxo-propyl)-phenyl]benzenesulfonate Step A: (4-iodo-phenyl)-[3-(tetrahydro-pyran-2-yloxy)-benzyl]-amine To a solution of 4-iodoaniline (11.80 g, 53.9 mmol) and 3-(tetrahydro-pyran-2-yloxy)-benzaldehyde (11.68 g, 56.6 mmol) in 100 mL methylene chloride was added magnesium sulfate (64.9 g, 539 mmol). The reaction mixture was stirred in darkness under nitrogen at room temperature overnight. The magnesium sulfate was filtered off and replaced each day for 3 days. On the fourth day, the reaction mixture was filtered and concentrated in vacuo. The resulting residue (16.45 g) was dissolved in 100 mL ethanol and 50 mL methanol and was treated with sodium borohydride (7.68 g, 202.1 mmol) which was added in portions. The reaction mixture was stirred at room temperature for 4.5 hr. at which time saturated aqueous sodium bicarbonate was added. The reaction mixture was extracted with methylene chloride and the organic layer was dried (magnesium sulfate), filtered, and concentrated. Medium pressure silica gel chromatography of the residue (10% methanol/methylene chloride) afforded 6.81 g (41%) of the title compound of Step A.

Step B: N-(4-iodo-phenyl)-2,4,6-trimethyl-N-[3-(tetrahydro-pyran-2-yloxy)-benzyl]-benzenesulfonamide To a solution of (4-iodo-phenyl)-[(3-(tetrahydro-pyran-2-yloxy)-benzyl]-amine (1.35 g, 3.30 mmol) in 2 mL methylene chloride was added triethylamine (1.38 mL, 9.90 mmol) 2-mesitylenesulfonyl chloride (1.44 g, 6.60 mmol). The reaction mixture was stirred at room temperature for 6 days. Saturated aqueous sodium bicarbonate was added and the reaction mixture was extracted with methylene chloride. The organic layer was separated and dried (magnesium sulfate), filtered, and concentrated. Medium pressure silica gel chromatography of the residue (2:1 hexanes: methylene chloride to 1:1 hexanes: methylene chloride to 1:2 hexanes: methylene chloride to ethyl acetate) afforded 1.07 g (55%) of the title compound of Step B.

Step C: N-(3-Hydroxy-benzyl)-N-(4-iodo-phenyl)-2,4,6-trimethyl-benzenesulfonamide To a solution of N-(4-iodo-phenyl)-2,4,6-trimethyl-N-[3-(tetrahydro-pyran-2-yloxy)-benzyl]-benzenesulfonamide (0.506 g, 0.86 mmol) in 5 mL tetrahydrofuran was added HCl (5.35 mL of a 4.0 M solution in 1,4-dioxane, 21.4 mmol) and triethylsilane (1.37 mL, 8.56 mmol). The reaction mixture was stirred at room temperature overnight. Saturated aqueous sodium bicarbonate was added and the mixture was extracted with methylene chloride. The organic layer was separated and concentrated. Medium pressure silica gel chromatography of the residue (methylene chloride) afforded 0.36 g (83%) of the title compound of Step C.

Step D: N-(3-Hydroxy-benzyl)-2,4,6-trimethyl-N-[4-(3-oxo-propyl)-phenyl]-benzenesulfonamide To a solution of N-(3-hydroxy-benzyl)-N-(4-iodo-phenyl)-2,4,6-trimethyl-benzenesulfonamide (0.36 g, 0.71 mmol) in 3 mL dimethylformamide was added allyl alcohol (0.121 mL, 1.77 mmol), Pd(OAc)$_2$, sodium bicarbonate (0.149 g, 1.77 mmol), and tetrabutylammonium chloride (0.197 g, 0.71 mmol). The reaction mixture was stirred at 50° C. for 24 hr. Additional allyl alcohol (0.121 mL, 1.77 mmol), Pd(OAc)$_2$, sodium bicarbonate (0.060 g, 0.71 mmol), and tetrabutylammonium chloride (0.098 g, 0.36 mmol) were added and the reaction mixture was stirred at 50° C. for an additional 24 hr. The reaction mixture was allowed to cool, water and ethyl acetate were added, and the mixture was filtered through diatomaceous earth. The filtrate was washed with water and the organic layer was dried (magnesium sulfate) and concentrated in vacuo. Medium pressure silica gel chromatography of the residue (3:1 hexanes:ethyl acetate) afforded 0.20 g (64%) of the title compound. MS 436.2 (M−1)$^+$

EXAMPLES 153 TO 168

The compounds of the general structure

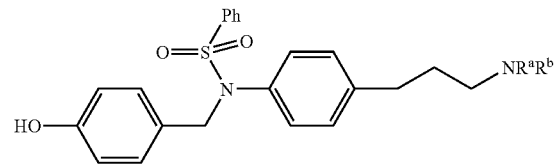

prepared according to the methods depicted in Scheme 3 hereinabove, and set forth in Table 7 hereinbelow, were prepared as disclosed in the following Examples 153 to 168.

Example 153

N-(4-Hydroxy-benzyl)-N-[4-(3-pyrrolidin-1-yl-propyl)-phenyl]-benzenesulfonamide

To a solution of N-(4-hydroxy-benzyl)-N-[4-(3-oxo-propyl)-phenyl]-benzenesulfonamide (0.093 g, 0.24 mmol) in 1.5 mL methylene chloride was added pyrrolidine (0.034 g, 0.47 mmol) and NaB(OAc)$_3$H (0.092 g, 0.44 mmol). The reaction mixture was stirred at room temperature overnight. Saturated aqueous sodium bicarbonate was added and the mixture was extracted with methylene chloride. The organic layer was dried (magnesium sulfate) and concentrated. Medium pressure chromatography (10% methanol/methylene chloride) afforded 0.053 g (50%) of the title compound. MS 451.1 (M+1)$^+$ Example 154

N-(4-Hydroxy-benzyl)-N-{4-[3-(4-hydroxy-piperidin-1-yl)-propyl]-phenyl}-benzenesulfonamide Prepared in a manner analogous to that described in Example 153. MS 481.3 (M+1)$^+$ Example 155

N-(4-Hydroxy-benzyl)-N-{4-[3-(4-phenyl-piperazin-1-yl)-propyl]-phenyl}-benzenesulfonamide Prepared in a manner analogous to that described in Example 153. MS 542.1 (M+1)$^+$ Example 156

N-{(4-[3-(3,4-Dihydro-1H-isoquinolin-2-yl)-propyl]-phenyl}-N-(4-hydroxy-benzyl)-benzenesulfonamide Prepared in a manner analogous to that described in Example 153. MS 513.3 (M+1)$^+$

Example 157

N-(4-Hydroxy-benzyl)-N-{(4-[3-(3-hydroxy-piperidin-1-yl)-pronyl]-phenyl}-benzenesulfonamide Prepared in a manner analogous to that described in Example 153. MS 481.3 (M+1)$^+$

Example 158

N-(4-Hydroxy-benzyl)-N-{4-[3-(2-hydroxymethyl-pyrrolidin-1-yl)-propyl]-phenyl}-benzenesulfonamide Prepared in a manner analogous to that described in Example 153. MS 481.2 (M+1)$^+$

Example 159

N-{4-[3-(Cyclopropvlmethyl-propyl-amino)-propyl]-phenyl}-N-(4-hydroxy-benzyl)-benzenesulfonamide Prepared in a manner analogous to that described in Example 153. MS 493.2 (M+1)$^+$

Example 160

N-(4-Hydroxy-benzyl)-N-(4-{3-[(2-hydroxy-ethyl)-methyl-amino]-propyl}-phenyl)-benzenesulfonamide Prepared in a manner analogous to that described in Example 153. MS 455.2 (M+1)$^+$

Example 161

N-{4-[3-(Benzyl-butyl-amino)-propyl]-phenyl}-N-(4-hydroxy-benzyl)-benzenesulfonamide Prepared in a manner analogous to that described in Example 153. MS 543.2 (M+1)$^+$

Example 162

N-(4-Hydroxy-benzyl)-N-{4-[3-(3-methyl-piperidin-1-yl)-propyl]-phenyl}-benzenesulfonamide Prepared in a manner analogous to that described in Example 153. MS 479.2 (M+1)$^+$

Example 163

N-{4-[3-(3,5-Dimethyl-piperidin-1-yl)-propyl]-phenyl}-N-(4-hydroxy-benzyl)-benzenesulfonamide Prepared in a manner analogous to that described in Example 153. MS 493.2 (M+1)$^+$

Example 164

N-{4-[3-(Cyclohexyl-phenyl-amino)-propyl]-phenyl}-N-(4-hydroxy-benzyl)-benzenesulfonamide Prepared in a manner analogous to that described in Example 153. MS 555.2 (M+1)$^+$

Example 165

N-{4-[3-(Cyclohexyl-methyl-amino)-propyl]-phenyl}-N-(4-hydroxy-benzyl)-benzenesulfonamide Prepared in a manner analogous to that described in Example 153. MS 493.2 (M+1)$^+$

Example 166

N-(4-Hydroxy-benzyl)-N-{4-[3-(methyl-phenethyl-amino)-propyl]-phenyl}-benzenesulfonamide Prepared in a manner analogous to that described in Example 153. MS 515.1 (M+1)$^+$

Example 167

N-[4-(3-Cyclopentylamino-propyl)-phenyl]-N-(4-hydroxy-benzyl)-benzenesulfonamide Prepared in a manner analogous to that described in Example 153. MS 465.3 (M+1)$^+$

Example 168

N-{4-[3-(4-Benzyl-piperidin-1-yl)-propyl]-phenyl}-N-(4-hydroxy-benzyl)-benzenesulfonamide Prepared in a manner analogous to that described in Example 153. MS 555.2 (M+1)$^+$

TABLE 7

| Example | NR$^a$R$^b$ | MS (M + 1)$^+$ |
| --- | --- | --- |
| 153 | pyrrolidine | 451.1 |
| 154 | 4-hydroxy-piperidine | 481.3 |
| 155 | 4-phenyl-piperazine | 542.1 |
| 156 | 1,2,3,4-tetrahydroisoquinoline | 513.3 |
| 157 | 3-hydroxy-piperidine | 481.3 |
| 158 | 2-hydroxymethyl-pyrrolidine | 481.2 |

TABLE 7-continued

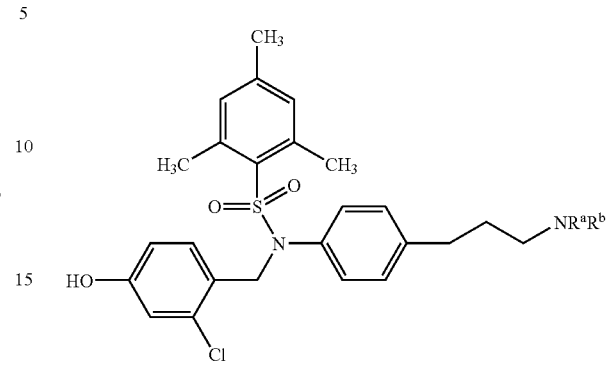

| Example | NRᵃRᵇ | MS (M + 1)⁺ |
|---|---|---|
| 159 | 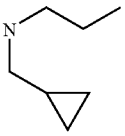 | 493.2 |
| 160 | 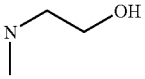 | 455.2 |
| 161 | 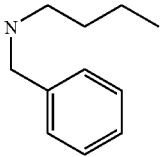 | 543.2 |
| 162 | 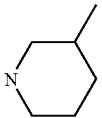 | 479.2 |
| 163 | 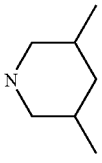 | 493.2 |
| 164 | 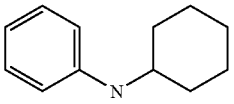 | 555.2 |
| 165 | 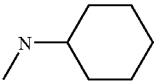 | 493.2 |
| 166 | 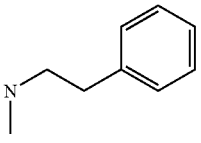 | 515.1 |
| 167 | 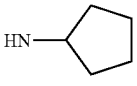 | 465.3 |
| 168 | 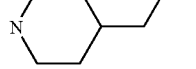 | 555.2 |

EXAMPLES 169 TO 177

The compounds of the general structure prepared according to the methods depicted in Scheme 3 hereinabove, and set forth in Table 8 hereinbelow, were prepared as disclosed in the following Examples 169 to 177.

Example 169

N-(2-Chloro-4-hydroxy-benzyl)-2,4,6-trimethyl-N-[4-(3-piperidin-1-yl-propyl)-phenyl]-benzene-sulfonamide To a solution of N-(2-chloro-4-hydroxy-benzyl)-2,4,6-trimethyl-N-[4-(3-oxo-propyl)-phenyl]-benzenesulfonamide (0.040 g, 0.08 mmol) in 0.5 mL methylene chloride was added piperidine (0.009 g, 0.11 mmol) and NaB(OAc)₃H (0.034 g, 0.16 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. Medium pressure silica gel chromatography (10% methanol/methylene chloride) afforded 0.052 g of the title compound. MS 541.1 (M+1)⁺

Example 170

N-(2-Chloro-4-hydroxy-benzyl)-2,4,6-trimethyl-N-[4-(3-thiomorpholin-4-yl-propyl)-phenyl]-benzene-sulfonamide Prepared in a manner analogous to that described in Example 169. MS 559.0 (M+1)⁺

Example 171

N-(2-Chloro-4-hydroxy-benzyl)-2,4,6-trimethyl-N-{4-[3-(2-methyl-piperidin-1-yl)-propyl]-phenyl}-benzenesulfonamide Prepared in a manner analogous to that described in Example 169. MS 554.7 (M+1)⁺

Example 172

N-(2-Chloro4-hydroxy-benzyl)-N-{4-[3-(2,6-dimethyl-morpholin-4-yl)-propyl]-phenyl}-2,4,6-trimethyl-benzenesulfonamide Prepared in a manner analogous to that described in Example 169. MS 571.1 (M+1)⁺

Example 173

N-(2-Chloro-4-hydroxy-benzyl)-2,4,6-trimethyl-N-{4-[3-(2-propyl-piperidin-1-yl)-propyl]-phenyl}-benzenesulfonamide Prepared in a manner analogous to that described in Example 169. MS 583.5 (M+1)+

Example 174

N-(2-Chloro-4-hydroxy-benzyl)-2,4,6-trimethyl-N-(4-{3-methyl-(2-pyridin-2-yl-ethyl)-amino]-propyl}-phenyl)-benzenesulfonamide Prepared in a manner analogous to that described in Example 169. MS 592.0 (M+1)+

Example 175

N-(2-Chloro-4-hdroxy-benzyl)-2,4,6-trimethyl-N-{4-[3-(4-methyl-piperidin-1-yl)-propyl]-phenyl}-benzenesulfonamide Prepared in a manner analogous to that described in Example 169. MS 555.1 (M+1)+

Example 176

(S)-N-(2-Chloro-4-hydroxy-benzyl)-N-{4-[3-(2-methoxymethyl-pyrrolidin-1-yl)-propyl]-phenyl}-2,4,6-trimethyl-benzenesulfonamide Prepared in a manner analogous to that described in Example 169. MS 571.0 (M+1)+

Example 177

(S)-1-(3-{4[(2-Chloro-4-hydroxy-benzyl)-(2,4,6-trimethyl-benzenesulfonyl)-amino]-phenyl}-propyl)-pyrrolidine-2-carboxylic acid Prepared in a manner analogous to that described in Example 169. MS 570.7 (M+1)+

TABLE 8

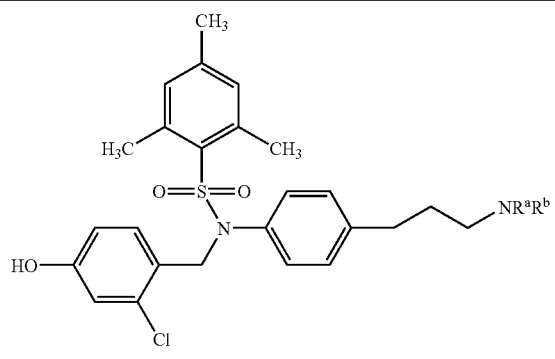

| Example | NR<sup>a</sup>R<sup>b</sup> | MS (M + 1)+ |
|---|---|---|
| 169 | piperidine | 541.1 |
| 170 | | 559.0 |

TABLE 8-continued

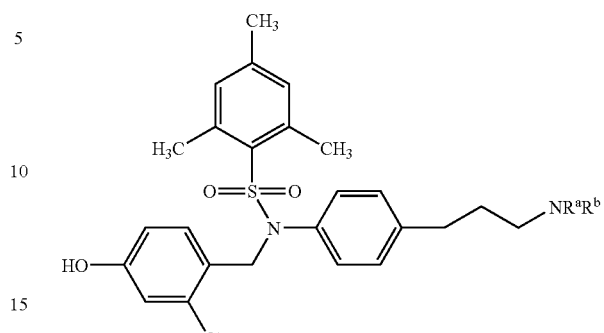

| Example | NR<sup>a</sup>R<sup>b</sup> | MS (M + 1)+ |
|---|---|---|
| 171 | | 554.7 |
| 172 | | 571.1 |
| 173 | | 583.5 |
| 174 | | 592.0 |
| 175 | | 555.1 |
| 176 | | 571.0 |
| 177 | | 570.7 |

EXAMPLES 178 TO 190

The compounds of the general structure

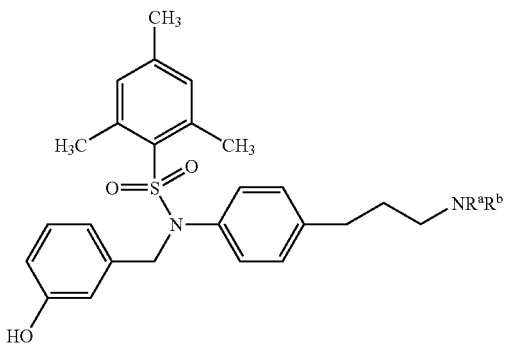

prepared according to the methods depicted in Scheme 3 hereinabove, and set forth in Table 9 hereinbelow, were prepared as disclosed in the following Examples 178 to 190.

Example 178

N-(3-Hydroxy-benzyl)-2,4,6-trimethyl-N-[4-(3-pyrrolidin-1-yl-propyl)-phenyl]-benzenesulfonamide To a solution of N-(3-hydroxy-benzyl)-2,4,6-trimethyl-N-[4-(3-oxo-propyl)-phenyl]-benzenesulfonamide (0.050 g, 0.11 mmol) in 2 mL methylene chloride was added pyrrolidine (0.010 g, 0.14 mmol) and NaB(OAc)$_3$H (0.045 g, 0.21 mmol). The reaction mixture was stirred at room temperature for three days. Saturated aqueous sodium bicarbonate was added and the aqueous solution was washed with methylene chloride. The organic layer was dried (magnesium sulfate) and concentrated. Medium pressure silica gel chromatography (15% methanolmethylene chloride) afforded 0.034 g of the title compound. MS 493.3 (M+1)$^+$

Example 179

N-(3-Hydroxy-benzyl)-2,4,6-trimethyl-N-[4-(3-morpholin-4-yl-propyl)-phenyl]-benzenesulfonamide Prepared in a manner analogous to that described in Example 178. MS 509.2 (M+1)$^+$

Example 180

(S)-N-(3-Hydroxy-benzyl)-N-{4-[3-(2-hydroxymethyl-pyrrolidin-1-yl)-propyl]phenyl}-2,4,6-trimethyl-benzenesulfonamide Prepared in a manner analogous to that described in Example 178. MS 523.2 (M+1)$^+$

Example 181

N-[4-(3-Cyclopentylamino-propyl)-phenyl]-N-(3-hydroxy-benzyl)-2,4,6-trimethyl-benzenesulfonamide Prepared in a manner analogous to that described in Example 178. MS 507.1 (M+1)$^+$

Example 182

N-(3-Hydroxy-benzyl)-2,4,6-trimethyl-N-[4-(3-thiomorpholin-4-yl-propyl)-phenyl]-benzenesulfonamide Prepared in a manner analogous to that described in Example 178. MS 525.0 (M+1)$^+$

Example 183

N-{4-[3-(2,6-Dimethyl-morpholin-4-yl)-propyl]-phenyl}-N-(3-hydroxy-benzyl)-2,4,6-trimethyl-benzenesulfonamide Prepared in a manner analogous to that described in Example 178. MS 537.1 (M+1)$^+$

Example 184

N-(3-Hydroxy-benzyl)-2,4,6-trimethyl-N-(4-{3-[methyl-(2-pyridin-2-yl-ethyl)-amino]-propyl}-phenyl)-benzenesulfonamide Prepared in a manner analogous to that described in Example 178. MS 558.2 (M+1)$^+$

Example 185

N-(3-Hydroxy-benzyl)-2,4,6-trimethyl-N-{4-[3-(4-methyl-piperidin-1-yl)-propyl]-phenyl}-benzenesulfonamide Prepared in a manner analogous to that described in Example 178. MS 521.3 (M+1)$^+$

Example 186

N-(3-Hydroxy-benzyl)-2,4,6-trimethyl-N-{4-[3-(2-propyl-piperidin-1-yl)-propyl]-phenyl}-benzenesulfonamide Prepared in a manner analogous to that described in Example 178. MS 549.2 (M+1)$^+$

Example 187

N-(3-Hydroxy-benzyl)-2,4,6-trimethyl-N-{4-[3-(2-methyl-piperidin-1-yl)-propyl]-phenyl}-benzenesulfonamide Prepared in a manner analogous to that described in Example 178. MS 521.1 (M+1)$^+$

Example 188

N-(3-Hydroxy-benzyl)-2,4,6-trimethyl-N-{4-[3-(2-methyl-pyrrolidin-1-yl)-propyl]-phenyl}-benzenesulfonamide Prepared in a manner analogous to that described in Example 178. MS 507.1 (M+1)$^+$

Example 189

N-(3-Hydroxy-benzyl)-2,4,6-trimethyl-N-[4-(3-piperidin-1-yl-propyl)-phenyl]-benzenesulfonamide Prepared in a manner analogous to that described in Example 178. MS 507.1 (M+1)$^+$

Example 190

N-{4-[3-(2,6-Dimethyl-piperidin-1-yl)-propyl]-phenyl}-N-(3-hydroxy-benzyl)-2,4,6-trimethyl-benzenesulfonamide Prepared in a manner analogous to that described in Example 178. MS 535.1 (M+1)+

TABLE 9

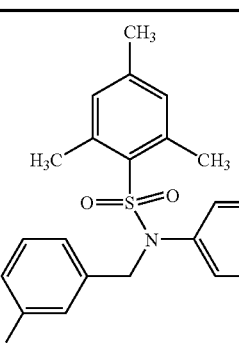

| Example | NR<sup>a</sup>R<sup>b</sup> | MS (M + 1)+ |
|---|---|---|
| 178 | pyrrolidinyl | 493.3 |
| 179 | morpholinyl | 509.2 |
| 180 | (2-hydroxymethyl-pyrrolidinyl) | 523.2 |
| 181 | (cyclopentylamino) | 507.1 |
| 182 | (thiomorpholinyl) | 525.0 |
| 183 | (2,6-dimethylmorpholinyl) | 537.1 |
| 184 | (N-[2-(pyridin-2-yl)ethyl]amino) | 558.2 |
| 185 | (4-methylpiperidinyl) | 521.3 |
| 186 | (2-ethylpiperidinyl) | 549.2 |

TABLE 9-continued

| Example | NR<sup>a</sup>R<sup>b</sup> | MS (M + 1)+ |
|---|---|---|
| 187 | (2-methylpiperidinyl) | 521.1 |
| 188 | (2-methylpyrrolidinyl) | 507.1 |
| 189 | piperidinyl | 507.1 |
| 190 | (2,6-dimethylpiperidinyl) | 535.1 |

Intermediates useful in the preparation of the final compounds depicted in Scheme 4 Hereinabove, and set forth in Table 10 hereinbelow, were prepared as disclosed in Preparation 14.

Preparation 14

3-{4-[[3-(Tetrahydro-pyran-2-yloxy)-benzyl]-(2,4,6-trimethyl-benzenesulfonyl)-amino]-phenyl}-acrylic acid Step A: 3-{4-[[3-(Tetrahydro-pyran-2-yloxy)-benzyl]-(2,4,6-trimethyl-benzenesulfonyl)-amino]-phenyl}-acrylic acid To a solution of N-(4-iodo-phenyl)-2,4,6-trimethyl-N-[3-(tetrahydro-pyran-2yloxy)-benzyl]-benzenesulfonamide (1.06 g, 1.79 mmol) in dimethylformamide was added acrylic acid methyl ester (0.81 mL, 8.95 mmol), triethylamine (0.75 mL, 5.37 mmol), and palladium tetrakistriphenylphosphine (0.103 g, 0.09 mmol). The reaction mixture was stirred at 100° C. overnight. The reaction mixture was allowed to cool to room temperature and was poured into water. The reaction mixture was extracted with ethyl acetate and the organic layer was dried (magnesium sulfate) and concentrated. Medium pressure silica gel chromatography of the residue (1:1 hexanes:methylene chloride to methylene chloride to 20% ethyl acetate/methylene chloride) afforded 0.93 g (94%) of the title compound of Step A.

Step B: 3-{4-[[3-(Tetrahydro-pyran-2-yloxy)-benzyl]-(2,4,6-trimethyl-benzenesulfonyl)-amino]-phenyl}-acrylic acid To a solution of 3-{4-[[3-(tetrahydro-pyran-2-yloxy)-benzyl]-(2,4,6-trimethyl-benzenesulfonyl)-amino]-phenyl}-acrylic acid methyl ester (1.83 g, 3.33 mmol) in 4 mL tetrahydrofuran was added sodium hydroxide (0.399 g, 9.98 mmol) in 3 mL water. The reaction mixture was stirred at room temperature overnight. The reaction mixture was adjusted to a pH of 4 with 1 N HCl and ethyl acetate and water were added. The layers were separated and the organic layer was washed with two portions of water and then with saturated aqueous sodium chloride. The combined aqueous layers were back-extracted with ethyl acetate. The combined organic layers were dried (magnesium sulfate) and concentrated to afford 1.756 g (98%) of the title compound. MS 534.3 (M−1)⁻

EXAMPLES 191 TO 200

The compounds of the general structure

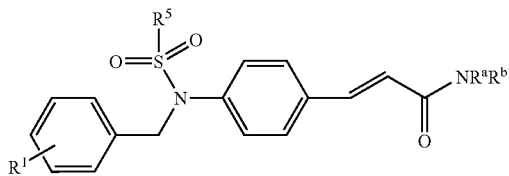

prepared according to the methods depicted in Scheme 4 hereinabove, and set forth in Table 10 hereinbelow, were prepared as disclosed in the following Examples 191 to 200

Example 191

3-{4-[(3-Hydroxy-benzyl)-(2,4,6-trimethyl-benzenesulfonyl)-amino]-phenyl}-N-(2-pyridin-4-yl-ethyl)-acrylamide Step A: N-(2-Pyridin-4-yl-ethyl)-3-{4-[[3-(tetrahydro-pyran-2-yloxy)-benzyl]-(2,4,6-trimethyl-benzenesulfonyl)-amino]-phenyl}-acrylamide A solution of 4-(2-aminoethyl)pyridine (0.017 g, 0.14 mmol) in 0.3 mL methylene chloride was added to 3-{4-[[3-(tetrahydro-pyran-2-yloxy)-benzyl]-(2,4,6-trimethyl-benzenesulfonyl)-amino]-phenyl}-acrylic acid (0.050 g, 0.09 mmol). Triethylamine (0.07 mL, 0.50 mmol), 1-propanephosphonic acid cyclic anhydride (0.06 mL of a 50 wt. % solution in ethyl acetate, 0.20 mmol), and catalytic DMAP were added. The reaction mixture was stirred at room temperature for 24 hr. Saturated aqueous sodium bicarbonate was added and the aqueous solution was washed with methylene chloride. The organic layer was separated, PS-trisamine resin (0.050 g) was added, and the mixture was stirred at room temperature for three days. The resin was filtered off and the filtrate was concentrated to afford 0.059 g of the title compound of Step A. MS 640.4 (M+1)⁺

Step B: 3-{4-[(3-Hydroxy-benzyl)-(2,4,6-trimethyl-benzenesulfonyl)-amino]-phenyl}-N-(2-pyridin-4-yl-ethyl)-acrylamide To a solution of N-(2-pyridin-4-yl-ethyl)-3-{4-[[3-(tetrahydro-pyran-2-yloxy)-benzyl]-(2,4,6-trimethyl-benzenesulfonyl)-amino]-phenyl}-acrylamide (0.059 g, 0.09 mmol) in 0.4 mL methanol and 0.1 mL tetrahydrofuran was added HCl (0.5 mL of a 4.0 M solution in 1,4-dioxane, 2 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. The residue was purified by preparative TLC (eluting with 10% methanol/methylene chloride) to afford 0.018 g of 3-{4-[(3-hydroxy-benzyl)-(2,4,6-trimethyl-benzenesulfonyl)-amino]-phenyl}-N-(2-pyridin-4-yl-ethyl)-acrylamide. ¹H NMR (CDCl₃) δ 8.32 (d, 2H, J=4.8 Hz), 7.27 (d, 1H, J=16.4 Hz), 7.18 (d, 2H, J=5.2 Hz), 7.03–6.98 (m, 4H), 6.90–6.86 (m, 4H), 6.69 (s, 2H), 6.60 (d, 1H, J=7.2 Hz), 6.24 (d, 1H, J=15.6 Hz), 4.67 (s, 2H), 3.62–3.57 (m, 2H), 2.88 (t, 2H, J=6.4 Hz), 2.41 (s, 6H), 2.24 (s, 3H).

Example 192

N-(3-Hydroxy-benzyl)-2,4,6-trimethyl-N-[4-(3-morpholin-4-yl-3-oxo-propenyl-phenyl]-benzenesulfonamide Prepared in a manner analogous to that described in Example 191. ¹H NMR (CDCl₃) δ 7.48 (d, 1H, J=15.6 Hz), 7.24–7.18 (m, 3H), 7.04–6.98 (m, 3H), 6.86 (s, 2H), 6.72–6.64 (m, 3H), 4.74 (s, 2H), 3.67 (bs, 8H), 2.44 (s, 6H), 2.25 (s, 3H).

Example 193

N-(3-Hydroxy-benzyl)-24,6-trimethyl-N-[4-(3-oxo-3-pyrrolidin-1-yl-propenyl)-phenyl]-benzenesulfonamide Step A: 2,4,6-Trimethyl-N-[4-(3-oxo-3-pyrrolidin-1-yl-propenyl)-phenyl]-N-[3-(tetrahydro-pyran-2-yloxy)-benzyl]-benzenesulfonamide A solution of pyrrolidine (11.7 μl, 0.14 mmol) in 0.3 mL methylene chloride was added to 3-{4-[[3-(tetrahydro-pyran-2-yloxy)-benzyl]-(2,4,6-trimethylbenzenesulfonyl)-amino]-phenyl}-acrylic acid (0.050 g, 0.09 mmol). Triethylamine (0.07 mL, 0.50 mmol), 1-propanephosphonic acid cyclic anhydride (0.056 mL of a 50 wt. % solution in ethyl acetate, 0.190 mmol), and catalytic DMAP were added. The reaction mixture was stirred at room temperature for 48 hr. PS-trisamine resin (0.050 g) and PS-isocyanate (0.050 g) resin was added, and the reaction mixture was stirred at room temperature for two hours. The resin was filtered off and the filtrate was concentrated. The residue was purified by preparative TLC to afford 0.021 g of the title compound of Step A.

Step B

To a solution of 2,4,6-trimethyl-N-[4-(3-oxo-3-pyrrolidin-1-yl-propenyl)-phenyl]-N-[3-(tetrahydro-pyran-2-yloxy)-benzyl]-benzenesulfonamide (0.021 g, 34.9 μmol) in 0.5 mL methanol was added HCl (0.19 mL of a 4.0 M solution in 1,4-dioxane, 2 mmol) and Et₃SiH (0.047 ml, 0.30 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. The residue was purified by preparative TLC (eluting with 10% methanol/methylene chloride) to afford 0.012 g of N-(3-hydroxybenzyl)-2,4,6-trimethyl-N-[4-(3-oxo-3-pyrrolidin-1-yl-propenyl)-phenyl]-benzenesulfonamide. ¹H NMR (acetone-d6) δ 6.16 (d, 1H, J=15.6 Hz), 6.02–5.98 (m, 2H), 5.71–5.67 (m, 3H), 5.57 (s, 2H), 5.35–5.26 (m, 4H), 3.43 (s, 2H), 2.29–2.19 (m, 4H), 1.13 (s, 6H), 0.95 (s, 3H), 0.72–0.56 (m, 4H).

Example 194

3-{4-[(3-Hydroxy-benzyl)-(2,4,6-trimethyl-benzenesulfonyl)-amino]-phenyl}-N (tetrahydro-furan-2-ylmethyl)-acrylamide Prepared in a manner analogous to that described in Example 191. $^1$H NMR (CDCl$_3$) δ 7.24 (d, 1H, J=15.2 Hz), 7.04–7.00 (m, 3H), 6.95–6.92 (m, 2H), 6.87 (s, 2H), 6.72–6.64 (m, 3H), 6.53 (bs, 1H), 6.12 (d, 1H, J=16.0 Hz), 4.75 (s, 2H), 4.08–4.03 (m, 1H), 3.91–3.81 (m, 1H), 3.79–3.75 (m, 1H), 3.70–3.64 (m, 1H), 3.24–3.18 (m, 1H), 2.45 (s, 6H), 2.26 (s, 3H), 2.05–1.87 (m, 3H), 1.60–1.53 (m, 1H).

Example 195

(R)-3-{4-[(3-Hydroxy-benzyl)-(2,4,6-trimethyl-benzenesulfonyl)-amino]-phenyl}-N-(1-phenyl-ethyl)-acrylamide Prepared in a manner analogous to that described in Example 191. $^1$H NMR (CDCl$_3$) δ 7.32–7.20 (m, 5H), 7.15 (d, 1H, J=15.6 Hz), 7.03–6.98 (m, 1H), 6.94–6.84 (m, 5H), 6.68–6.63 (m, 2H), 6.55 (bs, 2H), 6.06 (d, 1H, J=15.6 Hz), 5.20–5.17 (m, 1H), 4.66 (s, 2H), 2.45 (s, 6H), 2.26 (s, 3H). 1.50 (d, 3H, J=6.4 Hz).

Example 196

N-Biphenyl-3-ylmethyl-3-[4-{(3-hydroxy-benzyl)-(2,4,6-trimethyl-benzenesulfonyl)-amino]-phenyl}-acrylamide Prepared in a manner analogous to that described in Example 191. $^1$H NMR (CDCl$_3$) δ 7.51–7.44 (m, 4H), 7.37–7.26 (m, 4H), 7.23–7.20 (m, 1H), 7.14 (d, 1H, J=15.6 Hz), 7.02–6.95 (m, 1H), 6.90–6.83 (m, 5H), 6.66–6.61 (m, 3H), 6.53 (s, 1H), 6.01 (d, 1H, J=16.0 Hz), 4.58 (s, 2H), 4.51 (d, 2H, J=6.0 Hz), 2.41 (s, 6H), 2.23 (s, 3H).

Example 197

3-{4-[(3-Hydroxy-benzyl)-(2,4,6-trimethyl-benzenesulfonyl)-amino]-phenyl}-N-(2-morpholin-4-yl-ethyl)-acrylamide Prepared in a manner analogous to that described for Example 191. $^1$H NMR (CDCl$_3$) δ 7.36 (d, 1H, J=15.6 Hz), 7.14–7.09 (m, 2H), 7.00–6.96 (m, 1H), 6.94–6.89 (m, 2H), 6.87 (s, 2H), 6.82 (s, 1H), 6.67–6.57 (m, 2H), 6.22 (d, 1H, J=15.6 Hz), 4.78 (s, 2H), 3.86 (bs, 4H), 3.64–3.60 (m, 3H), 2.85–2.81 (m, 5H), 2.43 (s, 6H), 2.26 (s, 3H).

Example 198

3-{4-[(3-Hydroxy-benzyl)-(2,4,6-trimethyl-benzenesulfonyl)-amino]-phenyl}-N-(3-imidazol-1-yl-propyl)-acrylamide Prepared in a manner analogous to that described in Example 191. MS 559.5 (M+1)$^+$

Example 199

N-Benzhydryl-3-{4-[(3-hydroxy-benzyl)-(2,4,6-trimethyl-benzenesulfonyl)-amino]-phenyl}-acrylamide Prepared in a manner analogous to that described in Example 191, except that the product of Step B was further purified by Biotage® chromatography (SiO$_2$, 10% ethyl acetate/methylene chloride). $^1$H NMR (CDCl$_3$) δ 7.28–7.18 (m, 10H), 6.98–6.82 (m, 7H), 6.69–6.64 (m, 2H), 6.54 (d, 1H, J=7.6 Hz), 6.48 (s, 1H), 6.31 (d, 1H, J=7.6 Hz), 6.11 (d, 1H, J=15.6 Hz), 4.61 (s, 2H), 2.41 (s, 6H), 2.24 (s, 3H).

Example 200

N-(4-Hydroxy-benzyl)-4-methoxy-N-[4-(3-morpholin-4-yl-3-oxo-propenyl)-phenyl]-benzenesulfonamide Step A: 1-Morpholin-4-yl-3-{4-[4-(tetrahydro-pyran-2-yloxy)-benzylamino]-phenyl}-prop-2-en-1-one To a solution of (4-iodo-phenyl)-[4-(tetrahydro-pyran-2-yloxy)-benzyl]-amine (0.265 g, 0.65 mmol) in 2 mL dimethylformamide was added 4-acryloylmorpholine (0.110 g, 0.78 mmol), Pd(OAc)$_2$ (0.029 g, 0.13 mmol), and triethylamine (0.20 mL, 1.43 mmol). The reaction was stirred at 90° C. for 2 hr. Triphenylphosphine (0.101 g, 0.38 mmol) and additional Pd(OAc)$_2$ (0.032 g, 0.14 mmol) were added and the reaction mixture was stirred at 90–100° C. for 18 hr. The reaction mixture was cooled, water was added, and the aqueous solution was washed ethyl acetate (3×). The combined organic layers were dried (magnesium sulfate) and concentrated. Medium pressure silica gel chromatography (33% ethyl acetate/hexanes to 50% ethyl acetate/hexanes) afforded the title compound of Step A. MS 423.0 (M+1)$^+$ Step B: 4-Methoxy-N-[4-(3-morpholin-4-yl-3-oxo-propenyl)-phenyl]-N-[4-(tetrahydro-pyran-2-yloxy)-benzyl]-benzenesulfonamide To a solution of 1-morpholin-4-yl-3-{4-[4-(tetrahydro-pyran-2-yloxy)benzylamino]-phenyl}-prop-2-en-1-one (0.115 g, 0.27 mmol) and triethylamine (0.100 mL, 0.72 mmol) in 3 mL methylene chloride was added 4-methoxy-benzenesulfonyl chloride (0.065 g, 0.31 mmol). The reaction mixture was stirred at room temperature for 60 h. Water was added and the aqueous solution was washed with methylene chloride (3×). The combined organic layers were dried (magnesium sulfate) and concentrated. Medium pressure silica gel chromatography (50% ethyl acetate/hexanes) gave the title compound of Step B.

Step C: N-(4-Hydroxy-benzyl)-4-methoxy-N-[4-(3-morpholin-4-yl-3-oxo-propenyl)-phenyl]-benzenesulfonamide To a solution of 4-methoxy-N-[4-(3-morpholin-4-yl-3-oxo-propenyl)-phenyl]-N-[4-(tetrahydro-pyran-2-yloxy)-benzyl]-benzenesulfonamide (0.028 g, 0.05 mmol) in 15 mL methanol was added 5 mL of 1N HCl. The reaction mixture was stirred at room temperature for 20 hr. The reaction mixture was washed twice with methylene chloride. The combined organic layers were washed with saturated aqueous sodium bicarbonate, dried (magnesium sulfate), and concentrated. Radial chromatography (methylene chloride to 5% methanol/methylene chloride) provided N-(4-hydroxy-benzyl)-4-methoxy-N-[4-(3-morpholin-4-yl-3-oxo-propenyl)-phenyl]-benzenesulfonamide. $^1$H NMR (CDCl$_3$) δ 7.54 (d, 2H, J=9.2 Hz), 7.52 (d, 1H, J=15.2 Hz), 7.27 (d, 2H, J=8.4 Hz), 6.99 (d, 2H, J=8.4 Hz), 6.92 (d, 2H, J=8.8 Hz), 6.91 (d, 2H, J=9.2 Hz), 6.71 (d, 1H, J=15.2 Hz), 6.63 (d, 2H, J=8.4 Hz), 4.59 (s, 2H), 3.85 (s, 3H), 3.75–3.55 (m, 8H).

TABLE 10

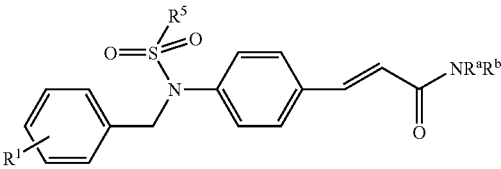

| Example | R¹ | R⁵ | NRᵃRᵇ | ¹H NMR or MS (M + 1)⁺ |
|---|---|---|---|---|
| 191 | 3-OH | 2,4,6-trimethylphenyl | 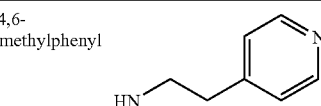 | ¹H NMR (CDCl₃) δ 8.32 (d, 2H, J = 4.8 Hz), 7.27 (d, 1H, J = 16.4 Hz), 7.18 (d, 2H, J = 5.2 Hz), 7.03–6.98 (m, 4H), 6.90–6.86 (m, 4H), 6.69 (s, 2H), 6.60 (d, 1H, J = 7.2 Hz), 6.24 (d, 1H, J = 15.6 Hz), 4.67 (s, 2H), 3.62–3.57 (m, 2H), 2.88 (t, 2H, J = 6.4 Hz), 2.41 (s, 6H), 2.24 (s, 3H). |
| 192 | 3-OH | 2,4,6-trimethylphenyl | morpholinyl | ¹H NMR (CDCl₃) δ 7.48 (d, 1H, J = 15.6 Hz), 7.24–7.18 (m, 3H), 7.04–6.98 (m, 3H), 6.86 (s, 2H), 6.72–6.64 (m, 3H), 4.74 (s, 2H), 3.67 (bs, 8H), 2.44 (s, 6H), 2.25 (s, 3H). |
| 193 | 3-OH | 2,4,6-trimethylphenyl | pyrrolidinyl | ¹H NMR (acetone-D6) δ 6.16 (d, 1H, J = 15.6 Hz), 6.02–5.98 (m, 2H), 5.71–5.67 (m, 3H), 5.57 (s, 2H), 5.35–5.26 (m, 4H), 3.43 (s, 2H), 2.29–2.19 (m, 4H), 1.13 (s, 6H), 0.95 (s, 3H), 0.72–0.56 (m, 4H). |
| 194 | 3-OH | 2,4,6-trimethylphenyl | 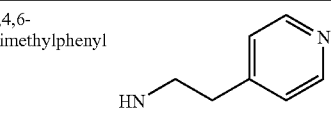 | ¹H NMR (CDCl₃) δ 7.24 (d, 1H, J = 15.2 Hz), 7.04–7.00 (m, 3H), 6.95–6.92 (m, 2H), 6.87 (s, 2H), 6.72–6.64 (m, 3H), 6.53 (bs, 1H), 6.12 (d, 1H, J = 16.0 Hz), 4.75 (s, 2H), 4.08–4.03 (m, 1H), 3.91–3.81 (m, 1H), 3.79–3.75 (m, 1H), 3.70–3.64 (m, 1H), 3.24–3.18 (m, 1H), 2.45 (s, 6H), 2.26 (s, 3H), 2.05–1.87 (m, 3H), 1.60–1.53 (m, 1H). |
| 195 | 3-OH | 2,4,6-trimethylphenyl | 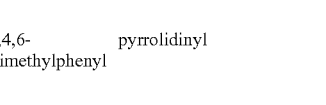 | ¹H NMR (CDCl₃) δ 7.32–7.20 (m, 5H), 7.15 (d, 1H, J = 15.6 Hz), 7.03–6.98 (m, 1H), 6.94–6.84 (m, 5H), 6.68–6.63 (m, 2H), 6.55 (bs, 2H), 6.06 (d, 1H, J = 15.6 Hz), 5.20–5.17 (m, 1H), 4.66 (s, 2H), 2.45 (s, 6H), 2.26 (s, 3H). 1.50 (d, 3H, J = 6.4 Hz). |
| 196 | 3-OH | 2,4,6-trimethylphenyl | 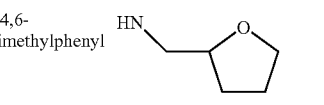 | ¹H NMR (CDCl₃) δ 7.51–7.44 (m, 4H), 7.37–7.26 (m, 4H), 7.23–7.20 (m, 1H), 7.14 (d, 1H, J = 15.6 Hz), 7.02–6.95 (m, 1H), 6.90–6.83 (m, 5H), 6.66–6.61 (m, 3H), 6.53 (s, 1H), 6.01 (d, 1H, J = 16.0 Hz), 4.58 (s, 2H), 4.51 (d, 2H, J = 6.0 Hz), 2.41 (s, 6H), 2.23 (s, 3H). |
| 197 | 3-OH | 2,4,6-trimethylphenyl |  | ¹H NMR (CDCl₃) δ 7.36 (d, 1H, J = 15.6 Hz), 7.14–7.09 (m, 2H), 7.00–6.96 (m, 1H), 6.94–6.89 (m, 2H), 6.87 (s, 2H), 6.82 (s, 1H), 6.67–6.57 (m, 2H), 6.22 (d, 1H, J = 15.6 Hz), 4.78 (s, 2H), 3.86 (bs, 4H), 3.64–3.60 (m, 3H), 2.85–2.81 (m, 5H), 2.43 (s, 6H), 2.26 (s, 3H). |
| 198 | 3-OH | 2,4,6-trimethylphenyl | 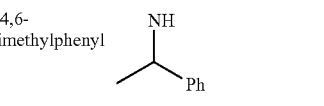 | MS 559.5 (M + 1)⁺ |

TABLE 10-continued

[Structure: sulfonamide-substituted benzyl-N-phenyl-cinnamamide scaffold with R¹ on benzyl ring, R⁵ on sulfonyl, NR^aR^b on amide]

| Example | R¹ | R⁵ | NR^aR^b | ¹H NMR or MS (M + 1)⁺ |
|---|---|---|---|---|
| 199 | 3-OH | 2,4,6-trimethylphenyl | NH-CH(Ph)(Ph) | ¹H NMR (CDCl₃) δ 7.28–7.18 (m, 10 H), 6.98–6.82 (m, 7H), 6.69–6.64 (m, 2H), 6.54 (d, 1H, J = 7.6 Hz), 6.48 (s, 1H), 6.31 (d, 1H, J = 7.6 Hz), 6.11 (d, 1H, J = 15.6 Hz), 4.61 (s, 2H), 2.41 (s, 6H), 2.24 (s, 3H). |
| 200 | 4-OH | p-anisoyl | morpholinyl | ¹H NMR (CDCl₃) δ 7.54 (d, 2H, J = 9.2 Hz), 7.52 (d, 1H, J = 15.2 Hz), 7.27 (d, 2H, J = 8.4 Hz), 6.99 (d, 2H, J = 8.4 Hz), 6.92 (d, 2H, J = 8.8 Hz), 6.91 (d, 2H, J = 9.2 Hz), 6.71 (d, 1H, J = 15.2 Hz), 6.63 (d, 2H, J = 8.4 Hz), 4.59 (s, 2H), 3.85 (s, 3H), 3.75–3.55 (m, 8H). |

Intermediates useful in the preparation of the final compounds depicted in Scheme 5 hereinabove, and set forth in Table 11 hereinbelow, were prepared as disclosed in Preparation 15.

Preparation 15

(4-Methoxy-phenyl)-[4-(tetrahydro-pyran-2-yloxy)-benzyl]-amine (XVI)

To a solution of 4-(tetrahydro-pyran-2-yloxy)-benzaldehyde (2.43 g, 11.8 mmol) and p-anisidine (1.38 g, 11.2 mmol) in 40 mL methylene chloride was added magnesium sulfate (4.72 g, 39.2 mmol). The reaction mixture was stirred at room temperature overnight under nitrogen. The reaction mixture was filtered and concentrated to yield 3.5 g (11.2 mmol) of a brown solid. The resulting solid (2.5 g, 8.03 mmol) was dissolved in 2:1 ethanol:methanol and was treated with sodium borohydride (1.22 g, 32.1 mmol) which was added in three portions over a period of 20 min. The reaction was stirred at room temperature overnight, and then quenched with saturated aqueous sodium bicarbonate. The mixture was extracted with methylene chloride and the organic layer was dried (magnesium sulfate), filtered, and concentrated. Medium pressure silica gel chromatography of the residue (5% ethyl acetate/hexanes to 20% ethyl acetate/hexanes) afforded 1.37 g (4.37 mmol) of (4-methoxy-phenyl)-[4-(tetrahydro-pyran-2-yloxy)-benzyl]-amine. MS 314.2 (M+1)⁺

The compounds of the general structure

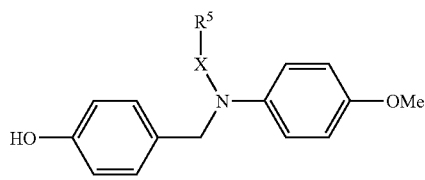

prepared according to the methods depicted in Scheme 5 hereinabove, and set forth in Table 11 hereinbelow, were prepared as disclosed in the following Examples 201 to 206.

EXAMPLES 201 TO 206

Example 201

N-(4-Hydroxy-benzyl)-N-(4-methoxy-phenyl)-2,4,6-trimethyl-benzenesulfonamide

Step A: N-(4-Methoxy-phenyl)-2,4,6-trimethyl-N-[4-(tetrahydro-pyran-2-yloxy)-benzyl]-benzenesulfonamide To a solution of (4-methoxy-phenyl)-[4-(tetrahydro-pyran-2-yloxy)-benzyl]-amine (0.100 g, 0.319 mmol) and triethylamine (0.133 mL, 0.957 mmol) in 2 mL methylene chloride was added 2-mesitylenesulfonyl chloride (0.139 g, 0.638 mmol). The reaction mixture was stirred at room temperature overnight. Saturated aqueous sodium bicarbonate was added and the layers were separated. The aqueous layer was extracted with 2 mL methylene chloride and the combined organic layers were evaporated to afford the title compound of Step A which was used in the next step without further purification.

Step B: N-(4-Hydroxy-benzyl)-N-(4-methoxy-phenyl)-2,4,6-trimethyl-benzenesulfonamide The crude N-(4-methoxy-phenyl)-2,4,6-trimethyl-N-[4-(tetrahydro-pyran-2-yloxy)-benzyl]-benzenesulfonamide prepared in Step A was suspended in 2 mL of a 3:1 (v/v) mixture of ethanol:1N HCl and was stirred at room temperature overnight. The reaction mixture was quenched with saturated aqueous sodium bicarbonate and the aqueous solution was washed with methylene chloride. The organic layer was concentrated. The residue was purified by reverse phase HPLC (98:2 water:0.1% trifluoracetic acid to 98:2 acetonitrile:water) to afford the title compound. MS 411 (M+1)$^+$

Example 202

N-(4-Hydroxy-benzyl)-N-(4-methoxy-phenyl)-benzenesulfonamide

Prepared in a manner analogous to that described in Example 201. $^1$H NMR (CD$_3$OD) δ 7.71–7.66 (m, 3H), 7.60–7.54 (m, 2H), 7.00 (d, 2H, J=10.8 Hz), 6.83–6.72 (m, 4H), 6.63 (d, 2H, J=11.2 Hz), 4.63 (s, 2H), 3.73 (s, 3H).

Example 203

N-(4-Hydroxy-benzyl)-4-methoxy-N-(4-methoxy-phenyl)-benzenesulfonamide

Prepared in a manner analogous to that described in Example 201. $^1$H NMR (CD$_3$OD) δ 7.59 (m, 2H), 7.07 (m, 2H), 7.00 (m, 2H), 6.83 (m, 2H), 6.73 (m, 2H), 6.62 (m, 2H), 4.60 (s, 2H), 3.89 (s, 3H), 3.72 (s, 3H).

Example 204

Cyclohexanecarboxylic acid (4-hydroxy-benzyl)-(4-methoxy-phenyl)-amide

Prepared in a manner analogous to that described in Example 201. $^1$H NMR (CD$_3$OD) δ 6.96 (d, 2H, J=8.6 Hz), 6.90 (s, 4H), 6.68 (d, 2H, J=8.6 Hz), 4.72 (s, 2H), 3.80 (s, 3H), 2.21 (m, 1H), 1.70–0.90 (m, 10H).

Example 205

Naphthalene-1-sulfonic acid (4-hydroxy-benzyl)-(4-methoxy-phenyl)-amide

Prepared in a manner analogous to that described in Example 201. $^1$H NMR (CD$_3$OD) δ 8.52 (m, 1H), 8.14 (m, 2H), 8.02 (m, 1H), 7.65–7.51 (m, 3H), 6.93 (m, 2H), 6.75 (m, 2H), 6.62 (m, 4H), 4.71 (s, 2H), 3.69 (s, 3H).

Example 206

Naphthalene-2-sulfonic acid (4-hydroxy-benzyl)-(4-methoxy-phenyl)-amide

Prepared in a manner analogous to that described in Example 201. $^1$H NMR (CD$_3$OD) δ 8.24 (s, 1H), 8.07–8.00 (m, 3H), 7.74–7.62 (m, 3H), 7.02 (d, 2H, J=11.6 Hz), 6.82 (d, 2H, J=11.6 Hz), 6.72 (d, 2H, J=12.0 Hz), 6.63 (d, 2H, J=10.8 Hz), 4.70 (s, 2H), 3.72 (s, 3H).

TABLE 11

| Example | X | R$^5$ | MS (M + 1)$^+$ or $^1$H NMR |
|---|---|---|---|
| 201 | SO$_2$ | 2,4,6-trimethyl-phenyl | $^1$H NMR (CD$_3$OD) δ 6.95 (m, 4H), 6.84 (m, 2H), 6.71 (d, 2H, J=9.2 Hz), 6.63 (d, 2H, J=8.6 Hz), 4.72 (s, 2H), 3.72 (s, 3H), 2.44 (s, 6H), 2.29 (s, 3H). |
| 202 | SO$_2$ | Ph | $^1$H NMR (CD$_3$OD) δ 7.71–7.66 (m, 3H), 7.60–7.54 (m, 2H), 7.00 (d, 2H, J=10.8 Hz), 6.83–6.72 (m, 4H), 6.63 (d, 2H, J=11.2 Hz), 4.63 (s, 2H), 3.73 (s, 3H). |
| 203 | SO$_2$ | p-anisoyl | $^1$H NMR (CD$_3$OD) δ 7.59 (m, 2H), 7.07 (m, 2H), 7.00 (m, 2H), 6.83 (m, 2H), 6.73 (m, 2H), 6.62 (m, 2H), 4.60 (s, 2H), 3.89 (s, 3H), 3.72 (s, 3H). |
| 204 | CO | cyclohexyl | $^1$H NMR (CD$_3$OD) δ 6.96 (d, 2H, J=8.6 Hz), 6.90 (s, 4H), 6.68 (d, 2H, J=8.6 Hz), 4.72 (s, 2H), 3.80 (s, 3H), 2.21 (m, 1H), 1.70–0.90 (m, 10H). |
| 205 | SO$_2$ | 1-naphthyl | $^1$H NMR (CD$_3$OD) δ 8.52 (m, 1H), 8.14 (m, 2H), 8.02 (m, 1H), 7.65–7.51 (m, 3H), 6.93 (m, 2H), 6.75 (m, 2H), 6.62 (m, 4H), 4.71 (s, 2H), 3.69 (s, 3H). |
| 206 | SO$_2$ | 2-naphthyl | $^1$H NMR (CD$_3$OD) δ 8.24 (s, 1H), 8.07–8.00 (m, 3H), 7.74–7.62 (m, 3H), 7.02 (d, 2H, J=11.6 Hz), 6.82 (d, 2H, J=11.6 Hz), 6.72 (d, 2H, J=12.0 Hz), 6.63 (d, 2H, J=10.8 Hz), 4.70 (s, 2H), 3.72 (s, 3H). |

EXAMPLES 207 TO 212

The following miscellaneous compounds, prepared as disclosed in Examples 207–212 and shown in Table 12 hereinbelow, were prepared according to methods analogous to those illustrated in Schemes 1–5 hereinabove, including combinations and/or variations thereon that will be readily apparent to one skilled in the relevant art.

Example 207

3-{4-[(3-Hydroxy-benzyl)-(2,4,6-trimethyl-benzenesulfonyl)-amino]-phenyl}-acrylic acid methyl ester To a solution of 3-{4-[[3-(tetrahydro-pyran-2-yloxy)-benzyl]-(2,4,6-trimethylbenzenesulfonyl)-amino]-phenyl}-acrylic acid methyl ester in 0.5 mL MeOH and 0.2 mL methylene chloride was added HCl (0.78 mL of a 4.0M solution in 1,4-dioxane, 3.12 mmol) and triethylsilane (0.20 mL, 1.25 mmol). The reaction mixture was stirred at room temperature for 24 hr. Saturated aqueous sodium bicarbonate was added and the aqueous solution was washed with methylene chloride. The organic layer was separated, dried (magnesium sulfate), and concentrated. Medium pressure silica gel chromatography (methylene chloride to 5% ethyl acetate/methylene chloride) afforded 0.050 g of 3-{4-[(3-hydroxy-benzyl)-(2,4,6-trimethyl-benzenesulfonyl)-amino]-phenyl}-acrylic acid methyl ester. MS 466.4 (M+1)$^+$

Example 208

3-{4-[(3-Hydroxy-benzyl)-(2,4,6-trimethyl-benzene-sulfonyl)-amino]-phenyl}-acrylic acid To a solution of 3-{4-[(3-hydroxy-benzyl)-(2,4,6-trimethyl-benzenesulfonyl)-amino]-phenyl}-acrylic acid methyl ester (0.040 g, 0.08 mmol) in 0.5 mL tetrahydrofuran was added sodium hydroxide (0.010 g, 0.25 mmol) in 0.5 mL water. The reaction was stirred at room temperature for 24 hr. The reaction mixture was adjusted to a pH of 4 with 1N HCl and water was added. The aqueous solution was washed with methylene chloride and the organic layer was dried (magnesium sulfate) and concentrated. Preparative TLC afforded 3-{4-[(3-hydroxy-benzyl)-(2,4,6-trimethyl-benzenesulfonyl)-amino]-phenyl}-acrylic acid. $^1$H NMR (CDCl$_3$) δ 7.58 (d, 1H, J=16 Hz), 7.29 (d, 2H, J=8.4 Hz), 7.04 (d, 2H, J=8.4 Hz), 7.05–7.00 (m, 1H), 6.86 (s, 2H), 6.70–6.60 (m, 3H), 6.28 (d, 1H, J=16 Hz), 4.77 (s, 2H), 2.45 (s, 6H), 2.25 (s, 3H).

Example 209

3-{4-[(3-Hydroxy-benzyl)-(2,4,6-trimethyl-benzene-sulfonyl)-amino]-phenyl}-propionic acid methyl ester Step A: 3-{4-[[3-(Tetrahydro-pyran-2-yloxy)-benzyl]-(2,4,6-trimethyl-benzenesulfonyl)-amino]-phenyl}-propionic acid methyl ester To a solution of 3-{4-[[3-(tetrahydro-pyran-2-yloxy)-benzyl]-(2,4,6-trimethyl-benzenesulfonyl)-amino]-phenyl}-acrylic acid methyl ester (0.252 g, 0.46 mmol) in methanol was added palladium black (catalytic amount) and ammonium formate (0.289 g, 4.58 mmol). The reaction mixture was stirred at 60° C. for 24 hr. Additional palladium black (catalytic amount) and ammonium formate (0.289 g, 4.58 mmol) were added and the reaction mixture was stirred at 60° C. for 24 hr. The reaction mixture was filtered through diatomaceous earth and the filter cake was washed with water and saturated aqueous sodium bicarbonate. The aqueous solution was washed with methylene chloride. The organic layer was concentrated to afford 0.172 g of the title compound of Step A. $^1$H NMR (CDCl$_3$) δ 7.10–7.05 (m, 1H), 7.00–6.90 (m, 4H), 6.89–6.80 (m, 4H), 6.75–6.70 (m, 1H), 5.27–5.25 (m, 1H), 4.80–4.70 (m, 2H), 3.85–3.75 (m, 1H), 3.60 (s, 3H), 3.55–3.50 (m, 1H), 2.82 (t, 2H, J=7.6 Hz), 2.53 (t, 2H, J=6.8 Hz), 2.43 (s, 6H), 2.26 (s, 3H), 2.00–1.90 (m, 1H), 1.85–1.75 (m, 2H) 1.65–1.50 (m, 3H).

Step B: 3-{4-[(3-Hydroxy-benzyl)-(2,4,6-trimethyl-benzenesulfonyl)-amino]-phenyl}-propionic acid methyl ester To a solution of 3-{4-[[3-(tetrahydro-pyran-2-yloxy)-benzyl]-(2,4,6-trimethyl-benzenesulfonyl)-amino]-phenyl}-propionic acid methyl ester in 0.5 mL methanol and 0.3 mL tetrahydrofuran was added HCl (0.52 mL of a 4.0M solution in 1,4-dioxane, 2.09 mmol) and triethylsilane (0.134 mL, 0.84 mmol). The reaction mixture was stirred at room temperature for 24 hr. Saturated aqueous sodium bicarbonate was added and the aqueous solution was washed with methylene chloride. The organic layer was separated, dried (magnesium sulfate), and concentrated. Preparative thin layer chromatography afforded 0.059 g of 3-{4-[(3-hydroxybenzyl)-(2,4,6-trimethyl-benzenesulfonyl)-amino]-phenyl}-propionic acid methyl ester. $^1$H NMR (CDCl$_3$) δ 7.03 (t, 1H, J=8.0 Hz), 6.95–6.80 (m, 6H), 6.68–6.62 (m, 2H), 6.48 (bs, 1H), 4.69 (s, 2H), 3.59 (s, 3H), 2.81 (t, 2H, J=7.6 Hz), 2.51 (t, 2H, J=7.6 Hz), 2.41 (s, 6H), 2.24 (s, 3H).

Example 210

3-{4-[(3-Hydroxy-benzyl)-(2,4,6-trimethyl-benzene-sulfonyl)-amino]-phenyl}-propionic acid To a solution of 3-{4-[(3-hydroxy-benzyl)-(2,4,6-trimethyl-benzenesulfonyl)-amino]-phenyl}-propionic acid methyl ester (0.017 g, 0.04 mmol) in 0.5 mL tetrahydrofuran was added sodium hydroxide (0.004 g, 0.11 mmol) in 0.1 mL water. The reaction was stirred at room temperature for 24 hr. The reaction mixture was adjusted to a pH of 4 with 1N HCl and water was added. The aqueous solution was washed with methylene chloride and the organic layer was concentrated to afford 0.015 g of 3-{4-[(3-hydroxy-benzyl)-(2,4,6-trimethyl-benzenesulfonyl)-amino]-phenyl}-propionic acid. $^1$H NMR (CDCl$_3$) δ 7.05 (t, 1H, J=7.6 Hz), 7.00–6.93 (m, 2H), 6.90–6.80 (m, 4H), 6.70–6.62 (m, 2H), 6.43 (bs, 1H), 4.69 (s, 2H), 2.83 (t, 2H, J=7.2 Hz), 2.56 (t, 2H, J=7.2 Hz), 2.42 (s, 6H), 2.24 (s, 3H).

Example 211

N-(2-Chloro-4-hydroxy-benzyl)-N-[4-(3-hydroxy-propyl)-phenyl]-2,4,6-trimethyl-benzenesulfonamide To a solution of N-(2-chloro-4-hydroxy-benzyl)-2,4,6-trimethyl-N-[4-(3-oxo-propyl)-phenyl]-benzenesulfonamide (0.036 g, 0.08 mmol) in 0.2 mL methanol and 0.2 mL methylene chloride was added sodium borohydride (0.014 g, 0.38 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. Medium pressure silica gel chromatography (40% ethyl acetate/hexanes) afforded 0.018 g of N-(2-chloro-4-hydroxy-benzyl)-N-[4-(3-hydroxy-propyl)-phenyl]-2,4,6-trimethyl-benzenesulfonamide. MS 474.0 (M+1)$^+$

Example 212

N-(3-Hydroxy-benzyl)-N-[4-(3-hydroxy-propyl)-phenyl]-2,4,6-trimethyl-benzenesulfonamide To a solution of N-(3-hydroxy-benzyl)-2,4,6-trimethyl-N-[4-(3-oxo-propyl)-phenyl]-benzenesulfonamide (0.040 g, 0.09 mmol) in 2 mL methylene chloride was added 4-methylpiperidine (0.015 g, 0.15 mmol) and NaB(OAc)$_3$H (0.047 g, 0.22 mmol). The reaction mixture was stirred at room temperature for 24 hr. Saturated aqueous sodium bicarbonate was added and the aqueous solution was washed with methylene chloride. The organic layer was dried (magnesium sulfate) and concentrated. Medium pressure silica gel chromatography (10% methanol/methylene chloride) followed by further medium-pressure chromatography (40% ethyl acetate/hexanes) afforded a mixture comprising 0.008 g of N-(3-hydroxy-benzyl)-2,4,6-trimethyl-N-{4-[3-(4-methyl-piperidin-1-yl)-propyl]-phenyl}-benzenesulfonamide and 0.017 g of N-(3-hydroxy-benzyl)-N-[4-(3-hydroxy-propyl)phenyl]-2,4,6-trimethyl-benzenesulfonamide. MS 440.2 (M+1)$^+$

TABLE 12

| Example | Structure | MS (M + 1)+ or 1HNMR |
|---|---|---|
| 207 | 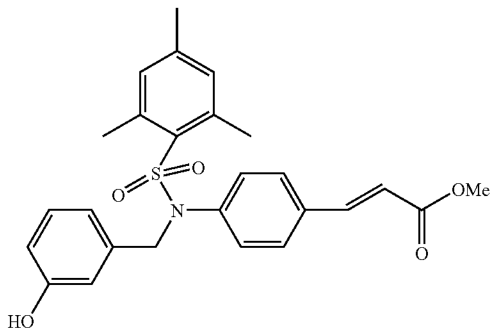 | 466.4 |
| 208 | 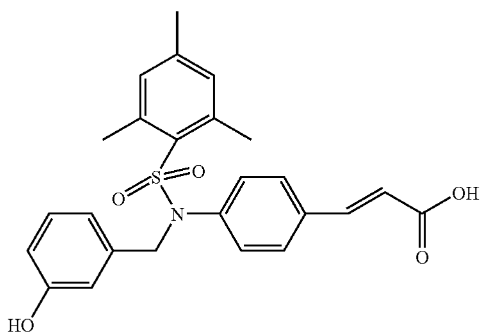 | 1H NMR (CDCl3) δ 7.58 (d, 1H, J=16 Hz), 7.29 (d, 2H, J=8.4 Hz), 7.04 (d, 2H, J=8.4 Hz), 7.05–7.00 (m, 1H), 6.86 (s, 2H), 6.70–6.60 (m, 3H), 6.28 (d, 1H, J=16 Hz), 4.77 (s, 2H), 2.45 (s, 6H), 2.25 (s, 3H). |
| 209 | 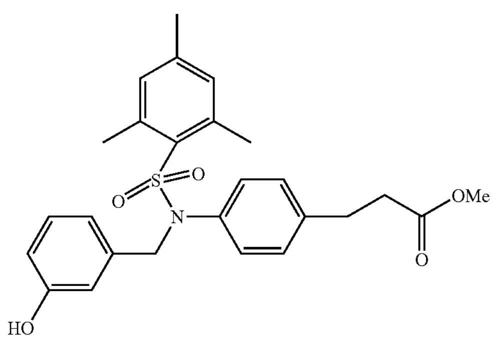 | 1H NMR (CDCl3) δ 7.03 (t, 1H, J=8.0 Hz), 6.95–6.80 (m, 6H), 6.68–6.62 (m, 2H), 6.48 (bs, 1H), 4.69 (s, 2H), 3.59 (s, 3H), 2.81 (t, 2H, J=7.6 Hz), 2.51 (t, 2H, J=7.6 Hz), 2.41 (s, 6H), 2.24 (s, 3H). |
| 210 | 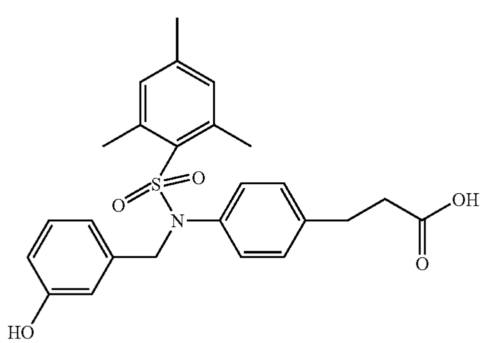 | 1H NMR (CDCl3) δ 7.05 (t, 1H, J=7.6 Hz), 7.00–6.93 (m, 2H), 6.90–6.80 (m, 4H), 6.70–6.62 (m, 2H), 6.43 (bs, 1H), 4.69 (s, 2H), 2.83 (t, 2H, J=7.2 Hz), 2.56 (t, 2H, J=7.2 Hz), 2.42 (s, 6H), 2.24 (s, 3H). |

TABLE 12-continued

| Example | Structure | MS (M + 1)+ or 1HNMR |
|---|---|---|
| 211 | 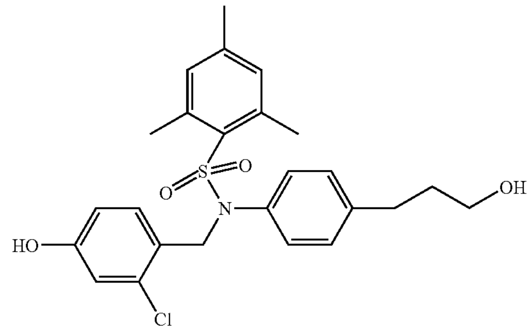 | 474.0 |
| 212 | 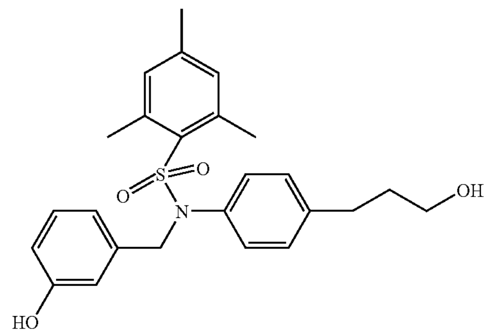 | 440.2 |

BIOLOGICAL METHODOLOGIES

All reagents were obtained from Sigma Chemical Co. (St. Louis, Mo.) unless otherwise indicated.

Method for ER Binding Assay cDNA cloning of human ERα and ERβ: The coding region of human ERα was cloned by RT-PCR from human breast cancer cell mRNA using Expand™ High Fidelity PCR System (Boehringer-Mannheim; Indianapolis, Ind.) according to manufacturer's instructions. The coding region of human ERβ was cloned by RT-PCR from human testes and pituitary mRNA also using the Expand™ High Fidelity PCR System according to manufacturer's instructions. PCR products were cloned into pCR2.1 TA Cloning Kit (Invitrogen; Carlsbad, Calif.) and sequenced. Each receptor coding region was subcloned into the mammalian expression vector pcDNA3 (Invitrogen; Carlsbad, Calif.).

Mammalian Cell Expression.

Receptor proteins were overexpressed in 293T cells. These cells, derived from HEK293 cells (ATCC; Manassas, Va.), have been engineered to stably express large T antigen and can therefore replicate plasmids containing a SV40 origin of replication to high copy numbers. The 293T cells were transfected with either hERα-pcDNA3 or hERβ-pcDNA3 using lipofectamine as described by the manufacturer (Gibco/BRL; Bethesda, Md.). Cells were harvested in phosphate buffered saline (PBS) with 0.5 mM EDTA at 48 hr. post-transfection. Cell pellets were washed once with PBS/EDTA. Whole cell lysates were prepared by homogenization in TEG buffer (50 mM Tris pH 7.4, 1.5 mM EDTA, 50 mM NaCl, 10% glycerol, 5 mM DTT, 5 μg/ml aprotinin, 10 μg/ml leupeptin, 0.1 mg/ml Pefabloc) using a homogenizer. Extracts were centrifuged at 100,000×g for 2 hours at 4° C. and the supernatants were collected. Total protein concentrations were determined using BioRad reagent (Bio-Rad; Hercules, Calif.).

Competition binding assay. The ability of various compounds to inhibit [3H]-estradiol binding was measured by a competition binding assay using dextran-coated charcoal as described previously. See, for example, R. E. Leake, et al., "Steroid Hormones, A Practical Approach", IRL Press Ltd., Oxford, pp. 67–92 (1987). Cellular extracts expressing either hERα or hERβ were incubated in the presence of increasing concentrations of competitor and a fixed concentration of [3H]-estradiol (141 Ci/mmol, New England Nuclear; Boston, Mass.) in 50 mM TrisHCl pH 7.4, 1.5 mM EDTA, 50 mM NaCl, 10% glycerol, 5 mM DTT, 0.5 mg/mL β-lactoglobulin in a final volume of 0.2 mL. All competitors were dissolved in dimethylsulfoxide. The final concentration of receptor was 50 pM with 0.5 nM [3H]-estradiol. After 16 hr. at 4° C., dextran-coated charcoal (20 μL) was added. After 15 minutes at room temperature, the charcoal was removed by centrifugation and the radioactive ligand present in the supernatant was measured by scintillation counting.

The invention claimed is:

1. A compound of structural formula (I)

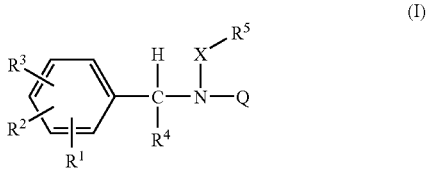

(I)

or a pharmaceutically acceptable salt, stereoisomer or prodrug thereof, or a pharmaceutically acceptable salt of said stereoisomer or prodrug, wherein:

Q is

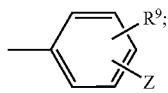

$R^1$, $R^2$, $R^3$, and $R^9$ are, independently, hydrogen; hydroxy; halogen; cyano; —$(C_1-C_6)$alkyl, optionally substituted with 1–3 fluorine atoms; or —$O(C_1-C_6)$alkyl, optionally substituted with 1–3 fluorine atoms;

$R^4$ is hydrogen or —$(C_1-C_6)$alkyl;

$R^5$ is —$(C_1-C_7)$alkyl, optionally substituted with from 1–6 halogen atoms; —$(C_2-C_6)$alkenyl; —$(C_2-C_6)$alkenyl-M; or —$(CH_2)_n$-M, wherein n is 0–5; and wherein M is:
  (i) a fully saturated 3–8 membered ring, or a partially saturated 5–8 membered ring, optionally having from 1–4 heteratoms indepently selected from the group consisting of oxygen, nitrogen, and sulfur; or
  (ii) a bicyclic ring comprising two fused partially saturated, fully saturated, or fully unsaturated 5- or 6-membered rings, optionally having from 1–4 heteroatoms independently selected from the group consisting of oxygen, nitrogen and sulfur; or
  (iii) phenyl; isoxazoly; thiazolyl; furanyl; isothiazolyl; thienyl; imidazolyl; pyrazolyl; pyridyl; pyrimidyl or pyrazinyl; wherein M is optionally substituted with 1–3 substituents independently selected from the group consisting of hydroxy; halogen; cyano; nitro; formyl; amino; carbamoyl; thiol; —$(C_1-C_6)$alkyl or —$O(C_1-C_6)$alkyl, optionally substituted with 1–5 halogen atoms; —$(C_3-C_8)$cycloalkyl or phenyl, optionally substituted with 1–3 halogen atoms; —$SO(C_1-C_6)$alkyl or —$SO_2(C_1-C_6)$alkyl, optionally substituted with 1–5 halogen atoms; —$S(C_1-C_6)$alkyl, optionally substituted with 1–5 halogen atoms; —$(C_1-C_4)$alkoxycarbonyl; —$(C_1-C_6)$alkyl-$(C_3-C_8)$cycloalkyl; —$(C_0-C_4)$sulfonamido; mono-N— or di-N,N-$(C_1-C_4)$alkylcarbamoyl; mono-N or di-N,N-$(C_1-C_4)$alkylamino-$SO_2$; mono-N or di-N,N-$(C_1-C_4)$alkylamino; —$(C_1-C_8)$alkanoyl; —$(C_{C1}-C_4)$alkoxycarbonylamino; and —$(C_1-C_4)$alkoxycarbonylamino;

X is CO or $SO_2$;

Z is —$O(CH_2)_n$—$NR^aR^b$; or —$(CH_2)_n$—$NR^aR^b$; wherein each n is 0–5 inclusive, provided that when Z is —$O$—$(CH_2)_n$—$NR^aR^b$, n is 2–5; and $R^a$ and $R^b$, taken together with the nitrogen atom to which they are attached, are a heterocycloalkyl group selected from pyrrolidinyl or piperidinyl, wherein said pyrrolidinyl or piperidinyl is optionally substituted with 1–3 substituents independently selected from the group consisting of hydroxy; halogen; cyano; nitro; amino; carbamoyl; —$(C_1-C_6)$alkyl or —$O(C_1-C_6)$alkyl, optionally substituted with 1–5 halogen atoms; —$(C_1-C_3)$alkyl-$O(C_1-C_3)$alkyl; —$(C_1-C_4)$OH; carboxylate; —$(C_1-C_3)$phenyl; —$(C_3-C_8)$cycloalkyl; phenyl, optionally substituted with 1–3 halogen atoms; —$SO(C_1-C_6)$alkyl or —$SO_2(C_1-C_6)$alkyl, optionally substituted with 1–5 halogen atoms; —$S(C_1-C_6)$alkyl, optionally substituted with 1–5 halogen atoms; —$(C_1-C_4)$alkoxycarbonyl; —$(C_1-C_6)$alkyl-$(C_3-C_8)$cycloalkyl; —$(C_0-C_4)$sulfonamido; —$(C_1-C_4)$cycloalkylsulfonamido; mono-N- or di-N,N-$(C_1-C_4)$alkylcarbamoyl; mono-N or di-N,N-$(C_1-C_4)$alkylamino-$SO_2$; mono-N or di-N,N-$(C_1-C_4)$alkylamino; —$(C_1-C_8)$alkanoyl; —$(C_1-C_4)$alkanoylamino; and —$(C_1-C_4)$alkoxycarbonylamino.

2. A compound of claim 1, wherein:

$R^5$ is —$(C_1-C_6)$alkyl, optionally substituted with from 1–6 halogen atoms; —$(C_2-C_6)$alkenyl; —$(C_2-C_6)$alkenyl-M; or —$(CH_2)_n$-M, wherein n is 0 to 3; and M is selected from the group consisting of cyclopropyl; cyclobutyl; cyclopentyl; cyclohexyl; phenyl; quinolinyl; isoquinolinyl; naphthalenyl; isoxazolyl; oxazolyl; thiazolyl; furanyl; isothiazolyl; thienyl; imidazolyl; pyrazolyl; pyridyl; pyrimidyl; and pyrazinyl, each optionally substituted with 1–3 substituents independently selected from the group consisting of hydroxy; halogen; cyano; nitro; formyl; amino; carbamoyl; thiol; —$(C_1-C_6)$alkyl or —$O(C_1-C_6)$alkyl, optionally substituted with 1–5 halogen atoms; —$(C_3-C_8)$cycloalkyl or phenyl, optionally substituted with 1–3 halogen atoms; —$SO(C_1-C_6)$alkyl or —$SO_2(C_1-C_6)$alkyl, optionally substituted with 1–5 halogen atoms; —$S(C_1-C_6)$alkyl, optionally substituted with 1–5 halogen atoms; —$(C_1-C_4)$alkoxycarbonyl; —$(C_1-C_6)$alkyl-$(C_3-C_8)$cycloalkyl; —$(C_0-C_4)$sulfonamido; mono-N— di-N,N-$(C_1-C_4)$alkylcarbamoyl; mono-N or di-N,N-$(C_1-C_4)$alkylamino-$SO_2$; mono-N or di-N,N-$(C_1-C_4)$alkylamino; —$(C_1-C_8)$alkanoyl; —$(C_1-C_4)$alkanoylamino; and —$(C_1-C_4)$alkoxycarbonylamino; and $R^a$ and $R^b$, taken together with the nitrogen atom to which they are attached, are a heterocylcoalkyl group selected from pyrrodinyl or piperideinyl, wherein said pyrrolidinyl or piperidinyl is optionally substituted with 1–3 substituents independently selected from the group consisting of hydroxy; halogen; cyano; nitro; amino; carbamoyl; —$(C_1-C_6)$alkyl or —$O(C_1-C_6)$alkyl, optionally substituted with 1–5 halogen atoms; —$(C_1-C_3)$alkyl-$O(C_1-C_3)$alkyl; —$(C_1-C_4)$OH; carboxylate; —$(C_1-C_3)$phenyl; —$(C_3-C_8)$cycloalkyl; phenyl, optionally substituted with 1–3 halogen atoms; —$(C_1-C_4)$alkoxycarbonyl; and —$(C_1-C_6)$alkyl-$(C_3-C_8)$cycloalkyl.

3. A compound of claim 1, wherein:

$R^1$, $R^2$, $R^3$, and $R^9$ are, independently, hydrogen; hydroxy; halogen; —$(C_1-C_4)$alkyl,optionally substituted with 1–3 fluorine atoms; or —$O(C_1-C_2)$alkyl, optionally substituted with 1–3 fluorine atoms;

$R^4$ is hydrogen;

$R^5$ is -(ethenyl)-M or -M, wherein M is cyclopentyl, cyclohexyl, phenyl, or isoxazolyl, optionally substituted with 1–5 halogen atoms; —$(C_1-C_4)$alkyl, optionally substituted with 1–3 halogen atoms; or —$O(C_1-C_4)$alkyl, optionally substituted with 1–3 halogen atoms;

Z is —$O(CH_2)_n$—$NR^aR^b$ or —$(CH_2)_n$—$NR^aR^b$; wherein each n is 1–5 inclusive, provided that when Z is —$O$—$(CH_2)_n$—$NR^aR^b$, n is 2–4; and $R^a$ and $R^b$, taken together with the nitrogen atom to which they are attached, form a heterocycloalkyl ring selected from pyrrolidinyl or piperidinyl wherein said pyrrolidinyl or piperidinyl is optionally substituted with 1–3 substituents independently selected from the group consisting of hydroxy; halogen; —$(C_1-C_4)$alkyl, optionally substituted with 1–5 halogen atoms;

—(C₁–C₃)alkyl-O(C₁–C₃)alkyl; —(C₁–C₃)OH; carboxylate; —(C₁–C₃)phenyl; —(C₅–C₇)cycloalkyl; and phenyl, optionally substituted with 1–3 halogen atoms.

4. A compound of claim 1, wherein:
$R^1$, $R^2$, $R^3$, and $R^9$ are, independently, hydrogen; hydroxy; halogen; —(C₁–C₃)alkyl, or —CF₃;
$R^5$ is ethenylphenyl; cyclohexyl; or phenyl, each optionally substituted with 1–3 substituents independently selected from the group consisting of halogen, hydroxy, —(C₁–C₃)alkyl, —CF₃; and —OCH₃;
X is CO or SO₂;
Z is —O(CH₂)₂—NR$^a$R$^b$; or —(CH₂)₃—NR$^a$R$^b$; and
R$^a$ and R$^b$, taken together with the nitrogen atom to which they are attached, are a heterocycloalkyl ring selected from pyrrolidinyl or piperidinyl wherein said pyrrolidinyl or piperidinyl is optionally substituted with 1–3 substituents independently selected from the group consisting of hydroxy; halogen; —(C₁–C₃)alkyl, optionally substituted with 1–3 halogen atoms; —(C₁–C₂)alkyl-(C₁–C₂)alkoxy; —(C₁–C₂)OH; carboxylate; and —CH₂-phenyl.

5. A compound of claim 1 selected from the group consisting of:
cyclohexanecarboxylic acid (4-hydroxy-benzyl)-[4-(2-pyrrolidin-1-yl-ethoxy)-phenyl]-amide;
cyclohex-3-enecarboxylic acid (4-hydroxy-benzyl)-[4-(2-pyrrolidin-1-yl-ethoxy)-phenyl]-amide;
2-phenyl-ethenesulfonic acid (4-hydroxy-benzyl)-[4-(2-pyrrolidin-1-yl-ethoxy)-phenyl]-amide;
N-(3-hydroxy-benzyl)-4-methoxy-N-[4-(2-pyrrolidin-1-yl-ethoxy)-phenyl]-benzenesulfonamide;
2-phenyl-ethenesulfonic acid (3-hydroxy-benzyl)-[4-(2-pyrrolidin-1-yl-ethoxy)-phenyl]-amide;
N-{4-[3-(4-benzyl-piperidin-1-yl)-propyl]-phenyl}-N-(4-hydroxy-benzyl)-benzenesulfonamide;
2-chloro-N-(4-hydroxy-benzyl)-N-[4-(2-pyrrolidin-1-yl-ethoxy)-phenyl]-benzenesulfonamide;
N-(4-hydroxy-benzyl)-2,4,6-trimethyl-N-[4-(2-pyrrolidin-1-yl-ethoxy)-phenyl]-benzenesulfonamide;
N-(3-hydroxy-benzyl)-2,4,6-trimethyl-N-[4-(2-pyrrolidin-1-yl-ethoxy)-phenyl]-benzenesulfonamide;
N-(3-hydroxy-benzyl)-2,4,6-triisopropyl-N-[4-(2-pyrrolidin-1-yl-ethoxy)-phenyl]-benzenesulfonamide;
2,4-dichloro-N-(3-hydroxy-benzyl)-6-methyl-N-[4-(2-pyrrolidin-1-yl-ethoxy)-phenyl]-benzenesulfonamide;
N-(3-hydroxy-benzyl)-N-[4-(2-pyrrolidin-1-yl-ethoxy)-phenyl]-4-trifluoromethyl-benzamide;
5-chloro-N-(4-hydroxy-benzyl)-2-methyl-N-[4-(2-pyrrolidin-1-yl-ethoxy)-phenyl]-benzenesulfonamide;
4-bromo-N-(2-chloro-4-hydroxy-benzyl)-2-methyl-N-[4-(2-pyrrolidin-1-yl-ethoxy)-phenyl]-benzenesulfonamide;
2-chloro-N-(2-chloro-4-hydroxy-benzyl)-4-fluoro-N-[4-(2-pyrrolidin-1-yl-ethoxy)-phenyl]-benzenesulfonamide;
2,4-dichloro-N-(2-chloro-4-hydroxy-benzyl)-N-[4-(2-pyrrolidin-1-yl-ethoxy)-phenyl]-benzenesulfonamide;
4-bromo-2-ethyl-N-(4-hydroxy-benzyl)-N-[4-(2-pyrrolidin-1-yl-ethoxy)-phenyl]-benzenesulfonamide;
4-bromo-N-(4-hydroxy-benzyl)-2-methyl-N-[4-(2-pyrrolidin-1-yl-ethoxy)-phenyl]-benzenesulfonamide;
2,4-dichloro-N-(4-hydroxy-benzyl)-6-methyl-N-[4-(2-pyrrolidin-1-yl-ethoxy)-phenyl]-benzenesulfonamide;
2,4-dichloro-N-(4-hydroxy-benzyl)-N-[4-(2-pyrrolidin-1-yl-ethoxy)-phenyl]-benzenesulfonamide;
N-(3-hydroxy-benzyl)-2,4,6-trimethyl-N-[4-(3-pyrrolidin-1-yl-propyl)-phenyl]-benzenesulfonamide;
N-(3-hydroxy-benzyl)-N-{4-[3-(2-hydroxymethyl-pyrrolidin-1-yl)-propyl]-phenyl}-2,4,6-trimethyl-benzenesulfonamide;
N-[4-(3-cyclopentylamino-propyl)-phenyl]-N-(3-hydroxy-benzyl)-2,4,6-trimethyl-benzenesulfonamide;
N-(3-hydroxy-benzyl)-2,4,6-trimethyl-N-[4-(2-piperidin-1-yl-ethoxy)-phenyl]-benzenesulfonamide;
N-(3-hydroxy-benzyl)-2,4,6-trimethyl-N-[4-(3-thiomorpholin-4-yl-propyl)-phenyl]-benzenesulfonamide;
N-{4-[3-(2,6-dimethyl-morpholin-4-yl)-propyl]-phenyl}-N-(3-hydroxy-benzyl)-2,4,6-trimethyl-benzenesulfonamide;
N-(3-hydroxy-benzyl)-2,4,6-trimethyl-N-{4-[3-(4-methyl-piperidin-1-yl)-propyl]-phenyl}-benzenesulfonamide;
N-(3-hydroxy-benzyl)-2,4,6-trimethyl-N-{4-[3-(2-propyl-piperidin-1-yl)-propyl]-phenyl}-benzenesulfonamide;
N-(3-hydroxy-benzyl)-2,4,6-trimethyl-N-{4-[3-(2-methyl-piperidin-1-yl)-propyl]-phenyl}-benzenesulfonamide;
N-(3-hydroxy-benzyl)-2,4,6-trimethyl-N-{4-[3-(2-methyl-pyrrolidin-1-yl)-propyl]-phenyl}-benzenesulfonamide;
N-(3-hydroxy-benzyl)-2,4,6-trimethyl-N-[4-(3-piperidin-1-yl-propyl)-phenyl]-benzenesulfonamide;
N-(2-chloro-4-hydroxy-benzyl)-N-{4-[3-(2-methoxymethyl-pyrrolidin-1-yl)-propyl]-phenyl}-2,4,6-trimethyl-benzenesulfonamide;
1-(3-{4-[(2-chloro-4-hydroxy-benzyl)-(2,4,6-trimethyl-benzenesulfonyl)-amino]-phenyl}-propyl)-pyrrolidine-2-carboxylic acid;
N-{4-[3-(2,6-dimethyl-piperidin-1-yl)-propyl]-phenyl}-N-(3-hydroxy-benzyl)-2,4,6-trimethyl-benzenesulfonamide;
N-(3-hydroxy-benzyl)-N-[4-(3-hydroxy-propyl)-phenyl]-2,4,6-trimethyl-benzenesulfonamide;
N-(2-chloro-4-hydroxy-benzyl)-4-methoxy-N-[4-(2-pyrrolidin-1-yl-ethoxy)-phenyl]-benzenesulfonamide;
4-chloro-N-(4-hydroxy-benzyl)-N-[4-(2-pyrrolidin-1-yl-ethoxy)-phenyl]-benzenesulfonamide;
or a pharmaceutically acceptable salt, stereoisomers, or prodrugs thereof, or the pharmaceutically acceptable salts of said steroisomers and prodrug.

6. A pharmaceutical composition comprising a compound of claim 1, a pharmaceutically acceptable salt, stereoisomer, or prodrug thereof, a pharmaceutically acceptable salt of said steroisomer or prodrug, and a pharmaceutically acceptable carrier, vehicle, or diluent.

7. A pharmaceutical composition comprising a compound of claim 1, a pharmaceutically acceptable salt, stereoisomer, or prodrug thereof, or a pharmaceutically acceptable salt of said steroisomer or prodrug; one or more of sodium fluoride, estrogen, a bone anabolic agent, a growth hormone or growth hormone secretagogue, a prostaglandin agonist/antagonist, a parathyroid hormone, or a prodrug thereof, or pharmaceutically acceptable salt thereof; and a pharmaceutically acceptable carrier, vehicle, or diluent.

* * * * *